(12) United States Patent
Pic et al.

(10) Patent No.: US 11,642,281 B2
(45) Date of Patent: May 9, 2023

(54) ENDOSCOPIC MEDICAL DEVICE FOR DISPENSING MATERIALS AND METHOD OF USE

(71) Applicant: Boston Scientific Scimed, Inc., Maple Grove, MN (US)

(72) Inventors: Andrew Pic, Northboro, MA (US); Matthew LaPlaca, Franklin, MA (US); Jennifer Golden, Norton, MA (US); Shawn Ryan, Littleton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 504 days.

(21) Appl. No.: 16/589,633

(22) Filed: Oct. 1, 2019

(65) Prior Publication Data
US 2020/0100986 A1    Apr. 2, 2020

Related U.S. Application Data

(60) Provisional application No. 62/848,226, filed on May 15, 2019, provisional application No. 62/831,900,
(Continued)

(51) Int. Cl.
*A61J 1/14* (2006.01)
*A61M 25/10* (2013.01)

(52) U.S. Cl.
CPC .......... *A61J 1/1443* (2013.01); *A61J 1/1481* (2015.05); *A61M 25/10* (2013.01); *A61M 2025/105* (2013.01)

(58) Field of Classification Search
CPC .... A61J 1/1443; A61J 1/1481; A61J 1/20–22; G05D 16/0663; G05D 16/107;
(Continued)

(56) References Cited

U.S. PATENT DOCUMENTS

| 471,854 A | 3/1892 | Howard |
| 881,238 A | 3/1908 | Hasbrouck |

(Continued)

FOREIGN PATENT DOCUMENTS

| CN | 101401956 B | 11/2012 |
| DE | 60215438 T2 | 8/2007 |

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
(Continued)

*Primary Examiner* — Benjamin J Klein
*Assistant Examiner* — Alessandro R Del Priore
(74) *Attorney, Agent, or Firm* — Bookoff McAndrews, PLLC

(57) ABSTRACT

A medical device including an application device with a first fluid path and a container movably attached to the application device. The container and the application device have a second fluid path therethrough, the container includes an inner chamber that is intermediate proximal and distal portions of the second fluid path, the inner chamber is fluidly isolated from the proximal portion of the second fluid path at a first position of the container, and the inner chamber is fluidly coupled to the proximal and distal portions of the second fluid path at a second position of the container. The first fluid path bypasses the container and the passage of fluid through the first fluid path is separately controllable from the passage of fluid through the second fluid path.

20 Claims, 28 Drawing Sheets

Related U.S. Application Data filed on Apr. 10, 2019, provisional application No. 62/747,863, filed on Oct. 19, 2018, provisional application No. 62/740,242, filed on Oct. 2, 2018.

(58) Field of Classification Search
CPC .............. A61M 11/02; A61M 15/0005; A61M 15/0008; A61M 2202/064; A61M 2205/8225; A61M 13/00; B05B 7/1413; B05B 12/087; A61B 2017/00495; F41B 11/62

See application file for complete search history.

(56) References Cited

U.S. PATENT DOCUMENTS

| | | | |
|---|---|---|---|
| 1,145,520 A | 7/1915 | Smith | |
| 1,599,959 A | 9/1926 | Buheiji | |
| 1,732,566 A | 10/1929 | McKendrick | |
| 2,151,418 A | 3/1939 | Bolté | |
| 2,185,927 A | 6/1940 | Shelanski | |
| 2,478,715 A | 8/1949 | Schmitt | |
| 2,623,519 A | 12/1952 | Cohen | |
| 3,669,113 A | 6/1972 | Altounyan et al. | |
| 3,940,061 A | 2/1976 | Gimple et al. | |
| 4,184,258 A | 6/1980 | Barrington et al. | |
| 4,427,450 A | 1/1984 | Kostansek | |
| 4,457,329 A | 7/1984 | Werley et al. | |
| 4,806,167 A | 2/1989 | Raythatha | |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Kneopfler | |
| 5,312,333 A | 5/1994 | Churinetz et al. | |
| 5,366,122 A | 11/1994 | Guentert et al. | |
| 5,445,612 A | 8/1995 | Terakura et al. | |
| 5,470,311 A | 11/1995 | Setterstrom et al. | |
| 5,884,621 A | 3/1999 | Matsugi et al. | |
| 5,951,531 A | 9/1999 | Ferdman et al. | |
| 5,957,119 A * | 9/1999 | Perry .................... F41B 11/724 | |
| | | | 137/234.5 |
| 6,003,512 A | 12/1999 | Gerde | |
| 6,021,776 A * | 2/2000 | Allred .................... A61M 11/02 | |
| | | | 128/200.14 |
| 6,484,750 B1 | 11/2002 | Foos et al. | |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 7,178,547 B2 | 2/2007 | Mackal | |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 8,673,065 B2 | 3/2014 | Burgess et al. | |
| 8,721,582 B2 | 5/2014 | Ji | |
| 8,728,032 B2 | 5/2014 | Ducharme et al. | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,067,011 B2 | 6/2015 | Zou et al. | |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2 | 12/2015 | Greenhalgh et al. | |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 | 5/2017 | Pohlmann et al. | |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 | 9/2018 | Eder et al. | |
| 10,173,019 B2 | 1/2019 | Kaufmann et al. | |
| 10,384,049 B2 | 8/2019 | Stanton et al. | |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 | 5/2021 | Hernandez | |
| 2004/0107963 A1 | 6/2004 | Finlay et al. | |
| 2004/0112378 A1* | 6/2004 | Djupesland ........ A61M 15/0021 | |
| | | | 128/207.18 |
| 2004/0182387 A1* | 9/2004 | Steiner .............. A61M 15/0015 | |
| | | | 128/203.15 |
| 2004/0249359 A1 | 12/2004 | Palasis et al. | |
| 2005/0121025 A1 | 6/2005 | Gamard et al. | |
| 2005/0147656 A1 | 7/2005 | McCarthy et al. | |
| 2005/0205087 A1* | 9/2005 | Kablik .................. B05B 7/1422 | |
| | | | 128/200.23 |
| 2005/0220721 A1 | 10/2005 | Kablik et al. | |
| 2006/0004314 A1 | 1/2006 | McCarthy et al. | |
| 2006/0213514 A1 | 9/2006 | Price et al. | |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0125375 A1 | 6/2007 | Finlay et al. | |
| 2007/0151560 A1 | 7/2007 | Price et al. | |
| 2007/0083137 A1 | 8/2007 | Hopman et al. | |
| 2007/0199824 A1 | 8/2007 | Hoerr et al. | |
| 2008/0021374 A1 | 1/2008 | Kawata | |
| 2008/0141991 A1 | 6/2008 | Liu | |
| 2008/0287907 A1 | 11/2008 | Gregory et al. | |
| 2009/0101144 A1 | 4/2009 | Gamard et al. | |
| 2009/0155342 A1 | 6/2009 | Diegemann et al. | |
| 2009/0281486 A1 | 11/2009 | Ducharme | |
| 2010/0121261 A1 | 5/2010 | Kablik et al. | |
| 2010/0160897 A1 | 6/2010 | Ducharme et al. | |
| 2010/0305505 A1* | 12/2010 | Ducharme .............. A61M 11/02 | |
| | | | 604/118 |
| 2010/0326438 A1* | 12/2010 | Dunne ................ A61M 15/002 | |
| | | | 128/203.15 |

(56) References Cited

U.S. PATENT DOCUMENTS

| | | |
|---|---|---|
| 2011/0073200 A1 | 3/2011 | Overvaag et al. |
| 2011/0178495 A1 | 7/2011 | Ji |
| 2011/0274726 A1 | 11/2011 | Guo et al. |
| 2011/0308516 A1 | 12/2011 | Price et al. |
| 2013/0206866 A1* | 8/2013 | Bullock .............. B05B 15/65 239/589 |
| 2013/0270365 A1* | 10/2013 | Schwarz ............. B05B 5/1691 239/310 |
| 2014/0203098 A1 | 7/2014 | Bierie |
| 2014/0271491 A1 | 9/2014 | Gittard et al. |
| 2015/0094649 A1 | 4/2015 | Gittard |
| 2015/0125513 A1 | 5/2015 | McCarthy |
| 2016/0074579 A1 | 3/2016 | Ilan et al. |
| 2016/0375202 A1 | 12/2016 | Goodman et al. |
| 2017/0106181 A1 | 4/2017 | Bonaldo et al. |
| 2017/0232141 A1 | 8/2017 | Surti et al. |
| 2017/0252479 A1 | 9/2017 | Ji et al. |
| 2017/0296760 A1 | 10/2017 | Lee et al. |
| 2018/0099088 A1 | 4/2018 | Gittard |
| 2018/0193574 A1* | 7/2018 | Smith .................. A61M 13/00 |
| 2018/0214160 A1 | 8/2018 | Hoskins et al. |
| 2018/0339144 A1 | 11/2018 | Greenhalgh et al. |
| 2019/0134366 A1 | 5/2019 | Erez et al. |
| 2019/0217315 A1 | 7/2019 | Maguire et al. |
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | |
|---|---|---|
| EP | 3052168 B1 | 11/2019 |
| FR | 2863503 A1 | 6/2005 |
| JP | H07118305 A | 5/1995 |
| WO | WO 98/43894 A1 | 10/1998 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2009061409 A1 | 5/2009 |
| WO | 2015050814 A1 | 4/2015 |
| WO | 2018157772 A1 | 9/2018 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.
Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.
Regalia, Kristen, et al. "Hemospray in Gastrointestinal Bleeding." Practical Gastroenterology. Endoscopy: Opening New Eyes, ser. 8, May 2014, pp. 13-24. 8.
Cook Medical. Hemospray Endoscopic Hemostat, Cook, 2014. (7 pages, in English).
"Hemospray Clinical Experience Shows Efficacy of a New Hemostasis Modality—v1", Cook Medical, 2012.
"Hemospray Clinical Experience Shows Efficacy of a New Hemostasis Modality—v2", Cook Medical, 2013.
"Hemospray Clinical Experience Shows Efficacy of a New Hemostasis Modality—v3", Cook Medical, 2014.
Aslanian, Harry R., and Loren Laine. "Hemostatic powder spray for GI bleeding." Gastrointestinal endoscopy 77.3 (2013): 508-510.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.
Retsch GmbH Haan. Sieve Analysis: Taking a Close Look at Quality, An Expert Guide to Particle Size Analysis. 2015. (56 pages, in English).
Micromeritics. Density Analysis, 2001. (6 pages, in English).
Micromeritics. "Application Note: Bulk and Skeletal Density Computations for the AutoPore." May 2012. (3 pages, in English).
Arefnia, Ali, et al. "Comparative Study on the Effect of Tire-Derived Aggregate on Specific Gravity of Kaolin." Electronic Journal of Geotechnical Engineering 18 (2013): 335-44.
Kesavan, Jana, et al. "Density Measurements of Materials Used in Aerosol Studies". Edgewood Chemical Biological Center Aberdeen Proving Ground Md, 2000.

\* cited by examiner

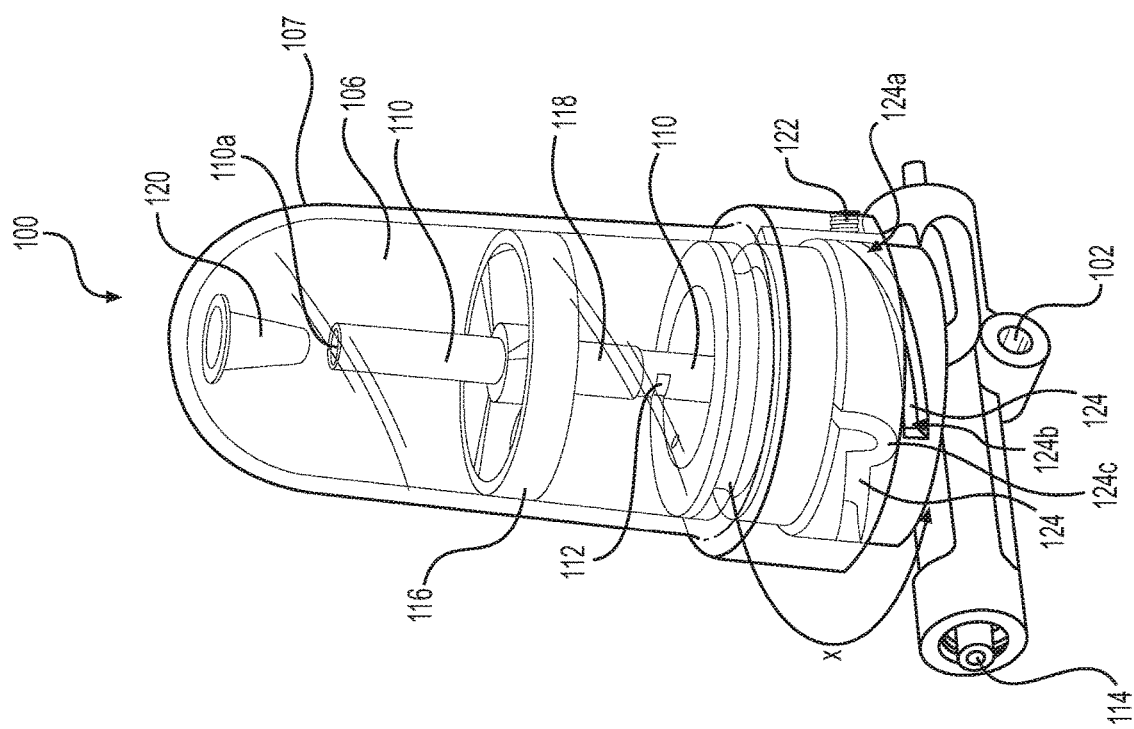
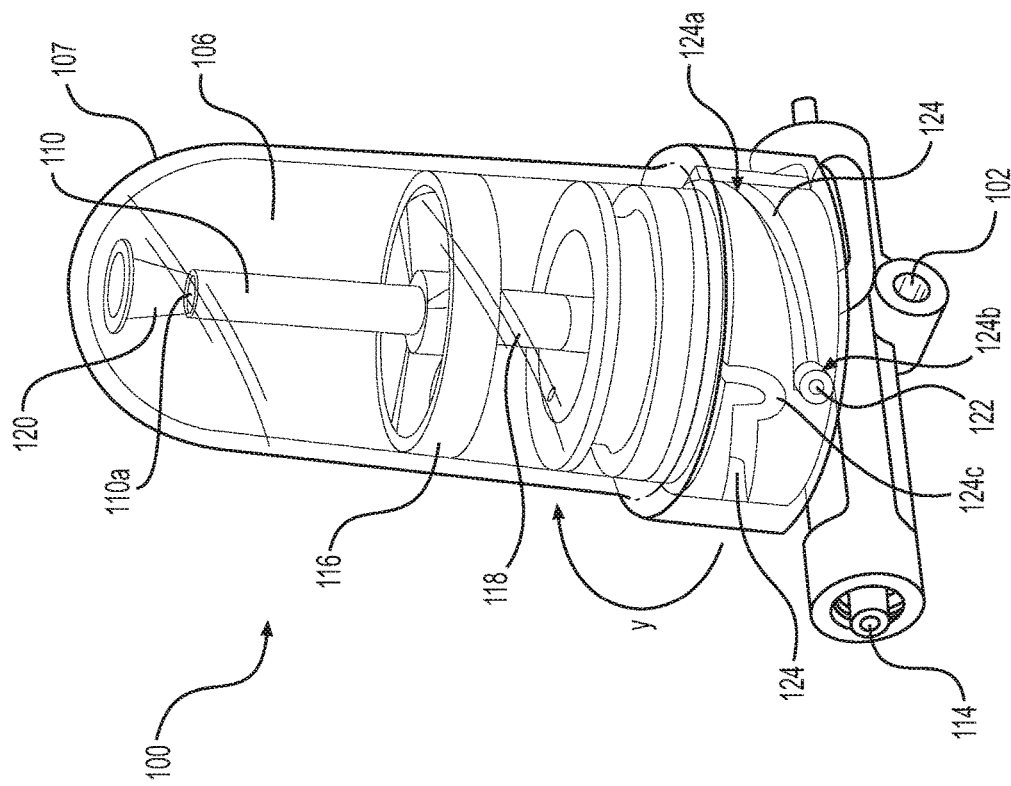

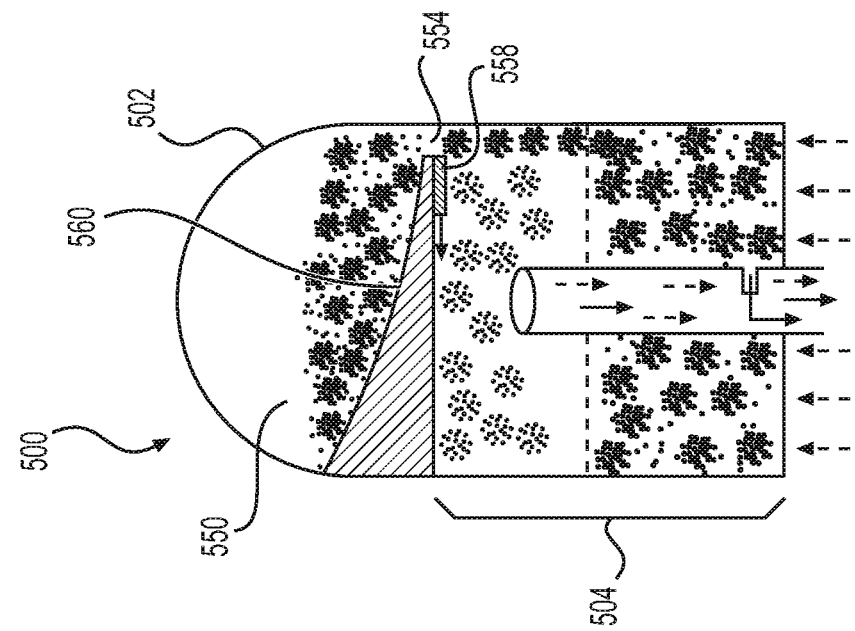
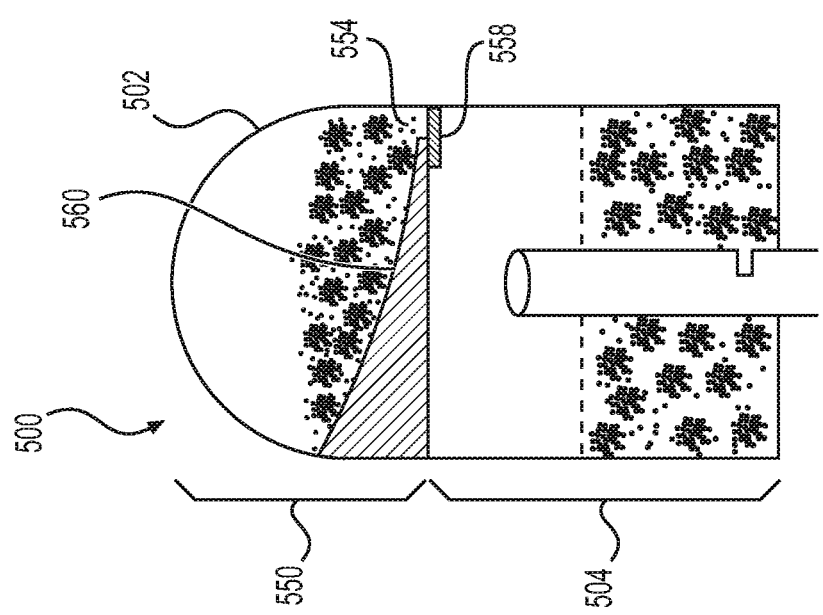

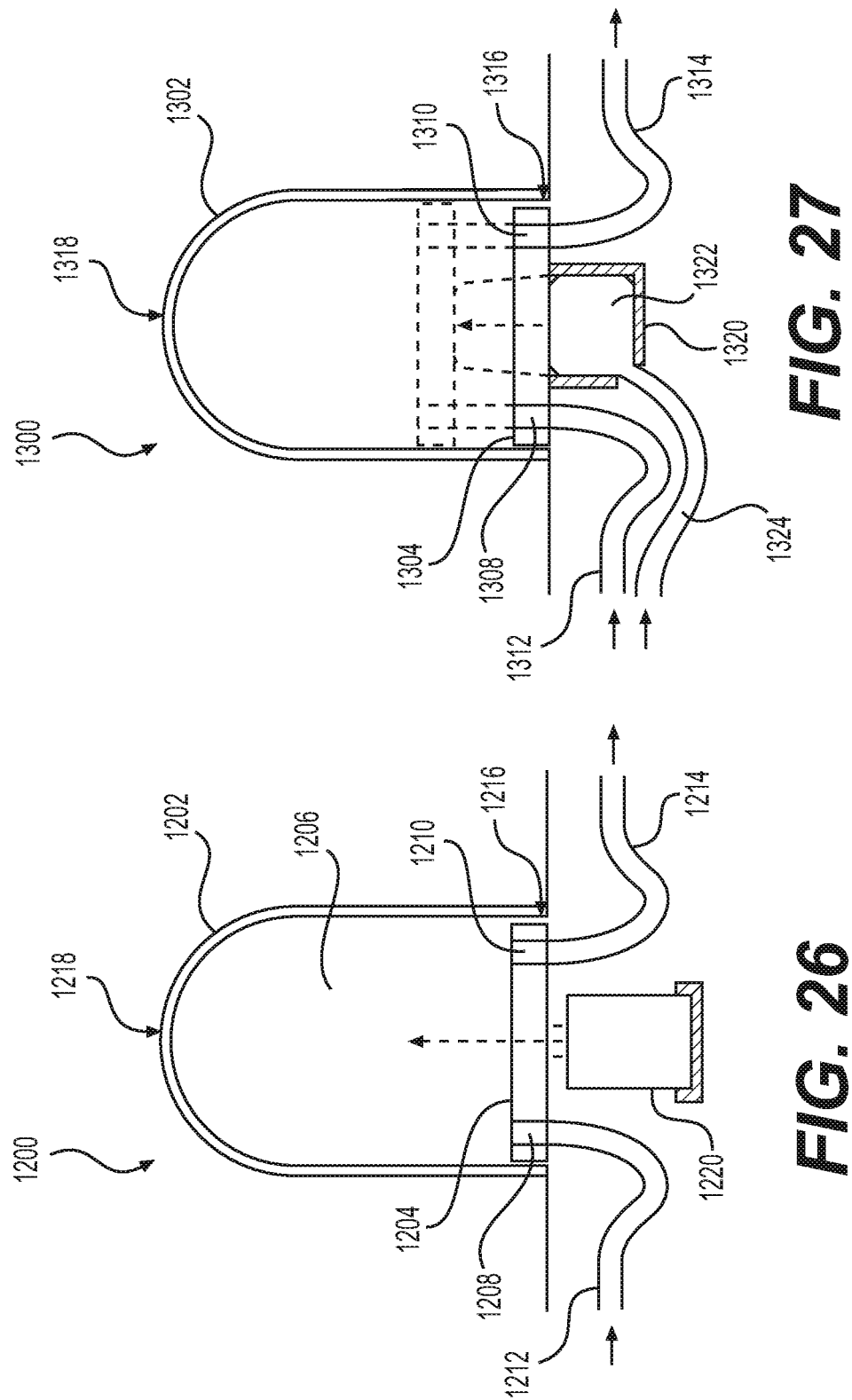

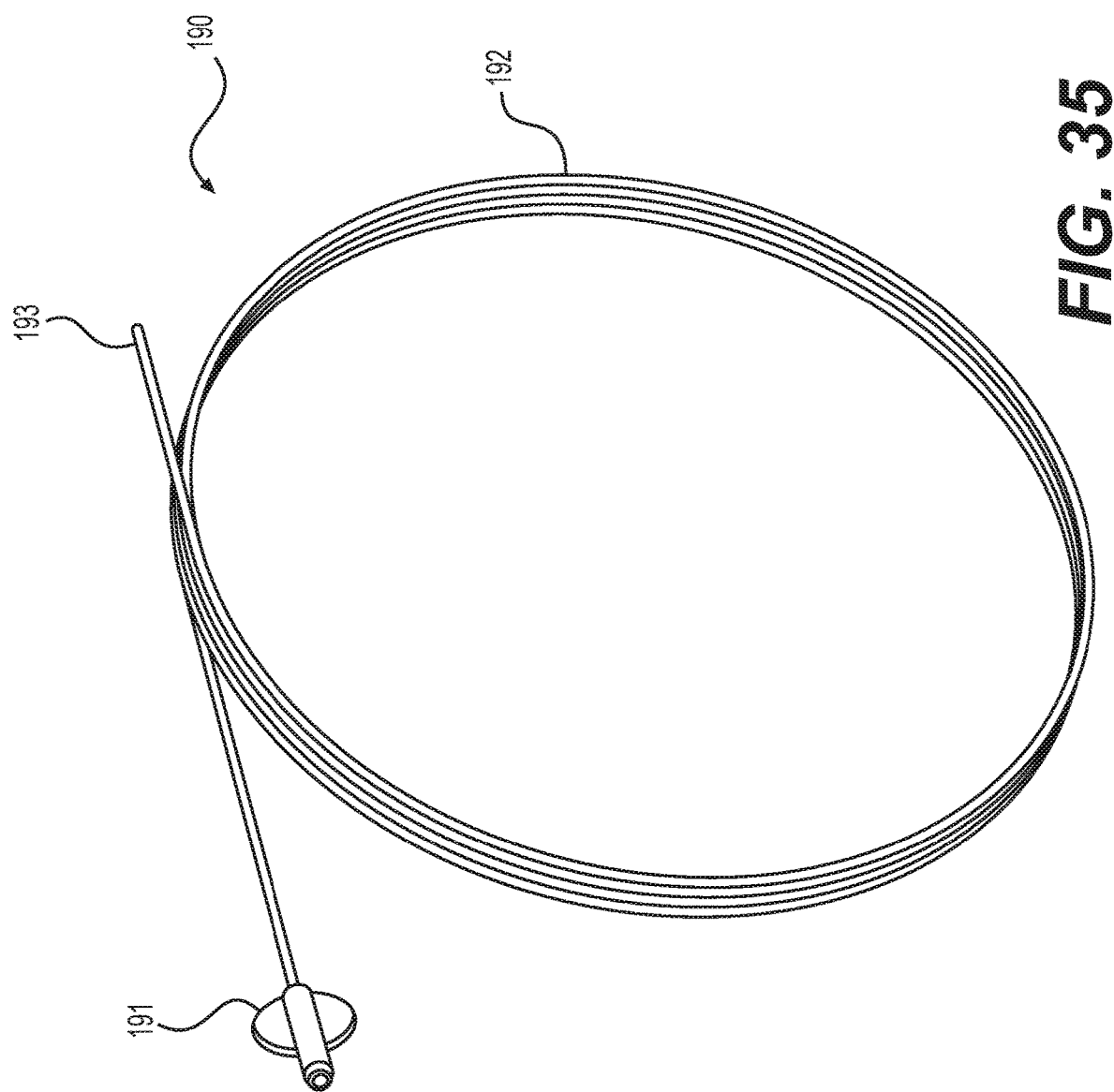

ENDOSCOPIC MEDICAL DEVICE FOR DISPENSING MATERIALS AND METHOD OF USE

CROSS-REFERENCE TO RELATED APPLICATIONS

This application claims the benefit of priority from U.S. Provisional Application No. 62/740,242, filed on Oct. 2, 2018, U.S. Provisional Application No. 62/747,863, filed on Oct. 19, 2018, U.S. Provisional Application No. 62/831,900, filed on Apr. 10, 2019, and U.S. Provisional Application No. 62/848,226, filed on May 15, 2019, each of which is incorporated by reference herein in its entirety.

TECHNICAL FIELD

The present disclosure relates generally to medical systems and devices for delivering pressured fluids, and more particularly, to methods and tools for controlling hemostatic agents and achieving proper tissue contact with the agent at an appropriate pressure and flow rate.

BACKGROUND

Delivery systems and devices are used to supply various materials, such as powders, during medical procedures. These procedures may include supplying powders using fluids, e.g., propellant fluids, within a range of appropriate pressures and/or flow rates. These powders may include hemostatic agents optimally delivered to tissue at an appropriate pressure and/or flow rate, for the particular application.

Conventional endoscope devices for dispensing fluids, powders, and/or reagents in a patient include advancing a catheter to a target site within the patient and subsequently dispensing the fluid. Drawbacks of conventional devices include, for example, clogging of the catheter with the fluid or powder, kinking of the catheter, large variations in the flow rate and pressures of fluids during dispensing, and inconsistency in the material dispensed at the target site. Further, medical fluid delivery systems often require delivering a fluid from a high pressure storage tank to tissue at a lower pressure suitable for the application. The fluid should be applied at a consistent flow rate and at a consistent pressure. In addition, medical fluid delivery systems often require multiple regulators to properly convert the high pressure fluid to a pressure suitable for application to tissue. Multiple regulators inhibit the ability to integrate the regulators with a fluid cylinder, are often costly, and make it difficult to integrate the regulator(s) in a hand-held device for ease of operation. Moreover, conventional regulators include washers or O-rings that generate friction forces with the regulator, making it difficult to dispense fluid at a consistent flow rate and at a consistent pressure. These drawbacks can prevent a proper amount of fluid and/or material from being expelled at a target location, thereby decreasing the accuracy and increasing the time and cost of procedures using these conventional devices. Accordingly, it is desirable to ensure that fluid, powder, and/or reagents are properly and consistently dispensed to the target location. The present disclosure may solve one or more of these problems or other problems in the art. The scope of the disclosure, however, is defined by the attached claims and not the ability to solve a specific problem.

SUMMARY OF THE DISCLOSURE

According to an example, a medical device includes an application device with a first fluid path and a container movable attached to the application device. The container and the application device have a second fluid path therethrough, the container includes an inner chamber that is intermediate proximal and distal portions of the second fluid path, the inner chamber is fluidly isolated from the distal portion of the second fluid path at a first position of the container, and the inner chamber is fluidly coupled to the proximal and distal portions of the second fluid path at a second position of the container. The first fluid path bypasses the container and the passage of fluid through the first fluid path is separately controllable from the passage of fluid through the second fluid path.

The medical device further includes a second container having a propellant fluid and may be configured to be attached to an inlet of the application device.

The application device may further include a locking mechanism for securing the second container to the application device.

The locking mechanism may include a lever pivotally connected to the application device and a piston connected to the lever and contacting the second container, such that in a first position of the lever, the second container may be fluidly decoupled from the application device, and in a second position of the lever, the second container may be fluidly coupled to the application device.

A protrusion may extend from a surface of the piston toward the inlet, and a void may extend into the container from a surface facing the piston. The protrusion may extend into the void to maintain a fixed position of the container with respect to the piston.

The container may include a chamber inlet between the inner chamber and the proximal portion of the second fluid path, and a chamber filter, the filter may be configured to allow a fluid to enter the inner chamber from the proximal portion of the second fluid path, and the filter may be configured to prevent a material disposed in the container from entering the proximal portion of the second fluid path.

The inner chamber may include one or more protrusions extending from a bottom surface of the inner chamber into the inner chamber, and the one or more protrusions may be configured to change a fluid path of the propellant fluid in the inner chamber.

The inner chamber may include a tube having an outlet port, and a sheath disposed about the tube, such that the outlet port may be covered by the sheath when the container is at the first position, and the outlet port ma be exposed from the sheath when the container is at the second position.

The inner chamber may include an attachment member fixedly attached to the sheath and an outer surface of the container, and rotation of the outer surface causes the sheath to move longitudinally on the tube.

The application device may include includes a groove having a first end and a second end, the container may include a cam extending from the outer surface of the container, the cam may be movable within the groove, wherein the cam may be disposed at the first end of the groove when the container is at the first position, and the cam may be disposed at the second end of the groove when the container is at the second position.

The application device may include first and second actuation devices, the first actuation device may be configured to control the propellant fluid in the first fluid path, and the second actuation device my be configured to control the propellant fluid in the second fluid path.

The second fluid path may include a pressure release mechanism configured to release fluid when a pressure of a fluid in the second fluid path is greater than a threshold, and the threshold may be greater than a desired pressure of a fluid at an outlet of the second fluid path.

The pressure release mechanism may include a burst disc and may be disposed in the inner chamber of the container.

The inlet of the application device includes a second pressure release mechanism, and actuation of the second pressure release mechanism may release the propellant fluid from the second container.

A catheter may be attached to an outlet of the distal portion of the second fluid path via a luer connection.

According to another example, a medical device includes an application device having a first fluid path therethrough, and a container movably attached to the application device, the container and the application device have a second fluid path therethrough, the container has an inner chamber having an inlet configured to be fluidly coupled to a proximal portion of the second fluid path and an outlet configured to be fluidly coupled to a distal portion of the second fluid path, the container includes a filter configured to prevent a material provided in the container from entering the proximal portion of the first fluid path, and the inner chamber is fluidly decoupled from the proximal portion of the second fluid path when the container is at a first position, and the inner chamber is fluidly coupled to the proximal and distal portions of the second fluid path when the container is at a second position.

The inner chamber may include a tube having an outlet port, and a sheath disposed about the tube, the outlet port may be covered by the sheath when the container is at the first position, and the outlet port may be exposed from the sheath when the container is at the second position.

The application device may include a groove having a first end and a second end, the container may include a cam extending from an outer surface of the container, the cam may be within the groove, the cam may be disposed at the first end of the groove when the container is at the first position, and the cam may be disposed at the second end of the groove when the container is at the second position.

According to yet another example, a medical device includes an application device having a first fluid path, an inlet, and an outlet, and a container attached to the application device, the container and the application device have a second fluid path therethrough, the container includes an inner chamber between distal and proximal portions of the second fluid path, the inner chamber includes an inflow configured to be fluidly coupled to the proximal portion of the second fluid path and an outflow configured to be fluidly coupled to the distal portion of the second fluid path, and the inner chamber includes at least one protrusion extending into the inner chamber. Fluid in the first fluid path travels from the inlet to the outlet, bypassing the container, and the second fluid path includes a relief valve configured to release a fluid from the second fluid path when a pressure within the second fluid path is greater than a threshold.

The medical device may further include a second container including a propellant fluid, and a locking mechanism, wherein the locking mechanism may include a lever pivotally connected to the application device, a piston connected to the lever and contacting the second container, in a first position of the lever, the second container may be fluidly decoupled from the application device, and in a second position of the lever, the second container may be fluid coupled to the application device.

In yet another aspect, a device for regulating pressure of a fluid includes a body having an input opening for receiving the fluid, an output opening for delivering the fluid, and a chamber in fluid communication with and between the input opening and the output opening. The chamber defines a chamber opening, a flexible membrane contacting the body and having a first surface sealingly covering the chamber opening, and a piston adjacent a second surface of the membrane opposite the first surface for regulating a position of the membrane to regulate pressure of the fluid.

The device may include a pierce pin within the chamber adjacent the input opening and configured to pierce a seal of a containment device configured to contain the fluid.

The body may include a protrusion extending into the chamber and dividing the chamber into a first chamber adjacent the input opening and an annular chamber adjacent the output opening, the device may include an actuator surrounding at least a portion of the protrusion and contacting the first surface of the membrane.

The protrusion may include a first hole fluidly connecting the first chamber with the annular chamber, and a prong of the actuator may extend into the first hole.

The device may include a first spring disposed in the first chamber and configured to push a ball bearing toward the first hole.

The device may include an O-ring provided between the ball bearing and the first hole.

A wall of the actuator may include a second hole in fluid communication with and between the annular chamber and the first chamber.

The device may include a capture member having a first end attached to the body and a second end defining a capture member chamber in which the piston is movably contained, and a cap may be attached to the capture member adjacent the second end to cover an opening of the capture member.

The membrane may be fixed between the body and the capture member.

The device may include a second spring disposed between the piston and the cap and configured to force the piston toward the membrane.

The annular chamber may not include an O-ring.

A fluid path may extend from the input opening, through the first chamber, through the first hole, through the annular chamber, and out the output opening.

The device may include an O-ring disposed in the first chamber adjacent to the first hole, a ball bearing may be disposed in the first chamber adjacent the O-ring on a side opposite the first hole, and a spring may be provided in the first chamber contacting the ball bearing and the pierce pin and configured to urge the ball bearing toward the O-ring.

The device may include a first hole in the protrusion fluidly connecting the first chamber with the annular chamber, an O-ring may be disposed in the first chamber adjacent to the first hole, and a poppet may include a body portion disposed in the first chamber, having an annular ring surrounding the body and adjacent the O-ring on a side opposite the first hole, and the poppet may include an elongated member extending from the body portion, perpendicular to the annular ring, through the O-ring and a hole, and contacting the body.

According to another aspect, a delivery system for dispensing fluid includes a containment device configured to contain the fluid, and an application device connected to the containment device and configured to dispense the fluid, the application device comprising an inlet configured to be connected to the containment device to receive the fluid from the containment device, and a regulator in fluid communication with the inlet and configured to regulate the release of the fluid. The regulator includes a body having an input opening for receiving the fluid, an output opening for delivering the fluid, and a chamber in fluid communication with the input opening and the output opening, the chamber defines a chamber opening, a flexible membrane contacting the body and having a first surface sealingly covering the chamber opening, and a piston adjacent a second surface of the membrane opposite the first surface and configured to regulate a position of the membrane to regulate pressure of the fluid.

The system may include a piston chamber defined between and within annular walls of the piston, and a spring may be disposed in the piston chamber and configured to push the piston against the membrane.

The system may include an actuating device, and the fluid configured to be dispensed from the application device upon actuation of the actuating device In yet another aspect, a method for controlling a fluid delivery to a body of a patient includes moving a piston and a flexible membrane of a regulator toward an input opening of the regulator, the input opening receiving the fluid from a containment device, contacting an actuator of the regulator with the membrane to open a fluid pathway from the input opening to an output opening of the regulator, and causing a fluid to be released.

The method may include compressing a spring adjacent the input opening; and breaking a fluid seal between the input opening and the output to open the fluid pathway between the input opening and the output opening of the regulator.

According to another aspect, a device configured to regulate pressure of a fluid includes a first body having an input opening for receiving the fluid, an output opening for delivering the fluid, wherein the first body includes a protrusion extending into the chamber and dividing the chamber into a first chamber adjacent the input opening and a second chamber adjacent the output opening, and wherein the protrusion includes a hole fluidly connecting the first chamber and the second chamber, an X-ring disposed in the first chamber adjacent to the hole, and a second body disposed in the first chamber adjacent the X-ring on a side opposite the hole.

The protrusion may have a first surface and a second surface approximately perpendicular to the first surface, wherein each of the first surface and the second surface may face the first chamber.

The X-ring may contact two separated portions of at least one of the first surface and the second surface.

The X-ring may contact two separated portions of each of the first surface and the second surface.

The X-ring may include four protrusions, and the second body may be configured to contact one of the four protrusions in at least one state of the device.

The X-ring and the second body may be configured to prevent fluid from passing through the hole in at least one state of the device.

The device may further include a first spring disposed in the first chamber and configured to push the second body toward the hole.

A fluid path may extend from the input opening, through the first chamber, through the hole, through the second chamber, and out the output opening.

The second chamber may define a chamber opening, and the device may further include a flexible membrane contacting the body and having a first surface sealingly covering the chamber opening.

The device may further include an actuator surrounding at least a portion of the protrusion and contacting the first surface of the membrane.

The device may further include a piston adjacent a second surface of the membrane opposite the first surface and configured to regulate a position of the membrane.

The device may further include a second spring disposed between the piston and a cap and configured to force the piston toward the membrane.

The second body may include rubber.

The X-ring may include silicone.

Properties of the second body and X-ring may be such that the second body and X-ring are compatible with temperatures of −50 C.

According to another aspect, a device is configured to regulate pressure of a fluid, the device includes a first body having an input opening for receiving the fluid, an output opening for delivering the fluid, and a chamber between the input opening and the output opening, wherein the chamber defines a chamber opening, a flexible membrane contacting the first body and having a first surface sealingly covering the chamber opening, an X-ring disposed in the chamber, a second body disposed in the chamber adjacent the X-ring, and a spring provided in the chambers contacting the second body and configured to urge the second body toward the X-ring.

The chamber may at least partially defined by a first surface and a second surface, and wherein the X-ring may contact two separated portions of at least one of the first surface and the second surface.

The X-ring may include four protrusions, and the second body may be configured to contact one of the four protrusions in at least one state of the device.

According to an aspect, a device may be configured to regulate pressure of a fluid, and the device may include a first body having an input opening for receiving the fluid, an output opening for delivering the fluid, and a chamber in fluid communication with and between the input opening and the output opening, an X-ring disposed in the chamber, a second body disposed in the chamber adjacent the X-ring, a first spring provided in the chamber, contacting the second body, and configured to urge the second body in a first direction, toward the X-ring, a piston, and a second spring configured to push the piston in a second direction, opposite the first direction, toward the X-ring.

The chamber may at least partially defined by a first surface and a second surface, and wherein the X-ring may contact two separated portions of at least one of the first surface and the second surface.

According to another aspect, a device for fluidizing and delivering a powdered agent comprises a canister extending longitudinally from a first end to a second end and defining an interior space within which a powdered agent is received, an inlet coupleable to a gas source for supplying gas to the interior space to fluidize the powdered agent received therewithin to create a fluidized mixture, an outlet via which the gas mixture is delivered to a target area for treatment, a tube extending from a first end in communication with the outlet to a second end extending into the interior space, the tube including a slot extending through a wall thereof so that gas mixture is passable from the interior space through the outlet via the second end and the slot, and a door movably coupled to the tube so that the door is movable over the slot to control a size of the slot open to the interior space of the canister.

In an aspect, the door may be configured as an overtube movably mounted over the tube.

In an aspect, the device may further comprise a stabilizing ring extending radially outward from the overtube to an interior surface of the canister to fix the tube relative to the canister.

In an aspect, the canister may be rotatable relative to the tube to move the overtube longitudinally relative to the tube and control the size of the slot open to the interior space.

In an aspect, the device may further comprise a lid coupleable to the canister to enclose the interior space, the inlet and the outlet configured as openings extending through the lid.

In an aspect, the device may further comprise a delivery catheter coupleable to the outlet, the delivery catheter sized and shaped to be inserted through a working channel of an endoscope to the target area.

The present aspects are also directed to a device for fluidizing and delivering a powdered agent, comprising a canister extending longitudinally from a first end to a second end and including a first interior space within which a powdered agent is received, a first inlet coupleable to a gas source for supplying gas to the interior space to fluidize the powdered agent received therewithin to create a fluidized mixture, an outlet via which the gas mixture is delivered to a target area for treatment from the first interior space, and a filler chamber in communication with the first interior space via a filler inlet, the filler chamber containing a filler material passable from the filler chamber to the first interior space to maintain a substantially constant volume of material therein, wherein the material includes at least one of the powdered agent and the filler material.

In an aspect, the filler material may include one of mock particles, beads, bounce balls, and a foam material.

In an aspect, the filler material may be sized, shaped and configured so that the filler material cannot be passed through the outlet.

In an aspect, the filler chamber may be supplied with a gas to drive the filler material from the filler chamber into the first interior space.

In an aspect, the filler chamber may be configured as a second interior space defined via the canister.

In an aspect, the second interior space may include an angled surface directing the filler material to the filler inlet.

In an aspect, the filler material may be additional powdered agent.

In an aspect, the device may further comprise a door movable relative to the filler inlet between a first configuration, in which the door covers the filler inlet, to a second position, in which the door opens the filler inlet to permit filler material to pass therethrough from the filler chamber to the first interior space via gravity.

In an aspect, the device may further comprise a turbine connected to a paddle housed within the filler inlet, the turbine driven by a flow of gas so that, when a flow of gas is received within a flow path housing the turbine, the turbine rotates to correspondingly rotate the paddle so that filler material within the filler chamber is actively driven therefrom and into the first interior space.

The present aspects are also directed to a method, comprising supplying a gas to an interior space within a canister within which a powdered agent is received to fluidize the powdered agent, forming a fluidized mixture and delivering the fluidized mixture to a target area within a patient body via a delivery catheter inserted through a working channel of an endoscope to the target area, wherein during delivery of the fluidized mixture, a door movably mounted over the tube is moved relative to a slot extending through a wall of a tube extending into the interior space of the canister in communication with the delivery catheter, to control a size or a portion of the slot exposed to the interior space.

The present aspects are also directed to a device for fluidizing and delivering a powdered agent, comprising a canister extending longitudinally from a first end to a second end and defining an interior space within which a powdered agent is received, an inlet coupleable to a gas source for supplying gas to the interior space to fluidize the powdered agent received therewithin to create a fluidized mixture, an outlet via which the gas mixture is delivered to a target area for treatment, and a piston movably coupled to the canister, the piston movable from an initial configuration, in which the piston is coupled to the first end of the canister, toward the second end of the canister to reduce a volume of the interior space as a volume of the powdered agent is reduced during delivery of the fluidized mixture to the target area.

In an aspect, each of the inlet and the outlet may extend through a portion of the piston.

In an aspect, the outlet may be coupleable to a delivery catheter sized and shaped to be inserted through a working channel of an endoscope to the target area.

In an aspect, the piston may be movable via one of a pneumatic cylinder and motor.

In an aspect, the device may further comprise a chamber connected to the first end on the canister on a side of the piston opposing the interior space of the canister, the chamber housing an expandable member which is configured to receive gas during delivery of the fluidized mixture so that the expandable mixture expands to move the piston toward the second end of the canister.

In an aspect, the expandable member may be configured to be connected to the gas source via a connecting member including a one way valve which permits a flow of gas into the expandable member while preventing a flow of gas out of the expandable member.

In an aspect, the device may further comprise a bypass connected to the first end of the canister and coupled to the piston via a threaded rod, the bypass housing a turbine connected to the threaded rod and being configured to receive a flow of gas therethrough so that, when gas flows through the bypass during delivery of the fluidized mixture, the turbine and threaded rod rotate to move the piston toward the second end of the canister.

The present aspects are directed to a device for fluidizing and delivering a powdered agent, comprising a canister extending longitudinally from a first end to a second end and including a first interior space within which a powdered agent is received, an inlet coupleable to a gas source for supplying gas to the interior space to fluidize the powdered agent received therewithin to create a fluidized mixture, an outlet via which the gas mixture is delivered to a target area for treatment, and an expandable member movable between an initial biased configuration and an expanded configuration in which the expandable member is deformed so that a portion of the expandable member extends into the first interior space to reduce a volume thereof as a volume of the powdered agent therein is reduced during delivery of the fluidized mixture to the target area.

In an aspect, the canister may further include a second interior space configured to receive a gas therein during delivery of the fluidized mixture to the target area.

In an aspect, the first and second interior spaces may be separated from one another via an expandable member, a pressure differential between the first and second interior spaces causing the expandable member to deform into the first interior space.

In an aspect, the expandable member may be a diaphragm.

In an aspect, the first interior space may be defined via an interior wall of the expandable member and the second interior space may be defined via an exterior wall of the expandable member and an interior surface of the canister.

In an aspect, the expandable member may be substantially cylindrically shaped.

In an aspect, the expandable member may extend from the first end of the canister to the second end of the canister.

In an aspect, the expandable member may be a balloon housed within the canister and configured to receive a gas therewithin so that, as the balloon is inflated, the balloon fills the first interior space.

The present aspects are also directed to a method, comprising supplying a gas to an interior space within a canister within which a powdered agent is received to fluidize the powdered agent, forming a fluidized mixture, and delivering the fluidized mixture to a target area within a patient body via a delivery catheter inserted through a working channel of an endoscope to the target area, wherein during delivery of the fluidized mixture, a volume of the interior space of the canister is reduced to correspond to a reduction in volume of the powdered agent so that a rate of delivery of the fluidized mixture remains substantially constant.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 14A and 14B are perspective views of the chamber of FIG. 13;

FIG. 22 shows a schematic view of a device according to yet another embodiment of the present disclosure, in a first configuration;

FIG. 23 shows a schematic view of the device of FIG. 22, in a second configuration;

FIG. 26 shows a schematic view of a device according to an embodiment of the present disclosure;

FIG. 27 shows a schematic view of a device according to an alternate embodiment of the present disclosure;

FIG. 35 is a perspective view of a catheter of the medical device of FIG. 1.

DETAILED DESCRIPTION

Figure 1:
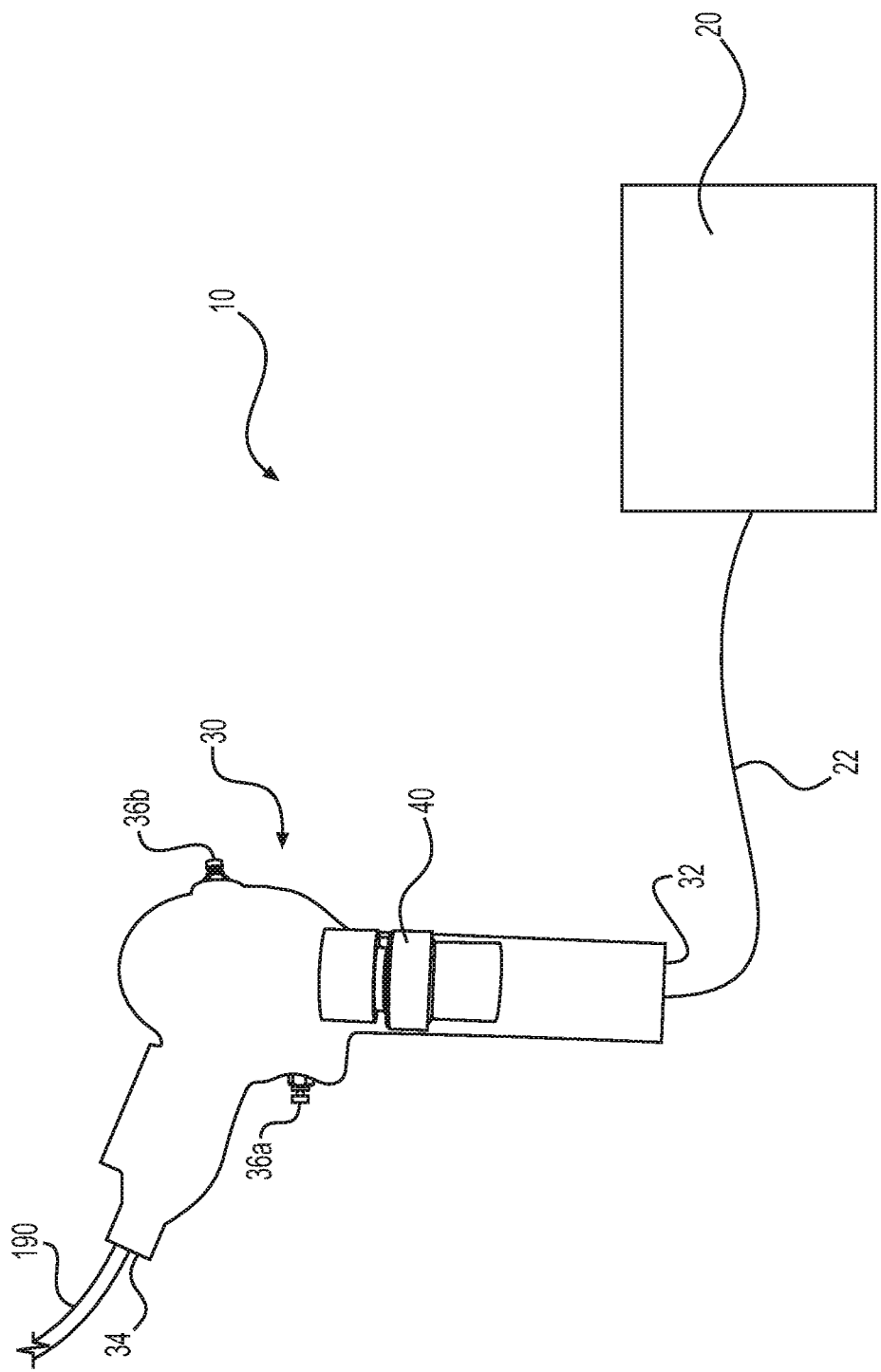
FIG. 1 is a perspective view of a medical system according to an embodiment.

The present disclosure is now described with reference to exemplary medical devices that may be used in dispensing materials. However, it should be noted that reference to any particular procedure is provided only for convenience and not intended to limit the disclosure. A person of ordinary skill in the art would recognize that the concepts underlying the disclosed devices and application methods may be utilized in any suitable procedure, medical or otherwise. The present disclosure may be understood with reference to the following description and the appended drawings, wherein like elements are referred to with the same reference numerals.

For ease of description, portions/regions/ends of a device and/or its components are referred to as proximal and distal ends/regions. It should be noted that the term "proximal," as it relates to an application device, is intended to refer to ends/regions closer to an inlet of a propellant gas to the application device (e.g., at a location of the application device where the propellant gas is released from a containment device into the application device), and the term "distal," as it relates to an application device, is used herein to refer to ends/regions where the propellant gas and/or any material is released from the application device to a target area or, if a catheter is attached to the application device, from the catheter to the target area. Similarly, extends "distally" indicates that a component extends in a distal direction, and extends "proximally" indicates that a component extends in a proximal direction. Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Referring to FIG. 1, a medical system, e.g., a delivery system, 10 according to an embodiment is shown. Delivery system 10 includes a containment device 20 and an application device 30, e.g., a hand-held device, connected thereto by a conduit 22. As will be described herein, application device 30 may be attached directly to, or otherwise be integrated with, containment device 20 without conduit 22 therebetween (see e.g., FIG. 2). As further shown in FIGS. 1-3, application device 30 includes an inlet 32, an outlet 34, and actuating devices 36a, 36b. According to an example, outlet 34 may be a male or a female luer fitting, but is not limited to this configuration. As will be explained herein, the propellant fluid and/or any additional material is expelled into catheter 190 via outlet 34, allowing a user to output the propellant fluid at a desired location. Examples of apparatuses for delivering powdered agents are found in U.S. patent application Ser. No. 16/259,024, entitled "Apparatuses and Methods for Delivering Powdered Agents," and filed on Jan. 28, 2019, the complete disclosure of which is incorporated by reference herein.

With reference to FIG. 1, containment device 20 is configured to contain a fluid, such as a gas, e.g., carbon dioxide or any other gas of fluid known in the art. While shown as a box, containment device 20 may be any shape, such as a torpedo-shape (see e.g., FIG. 2), a sphere, or any other shape known in the art for containing gas. For example, containment device 20 could be a carbon dioxide tank or cylinder typically formed in medical settings, such as a hospital. Containment device 20 includes one or more outer walls defining one or more inner chambers (not shown), the inner chamber(s) configured to contain the fluid. The walls of containment device 20 may be formed of any material suitable for containing the fluid, such as but not limited to a metal alloy, a ceramic, or other material known in the art. The fluid contained in the inner chamber of containment device 20 may be under pressure. Accordingly, the walls are formed of a material and/or a thickness suitable to contain the fluid at a pressure of, for example, at least approximately 1000 pounds per square inch (PSI), or approximately 850 PSI. For example, gases which may be contained in containment device 20 include carbon dioxide ($CO_2$) having a vapor pressure of approximately 2,000-8,000 kPa at typical device temperatures, or nitrogen (N2) having a vapor pressure less than 40 MPa at typical device temperatures. It will be understood that these gases are examples and are not limiting to the types of gases contained in containment device 20.

With continued reference to FIG. 1, application device 30 is attached to containment device 20 via conduit 22. Conduit 22 may supply fluid under pressure from containment device 20 to application device 30. As will be described in greater detail herein, actuation of actuating devices 36a, 36b causes fluid to move from containment device 20, through conduit 22, and to application device 30, allowing a user to output the fluid at a desired location via catheter 190. Conduit 22 may be made of any material, for example reinforced rubber or a suitable plastic, that allows conduit 22 to withstand the pressures of the fluid, while simultaneously allowing for unrestricted movement of conduit 22. Conduit 22 may be attached to containment device 20 and application device 30 by any attachment device, including but not limited to screw-type connectors, pressure washer adapters, or any other device known in the art.

Figure 2:
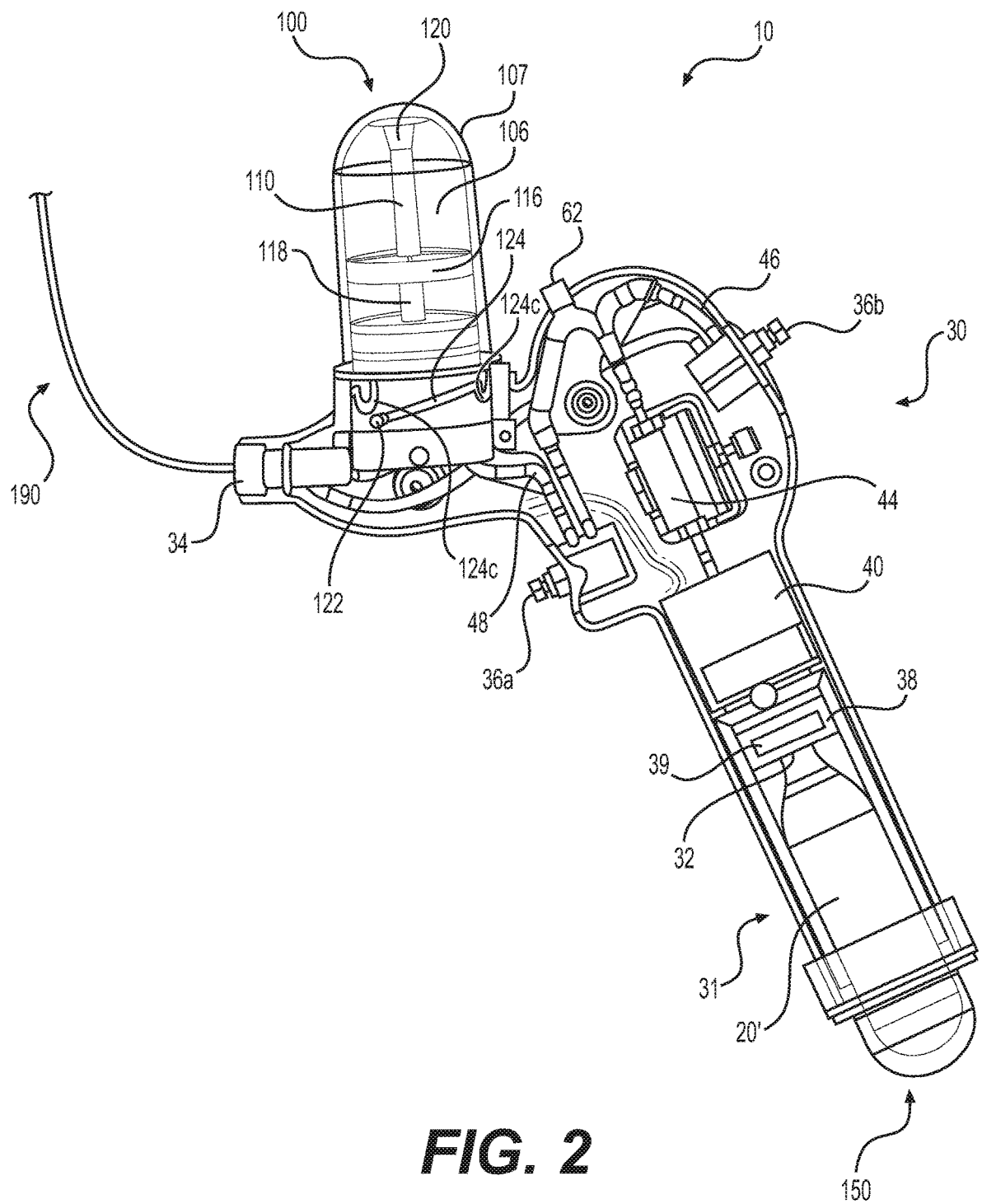
FIG. 2 is a cross-section of an applicator handle of the medical system of FIG. 1.

According to another embodiment, application device 30 may be connected directly to containment device 20', without any intervening structure, as shown in FIG. 2. For example, inlet 32 may be connected directly to an output, such as a protuberance of containment device 20' using a threaded connection, pressure washer adapter, or the like. The protuberance of containment device 20' may extend into inlet 32 of application device 30 and connect, directly or via an intervening structure, e.g., a lumen, to a regulator 40. Directly connecting application device 30 to containment device 20' may be suitable for, e.g., a small-volume containment device 20' containing approximately 5 g to 75 g of compressed gas, or preferably approximately 12 g to 40 g of compressed gas, to allow for greater portability of delivery system 10.

Referring to FIG. 1, actuation of actuating devices 36a, 36b of application device 30 causes the fluid to exit delivery system 10 through outlet 34 of application device 30. It will be understood that only one actuating device 36a, 36b may need to be actuated in some embodiments. Alternatively, or additionally, a plurality of actuating devices 36a, 36b may be simultaneously actuated to release fluid as, for example, a safety precaution. As will be described herein, actuation of actuating device 36a, 36b releases a buildup of pressure within delivery system 10, causing regulator 40 to release fluid from containment device 20' at a predetermined pressure. Application device 30 may be, e.g., a handle such as a garden-hose handle or other pistol-like configuration. Actuating device 36a, 36b may be any push button, trigger mechanism, or other device that, when actuated, opens a valve and releases fluid, as will be described in greater detail herein.

With reference to FIG. 2, application device 30 is attached directly to a torpedo-shaped containment device 20', without any intervening structure. Containment device 20' may be attached to inlet 32 of application device 30 by any attachment device 38, including but not limited to screw-type connectors, pressure washer adapters, a pierce pin and seal arrangement, or any other device known in the art. It will also be understood that attachment device 38, or any other device for attaching containment device 20' to application device 30, may include an actuator 39 (e.g., a tab, a button, etc.) for opening or rupturing a burst disc or pressure release valve attached to containment device 20' and/or application device 30. Actuator 39 may be actuated at an end of a procedure to vent any remaining propellant fluid from containment device 30. An alert, such as a tactile or an audible alert, may be generated when containment device 20' is attached to application device 30. Alternatively, containment device 20' may be attached to application device 30 by a locking mechanism 50, as will be described in greater detail below. Additionally, a cap 150 may be attached by screw fit, snap fit, or any other attachment mechanism to a handle 31 of application device 30. For example, cap 150 may be attached to an end of handle 31 opposite attachment device 38. Cap 150 may provide additional support to secure containment device 20' to application device 30.

As discussed above, one or more regulators 40 may assist in regulating an amount of propellant fluid released from containment device 20' at a specific pressure, as will be described in greater detail with reference to FIGS. 5-11B. For example, regulator 40 may be a dual stage regulator, or regulator 40 may be two single stage regulators, such as two piston regulators, aligned in series. As will be discussed in greater detail below, regulator 40 may include a pierce pin 670 (see FIG. 6A) to pierce a seal of containment device 20' when containment device 20' is attached to application device 30. Alternatively, a separate device, such as a pierce pin or other mechanism for rupturing a seal of containment device 20', may be provided at inlet 32 of application device 30. Further, inlet 32 may provide an all-or-nothing scenario in which the containment device 20' is completely attached or completely detached from application device 30 using, e.g., gaskets or washers (not shown) to prevent leakage at inlet 32. A propellant fluid pressure may further be adjusted by a membrane regulator 44 provided in series after regulator 40. The combination of regulator 40 and membrane regulator 44 may reduce the pressure of gas from containment device 20' to an acceptable outlet pressure, i.e., a pressure of the gas and any material at outlet 34. A pressure of a gas within delivery system 10, after regulators 40, 44, and at a target area in a patient, may be predetermined, based on the tissue to which the gas and material is being dispensed. An acceptable pressure at outlet 34 may be approximately plus or minus 40% deviation from the target pressure, more preferably approximately plus or minus 25% deviation from the target pressure. For example, regulator 40 may reduce inlet pressure of the dispensing propellant fluid to approximately 50-150 PSI, and membrane regulator 44 may subsequently reduce the propellant fluid to approximately 20-50 PSI. According to an example, regulator 40 and membrane regulator 44 reduce the propellant fluid to the desired output pressure of the propellant fluid based on a predetermined setting during manufacturing. Alternatively, or additionally, one or both of regulator 40 and membrane regulator 44 may include a mechanism (not shown) for adjusting the pressure of the propellant fluid output from each regulator. Further, the pressure of the propellant fluid at an outlet of membrane regulator 44 may be approximately equal to the pressure of the propellant fluid at outlet 34. Alternatively, the pressure of the propellant fluid at outlet 34 may be different from the pressure of the propellant fluid at the outlet of membrane regulator 44.

Figure 3:
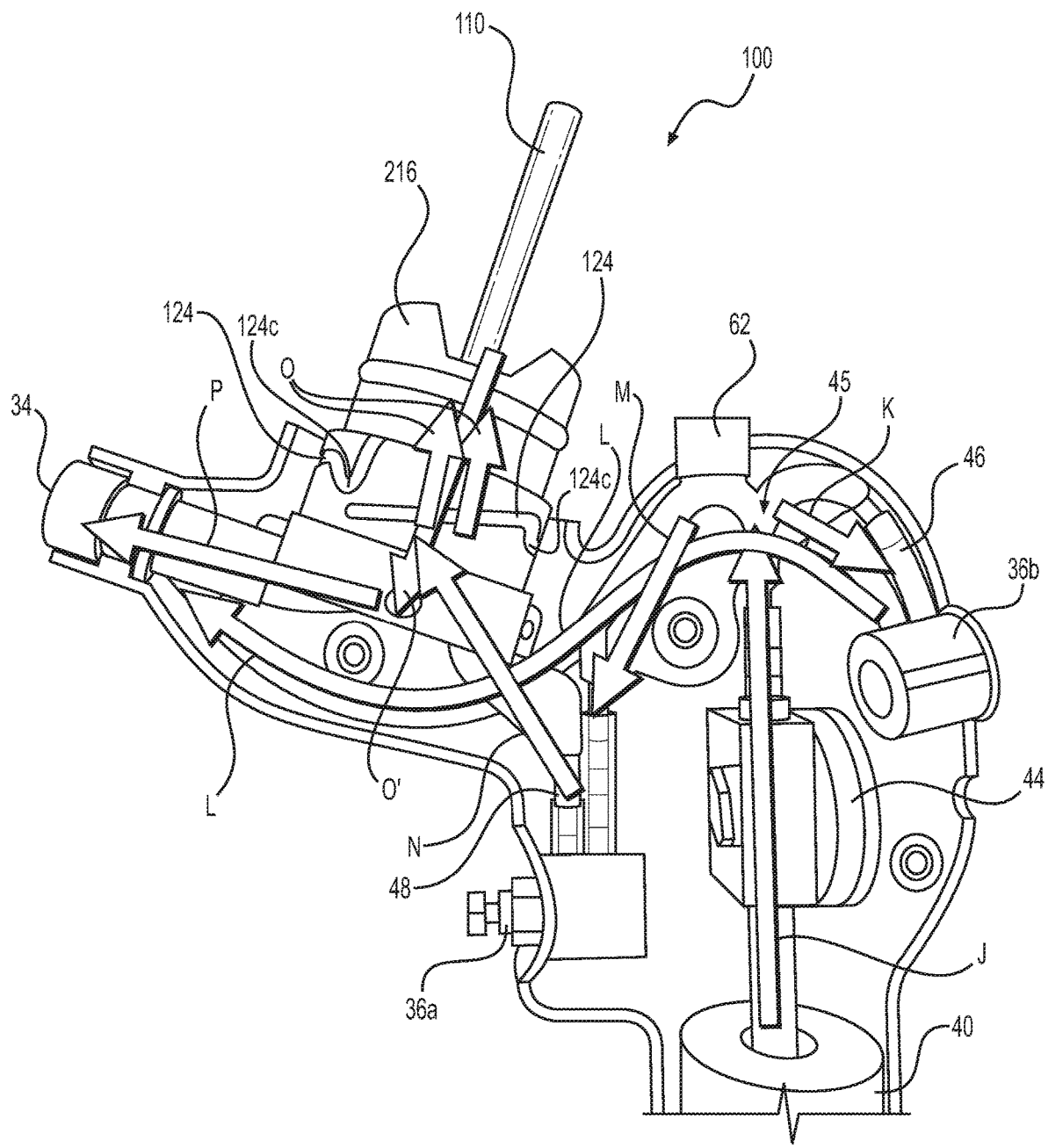
FIG. 3 is a perspective view of a flow path of the medical system of FIG. 1.

With reference to FIGS. 2 and 3, two fluid paths diverge at a Y-connector 45, which is just distal to an outlet of membrane regulator 44. A first fluid path 46, which may be a purge path and which may bypass a material-containing container, may be controlled by actuating device 36b. For example, first fluid path 46 may bypass a container 100 to release propellant fluid from membrane regulator 44 directly to outlet 34. First fluid path 46 allows propellant fluid from containment device 20' to purge catheter 190 to remove any debris provided therein. A second fluid path 48 may be controlled by actuating device 36a to direct propellant fluid from membrane regulator 44, through container 100, to outlet 34. Second fluid path 48 allows the propellant fluid to enter container 100, which contains powder or other material to be dispensed as discussed in greater detail below, mix with the powder or material contained therein, and transport the mixture through outlet 34 to a target site, via catheter 190. According to an example, propellant fluid travels through first fluid path 46 at approximately 8-12 standard liters per minute (SLPM), or preferably approximately 10 SLPM. Alternatively, propellant fluid may travel through first fluid path 46 at approximately 4-6 SLPM, or preferably approximately 5 SLPM. Propellant fluid travels through second fluid path 48 at approximately 0.5-4.5 SLPM, or preferably approximately 2 SLPM.

Figure 12:
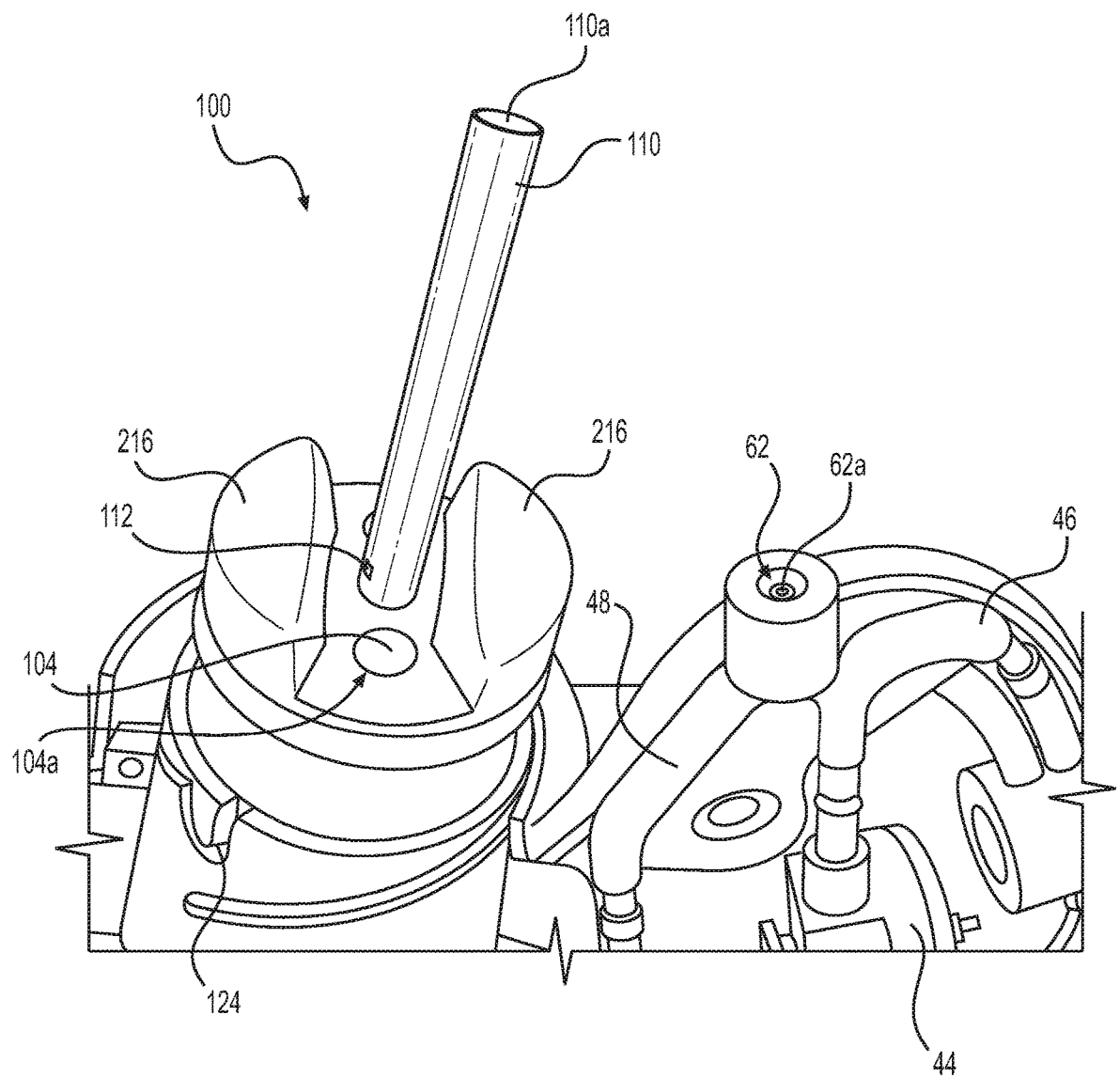
FIG. 12 is a perspective view of a portion of the medical system of FIG. 1.

Flow paths of propellant fluid, including fluid paths 46 and 48, are shown in FIG. 3. Propellant fluid flows along first pathway J from regulator 40, through membrane regulator 44, and to a junction of first fluid path 46 and second fluid path 48. At the junction of first fluid path 46 and second fluid path 48, pathway J splits into second pathway K and third pathway M. Second pathway K travels along first fluid path 46 to second actuating device 36b. When actuated, second actuating device 36b dispenses dispensing fluid along fourth pathway L (distal to second actuating device 36b), which terminates at outlet 34. First pathway J, second pathway K, and fourth pathway L form first fluid path 46. Alternatively, propellant fluid from first pathway J may follow third pathway M to first actuating device 36a. When actuated, first actuating device 36a dispenses propellant fluid along fifth pathway N (distal to first actuating device 36a) and each of a plurality of sixth pathways O, which provide propellant fluid to container 100 through filter holes 104a (see FIG. 12). Propellant fluid mixes with material provided in container 100 (a housing 107 of container 100, as shown in FIG. 12, is not shown in FIG. 3 for ease of understanding), as will be described herein, and the mixture travels from container 100 along seventh pathway O', which leads from an outlet (described below) of container 100 to a chamber outlet 114 (see FIGS. 14A and 14B), and eighth pathway P, which leads along chamber outlet 114 to outlet 34. First, third, fifth, sixth, seventh, and eighth pathways J, M, N, O, O', P, respectively, form second fluid path 48. Further, first, third, and fifth pathways J, M, and N form a proximal portion of second fluid path 48, eighth pathway P forms a distal portion of second fluid path 48, and sixth and seventh pathways O, O' form an intermediate portion of second fluid path 48. As shown in FIG. 3, first-eighth pathways J-P are tubes or lumen extending through and/or interconnecting elements of medical device 10. These tubes and/or lumen may be formed of medical grade plastic, metal, ceramic, or any other suitable material for moving propellant fluid and/or material throughout medical device 10.

Figure 4:
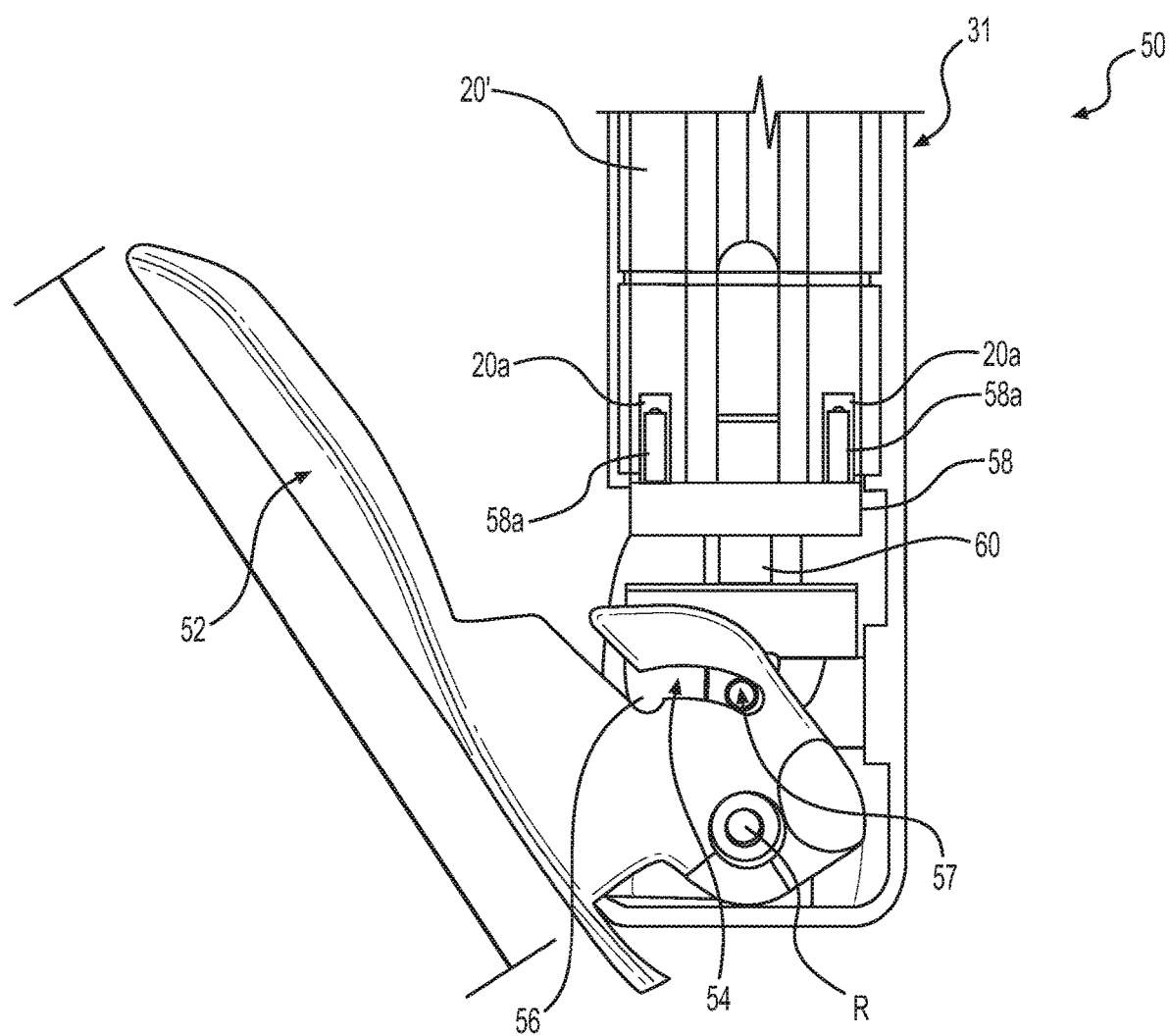
FIG. 4 is a perspective view of a locking mechanism of the medical system of FIG. 1.

A locking mechanism 50 for securing containment device 20' will be described with reference to FIG. 4. Locking mechanism 50 may replace cap 150 in FIG. 2. Locking mechanism 50 includes a lever 52 pivotally connected to handle 31 of application device 30 at pivot axis R. Lever 52 includes a cam path 54 defining a curved path, and a locking notch 56 at one end of the cam path 54. A pin 57 extends generally perpendicular from a shaft 60, and pin 57 rides along cam path 54 between locking notch 56 and an opposite end of cam path 54. Shaft 60 extends along a longitudinal axis of handle 31 and includes a piston head 58 attached to an end of shaft 60 opposite pin 57. As shown in FIG. 4, a bottom surface of containment device 20' sits on a top surface of piston 58. Lever 52 is angled with respect to handle 31 when locking mechanism 50 is unlocked, e.g., when introducing or removing containment device 20' from handle 31. Lever 52 rotates about pivot axis R, causing pin 57 to ride in cam path 54 from the first end to the locking notch 56. Pin 57 locks in locking notch 56 when lever 52 is substantially parallel to handle 31. The curvature of cam path 56 forces shaft 60 and piston 58 against the bottom surface of containment device 20', moving containment device 20' toward a pierce pin (not shown, see, e.g., pierce pin 670 in FIG. 6A), causing the pierce pin to rupture a seal (not shown) on containment device 20' and fluidly connect containment device 20' to application device 30. In one example, cavities 20a extend into a bottom surface of containment device 20' and receive protrusions 58a extending from a topmost surface of piston 58, thereby removably connecting containment device 20' and piston 58, and preventing containment device 20' from slipping with respect to piston 58. Alternatively, or additionally, the topmost surface of piston 58 and/or the bottommost surface of containment device 20' may include a textured surface, such as abrasions, knurls, cavities, slots, or any other friction-increasing coating to increase the friction between containment device 20' and piston 58 to maintain a relative position between containment device 20' and piston 58. This configuration may aid containment device 20' to be properly urged toward the pierce pin and to properly seal containment device 20' to application device 30.

Figure 5:
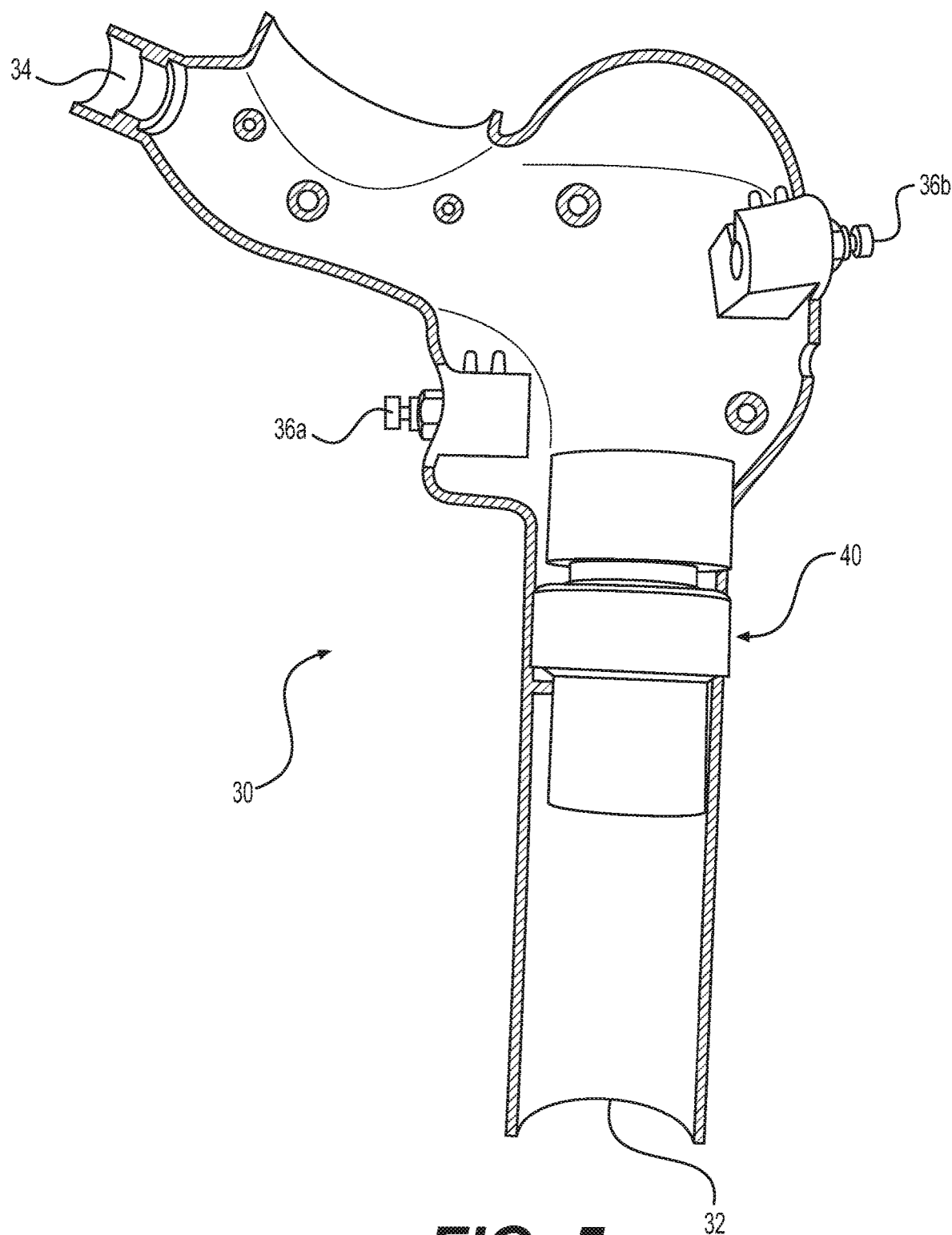
FIG. 5 is a cross-section of the applicator handle of FIG. 3 including a regulator according to an embodiment.

Referring to FIG. 5, many elements of application device 30 are stripped away to show a position of regulator 40. It will be understood that the position of regulator 40 within application device 30 is only meant for example, and is not limited to that shown in FIG. 5.

Figure 6A:
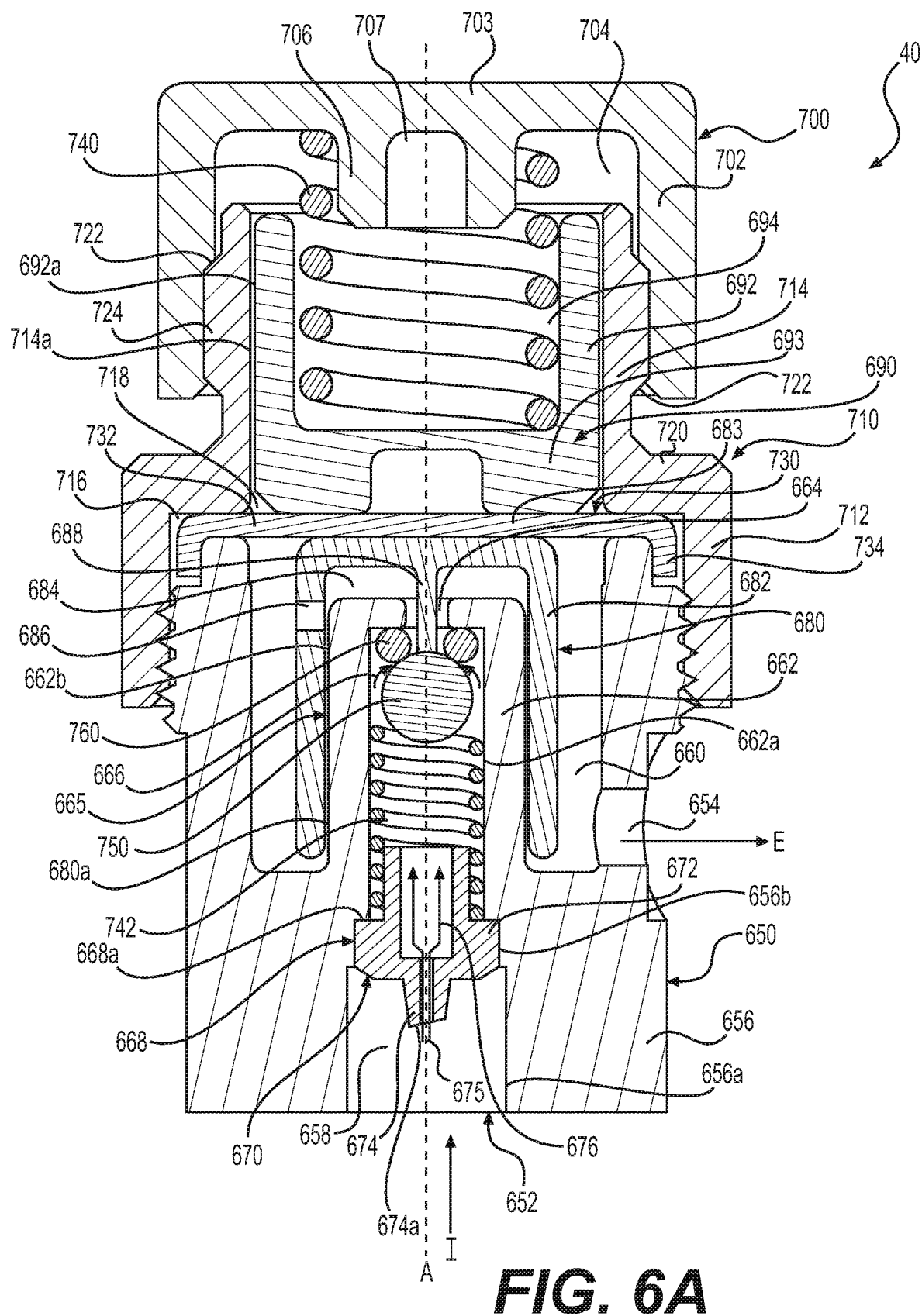
FIGS. 6A-6C are cross-sections of a regulator according to an embodiment.
Figure 8:
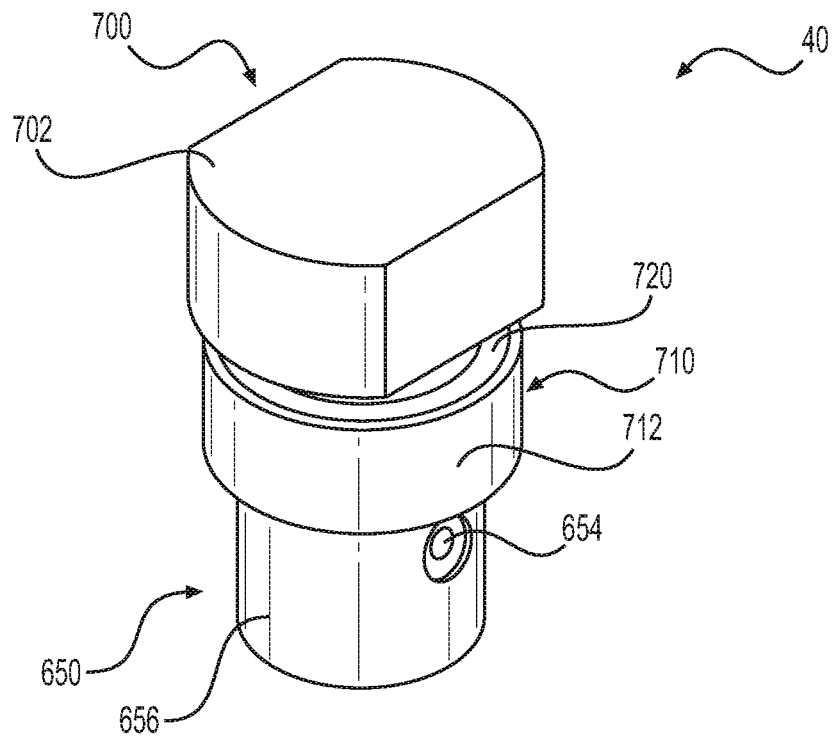
FIG. 8 is a perspective view of a regulator according to an embodiment.

With reference to FIGS. 6A and 8, regulator 40 according to an embodiment will be described. Regulator 40 includes a body 650 (including an input opening 652 and an output opening 654, each for communication to external environment), a cap 700, and a capture cylinder 710 (e.g., capture member). A membrane 730 is provided between a piston 690 and an actuator 680. As further shown in FIG. 6A, regulator 40 includes a pierce pin 670, first and second springs 740, 742, a ball bearing 750 (or another type of body), and an O-ring 760.

Figure 9:
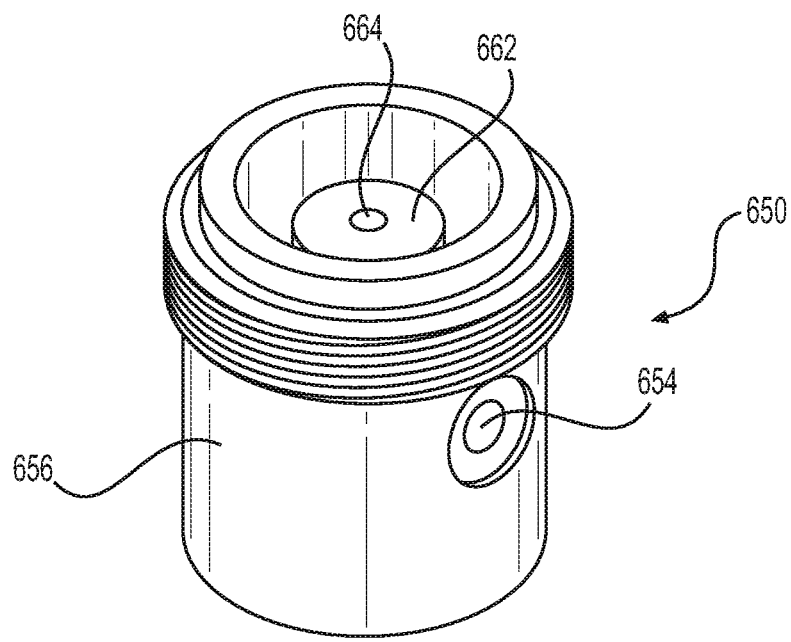
FIG. 9 is a perspective view of a body of a regulator according to an embodiment.

With reference to FIGS. 6A and 9, body 650 of regulator 40 is generally cylindrical and has a central axis A. Body 650 includes a regulator wall 656, and a first chamber 658 (adjacent input opening 652) and a second chamber 660, each defined within regulator wall 656. Regulator wall 656 may include screw threads on a radially-outer surface of wall 656 for attachment to additional structures, as discussed herein. An inner diameter of regulator wall 656 in first chamber 658 is smaller than an inner diameter of regulator wall 656 in second chamber 660. A cylindrical protrusion 662 extends into second chamber 660, cylindrical protrusion 662 having a hole 664 at it upper end, transverse to and coaxial with central axis A. Hole 664 is in fluid communication with a third chamber 666, defined by an inner wall 662a of cylindrical protrusion 662. Third chamber 666 is in fluid communication with, and between, first chamber 658 and second chamber 660. According to an embodiment, there is no O-ring or other sealing member provided in second chamber 660, thereby eliminating friction forces at and between regulator wall 656 and actuator 680 during movement of actuator 680. Additionally, body 650 may be any material known in the art, including but not limited to a metal alloy, a ceramic, and/or a resin.

As shown in FIG. 6A, O-ring 760 is disposed adjacent to inner wall 662a, within third chamber 666, and lies adjacent to hole 664. Ball bearing 750 is adjacent to O-ring 760 on a side opposite hole 664. As will be described herein, ball bearing 750 and O-ring 760 are capable of sealing hole 664 from communication with third chamber 666. Second spring 742 is disposed in third chamber 666 between, and in contact with both of, pierce pin 670 and ball bearing 750. Second spring 742 is sized to have an outer diameter smaller than a diameter of inner wall 662a, such that second spring 742 can expand and contract without creating friction forces between it and inner wall 662a. O-ring 760 and ball bearing 750 are sized such that an outer diameter of each is less than the inner diameter of inner wall 662a. In that way, when O-ring 760 and/or ball bearing 750 are not sealing hole 664, fluid flows within chamber 666, between inner wall 662a and ball bearing 750, within and/or around O-ring 760, and through hole 664 to chamber 660. According to an example, a seal effective diameter where ball bearing 750 seals against O-ring 760 is approximately 0.05 inches to 0.14 inches, and preferably approximately 0.08 inches to 0.11 inches.

With continued reference to FIG. 6A, first chamber 658 is in fluid communication with third chamber 666, via a pierce pin chamber 676 within pierce pin 670. First chamber 658 includes an area having a first diameter (defined by wall surface 656a) and an area having a second, smaller diameter (defined by wall surface 656b). Surfaces of first chamber 658 may include threads (not shown) to accommodate components which may be used to pierce containment device 20'. Alternatively, threads of surfaces of first chamber 658 may accommodate a threaded containment device 20'. For example, when containment device 20' is screwed into first chamber 658 (using, e.g., threads), pierce pin 670 may pierce containment device 20'. Third chamber 666 is adjacent to, and has a smaller diameter than, the second diameter area of chamber 658. The confluence of the second diameter area of chamber 658 and third chamber 666 defines a notch 668 outside and along a perimeter of third chamber 666. Notch 668, at its top, defines an annular flanged surface 668a.

Pierce pin 670 is shown in FIG. 6A. According to an embodiment, pierce pin 670 may be disposed in notch 668 and abut flanged surface 668a. According to an embodiment, pierce pin 670 may have an outer diameter equal to an inner diameter of the second diameter area of chamber 658. Pierce pin 670 includes a body portion 672 and a protrusion 674 extending from body portion 672 into chamber 658, pierce pin 670 defines pierce pin chamber 676 open at both ends, and extending through body 672 and protrusion 674. First chamber 658 may be in fluid communication with pierce pin chamber 676 via opening 675. A first portion of chamber 676 adjacent to chamber 666 has a larger diameter than a second portion of chamber 676 adjacent to chamber 658. According to an embodiment, protrusion 674 includes an end wall 674a angled relative to central axis A, preferably not perpendicular to central axis A. Pierce pin 670 may be fixed to body 650 by, for example, adhesive, friction between body 650 and pierce pin 670, welding, threads, etc. Additionally, or alternatively, pierce pin 670 may be formed as a single structure with body 650 through, for example, additive manufacturing. Pierce pin 670 may have any suitable geometry, including, for example, an arrow shape (not shown). In such a configuration, instead of having a protrusion 674, surfaces of pierce pin 670 may slope radially outwardly from a narrow portion proximate to opening 675. The sloped surfaces may terminate in a shoulder portion and include a stem extending from the shoulder portion, into third chamber 666. An arrow-shaped pierce pin 670 may facilitate forming a relatively large hole in containment device 20'. Air may flow through opening 675 and the stem portion, into third chamber 666.

According to an embodiment, protrusion 674 of pierce pin 670 pierces a gasket of containment device 620 or conduit 622. Alternatively, or additionally, protrusion 674 interacts with a device (not shown) on containment device 20' or conduit 22, such as locking with the device, providing a fluid connection between regulator 40 and containment device 20' or conduit 22. According to an embodiment, pierce pin 670 may be any material known in the art, including but not limited to a metal alloy, a ceramic, and/or a resin.

FIG. 6A further illustrates actuator 680, which is a cylindrical member having an outer actuator wall 682 and a top wall 683 defining an actuator chamber 684. Actuator chamber 684 is open at one end of actuator 680, the end facing the bottom of FIG. 6A opposite top wall 683. According to an embodiment and as shown in FIG. 6A, actuator 680 may include a throughhole 686 in actuator wall 682 near top wall 683, as will be described in greater detail herein. According to an embodiment, a central axis of though hole 686 is perpendicular to a prong 688. Additionally, as shown in FIG. 6A, prong 688 may extend from top wall 683 into chamber 684. Prong 688 may be perpendicular to top wall 683, extending along central axis A into through hole 664 and into chamber 666. When assembled, actuator 680 is provided in second chamber 660 and annularly surrounds at least a portion of cylindrical protrusion 662. Actuator 680 and cylindrical protrusion 662 are sized such that an outer wall 662b of cylindrical protrusion 662 has a diameter smaller than a diameter of an inner wall 680a of actuator 680, thereby forming an annular space 665 between actuator 680 and cylindrical protrusion 662. In this way, actuator 680 can slide (translate) along central axis A and fluid can flow between actuator 680 and cylindrical protrusion 662 in space 665. According to an embodiment, actuator 680 may be any material known in the art, including but not limited to a metal alloy, a ceramic, and/or a resin.

With continued reference to FIG. 6A, piston 690 is generally cylindrical in shape, including an outer piston wall 692 and a bottom wall 693, an inner surface of piston wall 692 and an upper surface of wall 693 defining a piston chamber 694, with piston chamber 694 being open at an upper end opposite wall 693. According to an embodiment, piston 690 may be any material known in the art, including but not limited to a metal alloy, a ceramic, and/or a resin.

Cap 700 is also generally cylindrical in shape, having a cap outer wall 702 and an upper cap wall 703, together defining a cap chamber 704, which is open at one end. Protuberance 706 extends from, and generally perpendicular to, upper cap wall 703. As shown in FIG. 6A, spring 740 is provided in piston chamber 694. A first end of spring 740 contacts an inner upper surface of piston wall 693. Spring 740 extends up to and encircles at least a portion of protuberance 706, such that an end of spring 740 opposite the first end contacts an inner, lower surface of upper cap wall 703. A hole (not shown) may be formed in upper cap 703 above a protuberance chamber 707 formed by walls of protuberance 706, such that chamber 707 and piston chamber 694 may be in fluid communication with the atmosphere. Such a hole may relieve vacuum or pressure built up in piston chamber 694 as membrane 732 moves as described below.

Figure 10:
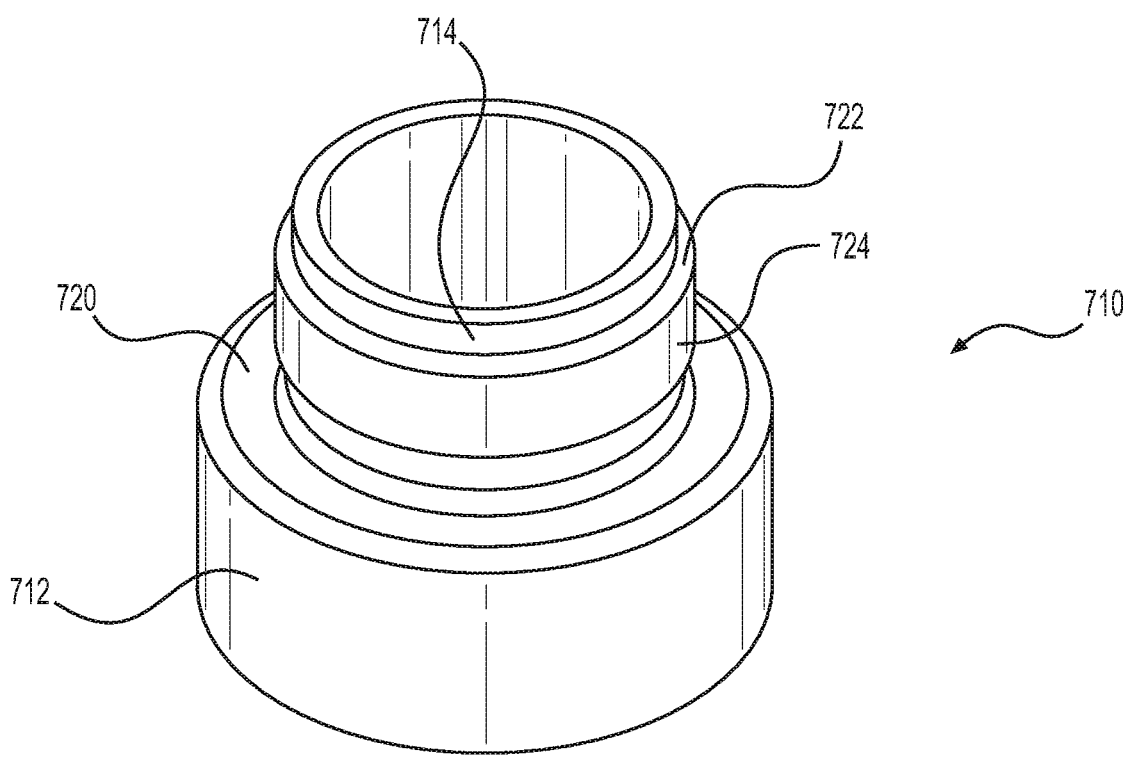
FIG. 10 is a perspective view of a capture cylinder of a regulator according to an embodiment.

FIGS. 6 and 10 illustrate capture cylinder 710, which is generally cylindrical in shape. A first wall 712 defines a first chamber 716, and a second wall 714, connected by a step portion 720 to first wall 712, defines a second chamber 718. First chamber 716 and second chamber 718 are fluidly connected, and capture cylinder 710 is open at the ends of first chamber 716 and second chamber 718. According to an embodiment, a diameter of first chamber 716 is greater than a diameter of second chamber 718; however, capture cylinder 710 is not limited to this configuration. As shown in FIG. 6A, piston 690 rests inside second chamber 718 such that the open end of piston chamber 694 and the open end of second chamber 718 face a same direction (the top of FIG. 6A). Piston 690 is sized and shaped to slide within second chamber 718, as will be described in greater detail herein. For example, an outer diameter of wall 692a of piston 690 is smaller than a diameter of an inner wall 714a of capture cylinder 710, thereby reducing and/or eliminating friction forces between piston 690 and capture cylinder 710. This reduced friction provides more freedom of movement between elements, thereby improving the consistency of the output pressure and flow rate of the fluid.

As shown in FIGS. 6 and 10, an outer portion of second wall 714 includes a thickened annular region 724. Region 724 includes walls 722 which taper to the thinner regions of second wall 714. According to an embodiment, first wall 712 and second wall 714 are generally parallel to central axis A and perpendicular to wall 720, but are not limited to this configuration. As shown in FIG. 6A, region 724 allows cap 700 to be fixedly attached to and seal capture cylinder 710. For example, cap 700 may be snap-fit, welded, glued, screwed, or attached in any manner known in the art to capture cylinder 710. Attachment of cap 700 to capture cylinder 710 may allow cap 700 to be removed, for example, using screw threads. Alternatively, cap 700 may be fixedly secured to cylinder 710 and unable to be removed without destroying regulator 40, for example, by welding cap 700 to capture cylinder 710. Cap 700 may be configured so as to compress spring 740 by a predetermined amount in a relaxed state of regulator 40, when pressurized fluid is not flowing into/through regulator 40. The predetermined compression of spring 740 may determine a pressure that is output via output opening 654 when high pressure fluid flows through input opening 652. A compression of spring 740 by cap 700 may be adjustable after regulator 40 is assembled (e.g., to allow for varying output pressures) or could be fixed during assembly of regulator 40.

With continued reference to FIG. 6A, membrane 730 is provided in first chamber 716 of capture cylinder 710. Membrane 730 includes a base 732 and a wall 734 extending along a circumference of and generally perpendicular to base 732. According to an embodiment, membrane 730 is formed of a silicone material, but is not limited thereto. For example. membrane 730 may be any material which is flexible and reduces a friction coefficient between membrane 730 and the other structures of regulator 40.

As shown in FIG. 6A, membrane 730 covers top wall 683 and the upper opening of second chamber 660 of body 650. An inner diameter of wall 734 is approximately equal to an outer diameter of an upper portion of regulator wall 656 of body 650, allowing membrane 730 to seal the upper opening of second chamber 660. As will be discussed herein, this prevents fluid from escaping body 650 (other than through output opening 654) during operation of regulator 40. When assembled, a lower surface of step portion 720 of capture cylinder 710 contacts a top surface of base 732 and fixes membrane 730 to base 650. In that way, membrane 730 is squeezed between cylinder 710 and base 650. For example, as shown in FIG. 6A, capture cylinder 710 is screwed to body 650, but may be snap-fit, welded, glued, or attached in any manner known in the art. Alternatively, or additionally, membrane 730 may be fixed to base 650 independent of capture cylinder 710, such as using an adhesive. According to an example, to reduce the sensitivity of a changing pressure at inlet 632, membrane effective diameter, which is the outer diameter of second chamber 660 in contact with membrane 730, is approximately 0.6 inches to 1.25 inches, and preferably 0.7 inches to 1.0 inch.

An operation of regulator 40 will now be described.

Figure 6B:
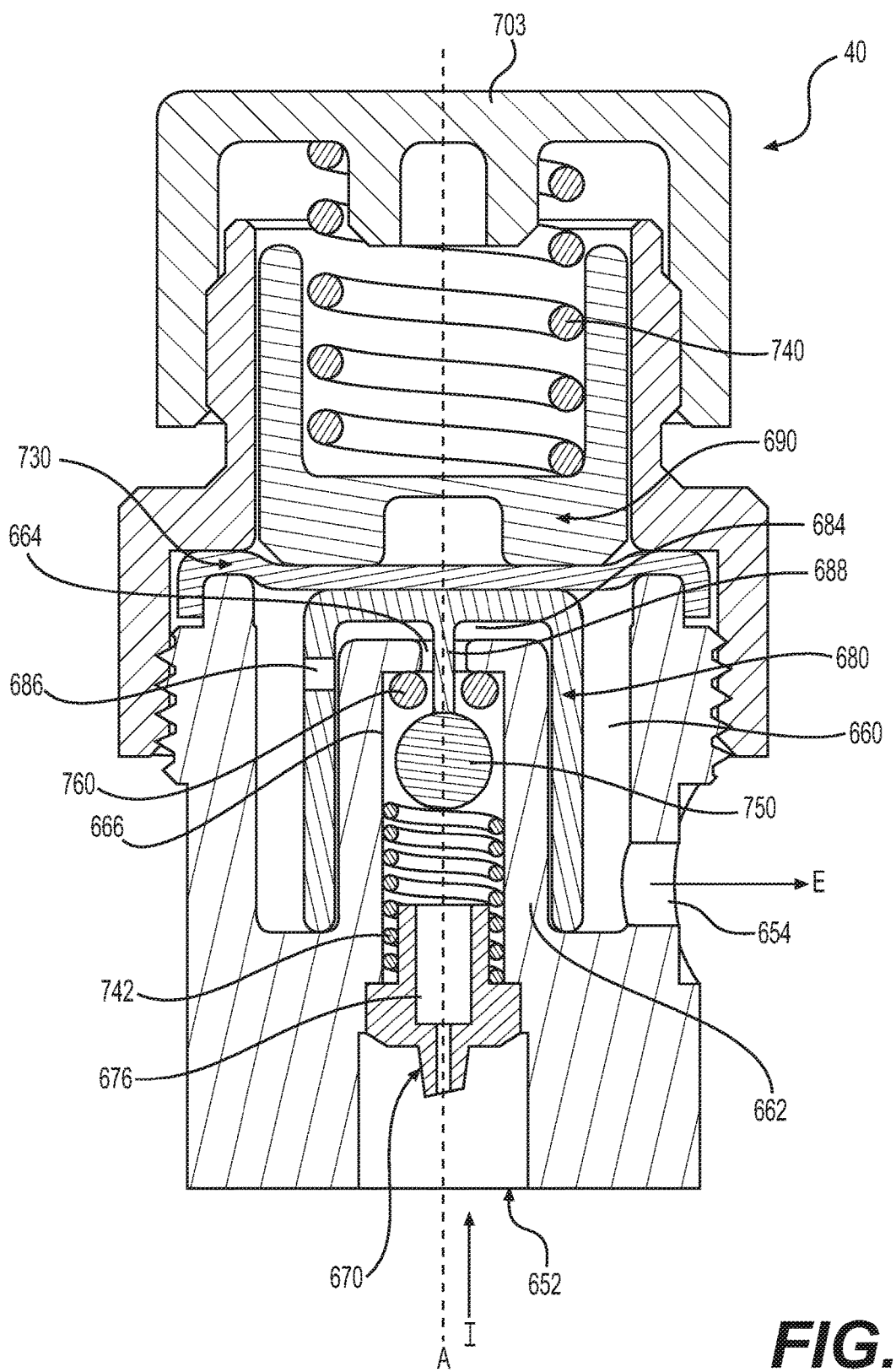
Figure 6C:
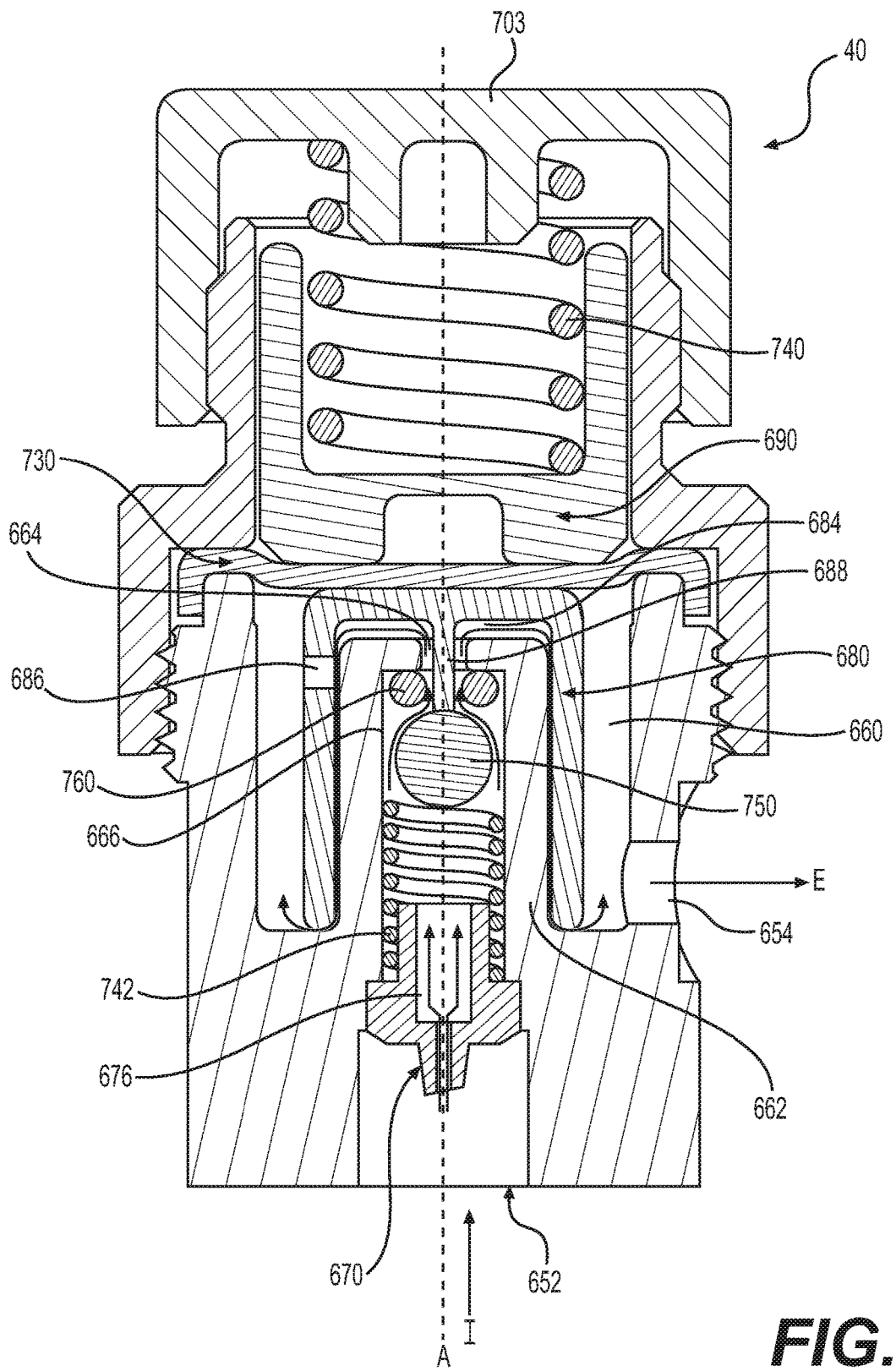

FIG. 6A shows regulator 40 in a configuration in which third chamber 666 is sealed, meaning that fluid may not pass through hole 664 and that third chamber 666 is not in fluid communication with second chamber 660 and output opening 654. FIG. 6B shows regulator 40 in a configuration in which third chamber 666 is not sealed (fluid may pass through hole 664 such that third chamber 666 is in fluid communication with second chamber 660 and output opening 654), but regulator 40 is not receiving high pressure fluid from a source such as containment device 20, 20'. FIG. 6C shows regulator 40 in a configuration in which third chamber 666 is not sealed (fluid may pass through hole 664 such that third chamber 666 is in fluid communication with second chamber 660 and output opening 654) and regulator 40 is receiving high pressure from a fluid source such as containment device 20, 20'.

With reference to FIG. 6B, when regulator 40 is not exposed to any high pressure (e.g., when a containment device 20, 20', which is not shown in FIGS. 6A-6C, is not installed or when pierce pin 670 has not yet punctured containment device 20, 20'), regulator 40 is in a resting state of equilibrium, as shown in FIG. 6B. In the resting state, spring 740 may exert a force in a first direction along central axis A, toward pierce pin 670. The force in the first direction from spring 740 may be transmitted to piston 690 and membrane 730, which may transmit a force in the first direction to actuator 680 (including prong 688). When prong 688 is in contact with ball bearing 750, prong 688 may transmit a force in the first direction to ball bearing 750 and, in turn, to spring 742.

Meanwhile, spring 742 may exert a force in a second, opposite direction along central axis A, toward upper cap wall 703 (a direction opposite the force exerted by spring 740). A force from spring 742 may be transmitted to ball bearing 750, which may, via contact with prong 788, exert a force in the second direction on actuator 780, membrane 730, piston 690, and spring 740. Spring 742 may be configured to urge ball bearing 750 in the second direction, toward O-ring 760.

A spring constant of spring 740 may be larger than a spring constant of spring 742 (i.e., spring 740 may be stiffer than spring 742). Due to the larger spring constant of spring 740, spring 740 may dominate spring 742. In the resting state of FIG. 6B, membrane 730 may be deformed such that it protrudes in the first direction, toward pierce pin 670. Prong 688 may press in the first direction against ball bearing 750 such that there is a gap between ball bearing 150 and O-ring 160, and third chamber 666 is unsealed/open, so that fluid may pass through hole 664 and third chamber 666 is in fluid communication with second chamber 660 and output opening 654.

After high pressure is introduced to regulator 40, as shown in FIG. 6C, high-pressure fluid may pass through input opening 652, through pierce pin chamber 676, and into third chamber 666. Fluid may then pass through the gap between ball bearing 750 and through hole 664 into actuator chamber 684. Fluid may then flow between actuator 680 and protrusion 662 to second chamber 660. As shown in FIG. 6C, fluid may also pass via throughhole 686 to second chamber 660. Fluid subsequently passes as a fluid through output opening 654 (shown by arrow E).

When actuating devices 634 are not actuated, valves (not shown) are closed, and fluid does not flow through delivery system 10. Fluid may be prevented from passing downstream (toward outlet 34) of a portion of delivery system 10 (e.g., a valve) controlled by actuating devices 36a, 36b. Therefore, pressure may build up in portions of system 10 that are upstream (away from outlet 34) of that portion (e.g., valve) of delivery system 10. Regulator 40 may be upstream of that portion (e.g., valve), and therefore pressure may build up in regulator 40.

The increasing pressure within regulator 40 may affect various components of regulator 40 and may cause regulator 40 to transition from the configuration of FIG. 6C (open/unsealed) to the configuration shown in FIG. 6A (closed/sealed). For example, pressurized fluid building in second chamber 660 may result in a force on membrane 730 in the second direction. This force may be transmitted to piston 690 and spring 740. Pressurized fluid in third chamber 666 may also result in a force on ball bearing 750 in the second direction. This force on ball bearing 750 may be transmitted to actuator 680, membrane 730, piston 690, and spring 740.

These additional forces in the first direction may overcome a force of spring 740 in the first direction, such that ball bearing 750, actuator 680, membrane 730, and piston 690 move in the second direction, toward upper cap wall 703. Membrane 730 may be flat or approximately flat in the configuration shown in FIG. 6A, as shown. Membrane 730 may also be capable of deforming further in the second direction so that membrane 730 protrudes in the second direction. For example, membrane 730 may protrude or bow in the second direction when sufficient force is exerted on ball bearing 750, such as in a fully pressurized configuration. It will be appreciated that FIGS. 6A-6C are merely exemplary and that a range of positions of the components of regulator 40 may be possible. For example, in a resting equilibrium (when regulator 40 is not exposed to pressurized fluid), membrane 730 may be straight and may protrude in the second direction when regulator 40 is pressurized.

In the configuration of FIG. 7A, ball bearing 750 may press against O-ring 760, forming a seal between ball bearing 750 and O-ring 760. When ball bearing 750 and O-ring 760 are sealed, third chamber 666 may be sealed such that fluid may not move through hole 664 into actuator chamber 684. Arrows in FIG. 6A show a path of fluid flow when fluid is flowing into input opening 652 but cannot exit hole 664. Thus, a pressure of fluid in second chamber 660 (and areas downstream of output opening 654) may be capped at a certain value (e.g., the regulated pressure of between 25 and 100 PSI, as discussed below). As discussed in further detail below, this regulation of pressure in second chamber 660 occurs both when actuating devices 634 are actuated or are not actuated. This pressure regulation protects components of delivery system 10, as well as a subject of a procedure using delivery system 10. Eventually, where a discrete containment device 20, 20' is used, pressure in third chamber 666 may equalize with a pressure of containment device 20, 20', such that fluid no longer flows from containment device 20, 20' through input opening 652.

When actuating devices 36a, 36b are opened, fluid may be free to travel from outlet 34 because downstream valves are open. Thus, fluid may flow from second chamber 660 and out of output opening 654, thereby equalizing pressure between second chamber 660 and the atmosphere surrounding application device 30. Because second chamber 660 is no longer at a high pressure, the fluid in second chamber 660 may no longer exert a force in the second direction on membrane 730. As a result, the net force along the second direction may decrease (although high-pressure fluid continues to exert a force on ball bearing 750 in the second direction), and regulator 40 may transition to a configuration like that shown in FIG. 6C. The force of spring 740 pushing against piston 690 and membrane 730 in the first direction causes actuator 680 to move toward pierce pin 670 along central axis A. Movement of actuator 680 toward pierce pin 670 causes prong 688 to push ball bearing 750 against spring 742, thereby providing an opening through hole 664 of protrusion 662. It will be appreciated that an amount that hole 664 is open may vary depending on a balance of the forces in the first direction (exerted by spring 740) and in the second direction (exerted by spring 742, and high-pressure fluid on membrane 730 and ball bearing 750). FIG. 6C shows an exemplary open configuration. However, portions such as membrane 730, actuator 680, and/or ball bearing 750 may vary in their position depending on the balance of forces acting at that time, allowing more or less fluid to pass through hole 664. A varying amount of fluid passing through hole 664 may facilitate maintaining second chamber 660 at a desired regulated pressure (described in further detail below).

While the third chamber 666 is unsealed (FIG. 6C), pressurized fluid may flow from containment device 20, 20', through input opening 652, and through hole 664. For example, as shown in FIG. 6C, a flow path (arrows in FIG. 6C) shows a fluid input I through input opening 652. Fluid flows in the direction of the arrows through pierce pin chamber 676 and into third chamber 666. Fluid flows through hole 664 into actuator chamber 684, and flows between actuator 680 and protrusion 662 to second chamber 660. As shown in FIG. 6C, fluid may also pass via throughhole 686 to second chamber 660. Fluid subsequently passes as a fluid through output opening 654 (shown by arrow E). The fluid output is controlled by regulator 40, as described herein. While not shown, one or more devices, such as a tube, a catheter, or an application tip, may be attached to outlet 34 to aid in supplying fluid to a desired location, as will be described in detail herein.

If high pressure fluid accumulates in second chamber 660, the pressure may exert a force in the second direction on membrane 730, as described above, causing membrane 730 to move in the second direction. This force may be transmitted to piston 690. Pressurized fluid in third chamber 666 may also result in an a force on ball bearing 750 in the second direction, as discussed above. These forces, together or separately, may cause regulator 40 to transition to a configuration in which third chamber 666 is sealed via ball bearing 750 and O-ring 760 (as shown in FIG. 6A). The interactions described above may cause regulator 40 to iteratively transition between configurations in which third chamber 666 is sealed or unsealed.

Using the mechanisms described herein, regulator 40 controls a fluid pressure supply through output opening 654. For example, the pressure is controlled by regulating the opposing forces of spring 740 on one side and spring 742 and fluid pushing against ball bearing 750 and membrane 730 on the other side.

The spring force of springs 740 and 742 are predetermined based on a desired pressure of a fluid that is to be dispersed and a desired rate at which the fluid is to be dispersed. For example, a spring with a lower rate (i.e., lowest amount of weight to compress a spring one inch) and higher compression/compressibility may achieve greater control over a pressure of fluid through output opening 654. For example, according to an embodiment, regulator 40 may be designed to supply a hemostatic agent to a tissue at a pressure between approximately 25 and 100 PSI, and more particularly between approximately 40 to 60 PSI, and at a rate of approximately 5 to 15 liters per minute (LPM), and more particularly between 7 and 10 LPM. Regulator 40 provides a consistent pressure and flow of fluid from containment device 20, 20'.

As fluid is released from containment device 20, 20', a pressure released from containment device 20, 20' changes, for example, from a high pressure (approximately 850 PSI) to zero PSI when containment device 20, 20' is empty. As the pressure in containment device 20, 20' decreases, the pressure of fluid against ball bearing 750 and membrane 730 changes (e.g., lessens), reducing the force exerted in the second direction against spring 740. Thus, as the pressure in containment device 20, 20' decreases, the force of spring 740 causes a greater portion of hole 664 to be open, thereby providing a consistent rate of flow and pressure of the fluid supply at output 654. However, a pressure of fluid from containment device 20, 20' may be great enough to continue to exert forces on ball bearing 750 to provide sealing of chamber 666 via contact between ball bearing 750 and O-ring 760 when regulation of pressure is required.

The configuration shown in FIG. 6A improves consistency of flow rate and output pressure of fluid. For example, membrane 730 is a silicone or other friction-reducing material. Silicone may remain flexible at low temperatures that may be present in regulator 40 due to high flow rates of fluid from containment device 20, 20'. That is, as actuator 680 moves along central axis A, there is no structure, such as an O-ring, in second chamber 660 between and in contact with actuator 680 and an inner surface of regulator wall 656 of body 650. Such a structure would cause friction forces, making it difficult for actuator 680 to move, thereby decreasing the consistency at which a flow rate and output pressure of a fluid may be maintained. Thus, regulator 40 of FIG. 6A minimizes friction forces when actuator 680 and piston 690 are moved along central axis A, providing improved consistency in the flow rate and output pressure of the fluid.

Figure 7:
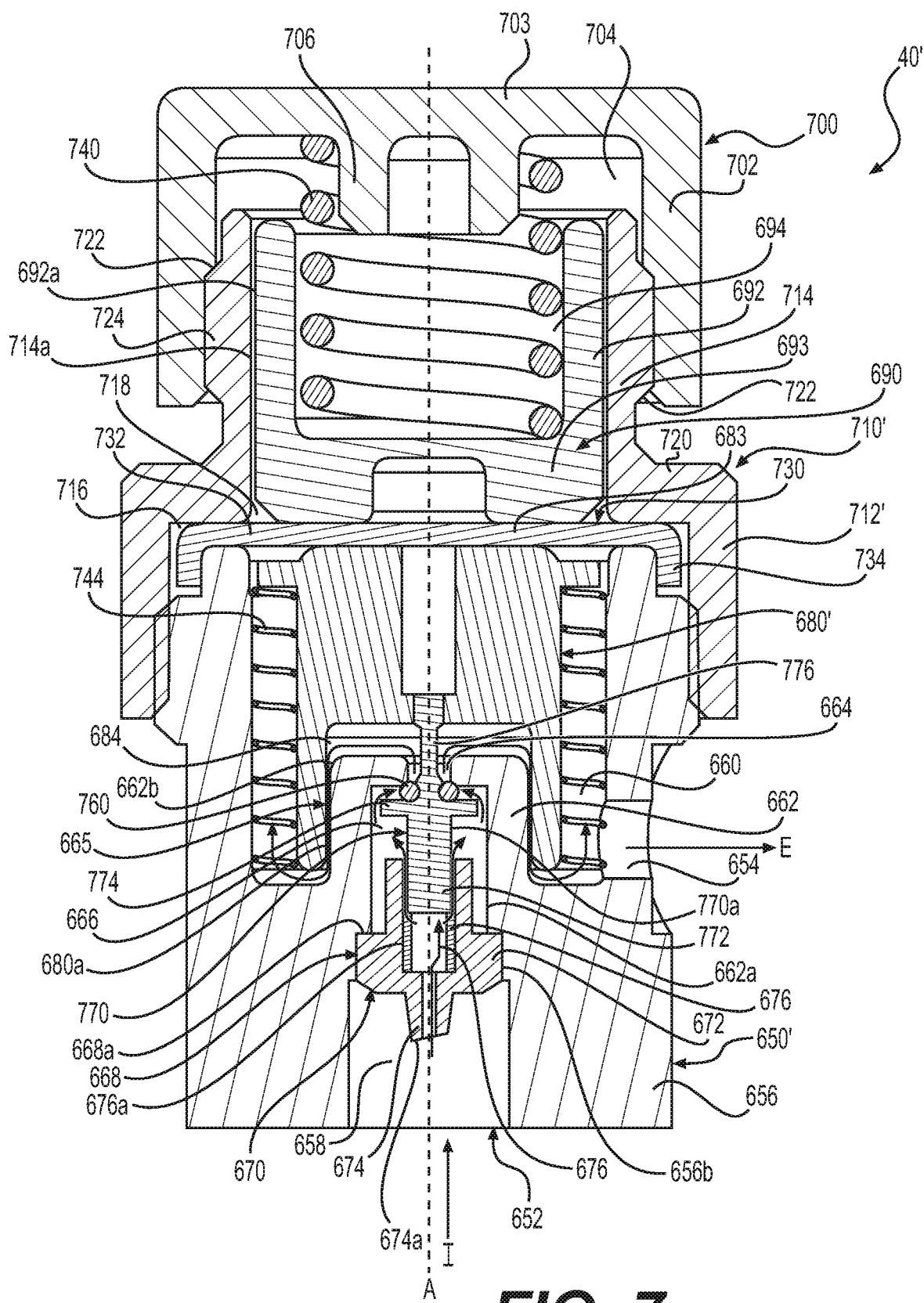
FIG. 7 is a cross-section of a regulator according to another embodiment.

FIG. 7 illustrates another embodiment of a regulator 40'. Like elements in FIG. 7 have like reference characters as those in FIG. 6A. As shown in FIG. 7, regulator 40' has some different structures for regulating fluid flow and pressure. Further, regulator 40' illustrates a snap-fit connection between capture cylinder 710' and body 650'. For example, in the embodiment illustrated in FIG. 7, a regulator wall 656' is snap fit together with a first wall 712' of capture cylinder 710'. Additionally, and or alternatively, capture cylinder 710' and body 650' may be attached by adhesive, welding, or any other attachment mechanism known in the art.

As shown in FIG. 7, actuator 680' interacts with a poppet 770. Poppet 770 includes a body 772, tabs 774, and a protrusion 776. One end of protrusion 776 is configured to contact actuator 680'. Protrusion 776 may be fixed to actuator 680' by, example, adhesion or welding, to allow protrusion 776 and actuator 680' to move together, as discussed in greater detail herein. Protrusion 776 extends through hole 664 in base 650', and O-ring 760' seals the space between hole 664 and tabs 774. O-ring 760' may be a resin or any other material known in the art (e.g., silicone) for fluidly sealing an opening. According to an example, a seal effective diameter where O-ring 760' seals against the space between hole 674 and tabs 774 is approximately 0.05 inches to 0.14 inches, and preferably approximately 0.08 inches to 0.11 inches. As further shown in FIG. 7, body 772 extends into chamber 676 of pierce pin 670, such that poppet 770 moves axially with respect to pierce pin 670. For example, an outer wall 770a of poppet 770 has a diameter smaller than a diameter of inner wall 676a of chamber 676. In this way, fluid may flow from input opening 652 to third chamber 666. In the embodiment of FIG. 7, a spring 744 is provided in second chamber 660, annularly disposed around cylindrical protrusion 662, and causes actuator 680' to move along central axis A, as will be described herein.

As in FIG. 6A, O-ring 760' in FIG. 7 is disposed adjacent inner wall 662a within third chamber 666 and lies adjacent to hole 664. Tabs 774 are adjacent to O-ring 760' on the side opposite hole 664. O-ring 760' may be fixed relative to tabs 774. For example, tabs 774 may include grooves or alternative structures for receiving O-ring 760'. As will be described herein, tabs 774 and O-ring 760 are capable of sealing hole 664 from communication with third chamber 666 when O-ring 760' is pressed against inner wall 662a. Third spring 744 is disposed in second chamber 660 between, and in contact with both of, actuator 680' and base 650. Third spring 744 is sized to have an outer diameter smaller than an outer diameter of second chamber 660, such that third spring 744 can expand and contract without creating friction forces between it and an outer wall of second chamber 660. O-ring 760' and tabs 774 are sized such that an outer diameter of each is less than the diameter of inner wall 662a. In that way, when O-ring 760' and/or tabs 774 are not sealing hole 664, fluid flows between inner wall 662a and tabs 774 and/or O-ring 760' and through hole 664 to chamber 660.

An operation of regulator 40' will now be described. Regulator 40' of FIG. 7 operates in a similar manner as described with reference to FIG. 6A. Regulator 40' may have a first, sealed, configuration, shown in FIG. 7, in which O-ring 760' presses against inner wall 662a and creates a seal such that fluid may not pass between O-ring 760 and inner wall 662a or between O-ring 760' and tabs 774. Thus, fluid may be unable to pass through hole 664, Regulator 40' may have a second, unsealed configuration (not shown), in which O-ring 760' does not form a seal with inner wall 662a and/or tabs 774, so that fluid may flow through hole 664.

Spring 744 provides an opposing force to spring 740. When one or more actuating devices 36a, 36b of application device 30 are manipulated, a pressure between second chamber 660 and an atmosphere surrounding application device 630 are equalized, thereby transitioning regulator 40' from the sealed configuration of FIG. 7 (where O-ring 760' prevents passage of fluid through hole 664) to an unsealed configuration (where O-ring 760' does not prevent passage of fluid through hole 664) and thus releasing fluid. As discussed herein, during the release of fluid, spring 740 presses piston 690 against membrane 730, thereby pressing actuator 680' toward pierce pin 670. Movement of actuator 680' toward pierce pin 670 causes poppet 770, including O-ring 760', to move in the first direction, toward pierce pin 670. As poppet 770 moves in the first direction, a space is created between O-ring 760' and inner wall 662a. Fluid from containment device 20, 20' may flow through the space between O-ring 760 and inner wall 662a and pass through hole 664. Alternatively, tabs 774 of poppet 770 to loosen around O-ring 760, thereby creating an opening between third chamber 666 and hole 664. Fluid may move from containment device 20, 20', through chamber 676 of pierce pin 670, into second chamber 660, and through output opening 654, as shown by the flow path in FIG. 7. Although regulator 40' is shown in a configuration in which fluid may not pass through output opening 654, due to a seal between tabs 774 and O-ring 760', the flow path in FIG. 7 shows how fluid would flow when tabs 774 are loosened around O-ring 760'. The configuration shown in FIG. 7 similarly improves consistency of flow rate and output pressure of fluid. The configuration of FIG. 7, in particular, may reduce a sealing diameter between O-ring 760', tabs 774, and inner wall 662a. This decreased diameter may allow for increased sealing, which may prevent fluid from passing through hole 664 when such passage would cause a deviation from the desired regulated pressure. As discussed with regard to FIGS. 6A-6C, movement of membrane 730 and actuator 680' may allow for dynamic adjustment of an amount of fluid that may pass through hole 664 and exit output opening 654.

As discussed herein, membrane 730 reduces a friction between actuator 680 and body 650. This reduced friction provides more freedom of movement between elements, thereby improving the consistency of the output pressure and flow rate of the fluid. As also described herein, throughhole 686 may be provided in actuator 680. Throughhole 686 may assist in providing a consistent pressure and consistent rate of fluid flow from output 654.

Figure 11A:
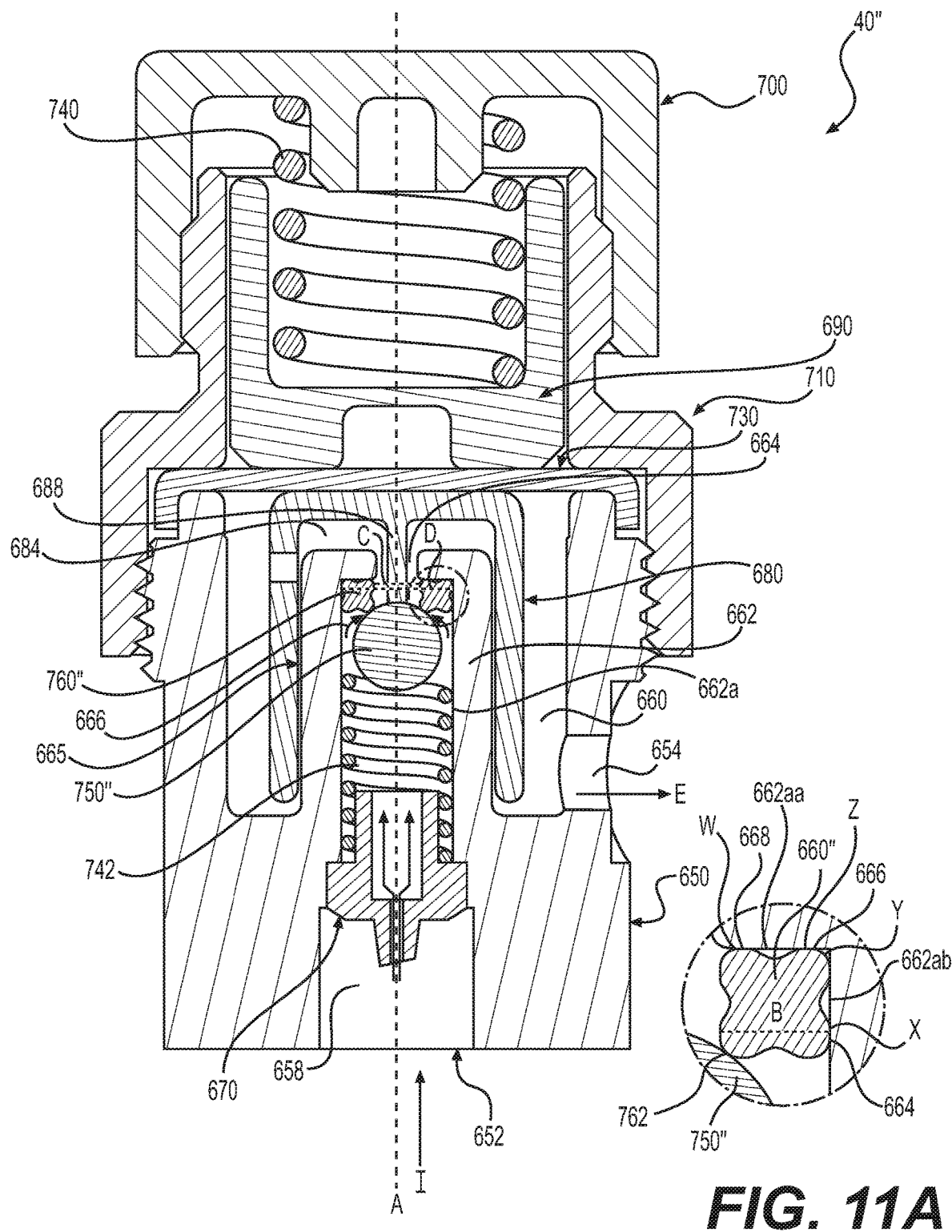
FIGS. 11A and 11B are cross-sections of a regulator according to still another embodiment.
Figure 11B:
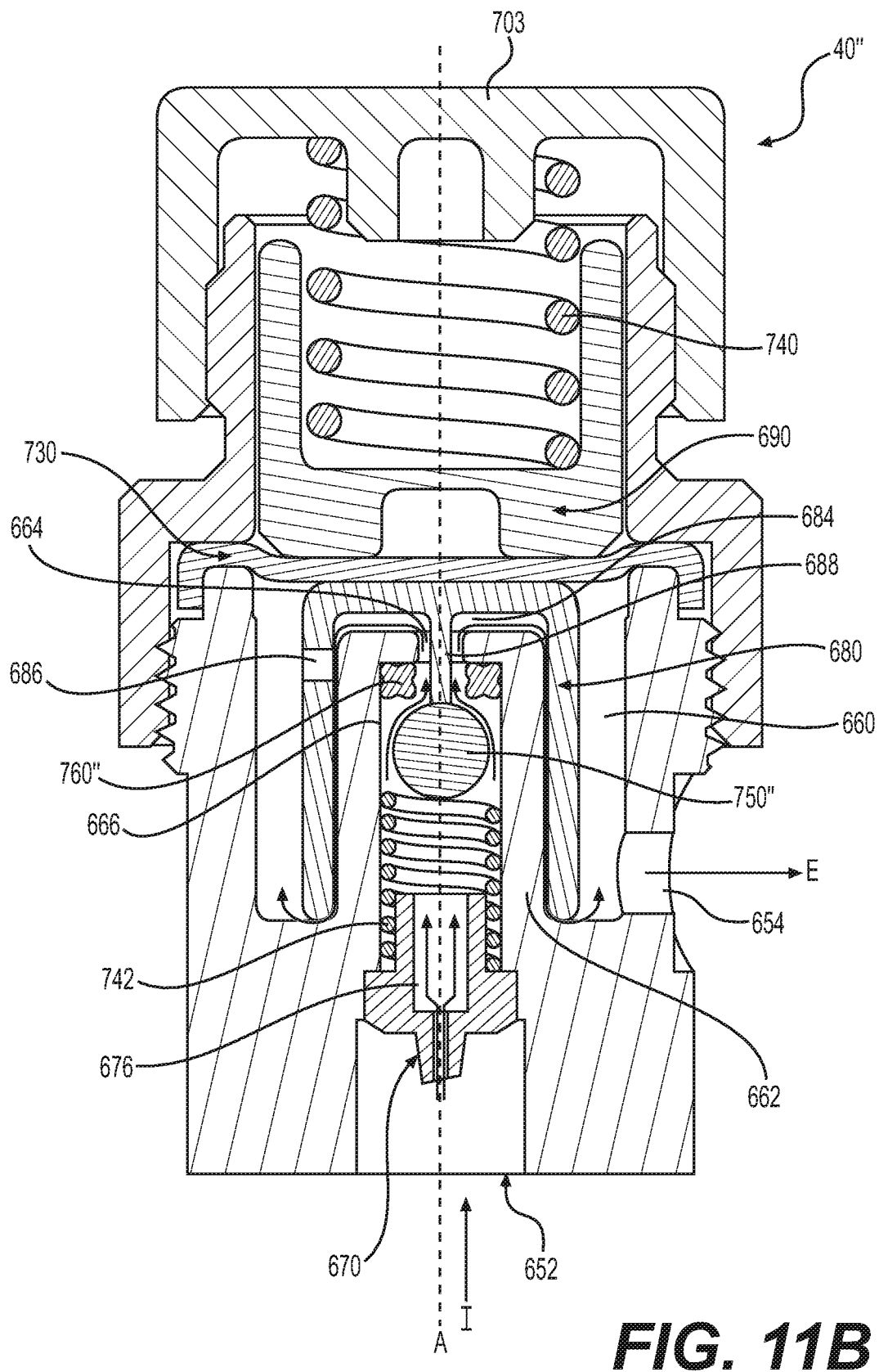

FIGS. 11A and 11B show a further exemplary regulator 40", which may have any of the properties of regulators 40 or 40', described above, and which may be used in conjunction with delivery system 10. Although all of the features of regulator 40" corresponding to those of regulator 40 may not be discussed in the description below, it will be appreciated that those features may be present in regulator 40", unless explicitly stated otherwise. Like reference numbers denote corresponding structures. FIG. 11A shows regulator 40" with third chamber 666 sealed, and FIG. 11B shows regulator 40" with third chamber 666 unsealed.

Regulator 40" may include an X-ring seal 760" (e.g., a quad-ring seal). X-ring seal 760" may have an approximately X-shaped cross-section with rounded corners. X-ring seal 760" may have a central circumference and four protrusions 762, 764, 766, 768 extending radially outward from the central circumference. Alternatively, X-ring seal 760" may have other suitable numbers of protrusions. X-ring seal 760 may have a cross-section similar to an asterisk where X-ring seal 760" has more than four protrusions.

X-ring seal 760" may be fitted against inner wall 662a of cylindrical protrusion 662. For example, inner wall 662a may have a groove or grooves in which X-ring seal 760" may be received. Protrusions 764, 766, and 768 may each be in contact with one or more surfaces of inner wall 662a. For example, as discussed below, surfaces 662aa, 662ab of inner wall 662a may form a corner in which X-ring seal 760" may be received. Each of surfaces 662aa and 662ab may face third chamber 666.

As compared with an O-ring, X-ring seal 760" provides additional points of contact with inner wall 662a. When points of contact are referred to herein, it will be appreciated that contact between X-ring seal 760" and inner wall 662a may extend over more than just a single point and may include a larger (and possibly continuous) area of contact.

X-ring seal 760" may provide four points of contact with inner wall 662a. First surface 662aa of inner wall 662a may be perpendicular or approximately perpendicular to axis A. Second surface 662ab of inner wall 662a may be parallel or approximately parallel to axis A. First surface 662aa and second surface 662ab may meet at a corner. Protrusion 768 may contact first surface 662aa at point W (shown in the inset of FIG. 11A). Protrusion 764 may contact second surface 662ab at point X. Protrusion 766 may have points of contact with both second surface 662ab (at point Y) and first surface 662aa (at point Z). In contrast, an O-ring would provide only one point of contact with first surface 662aa and one point of contact with second surface 662ab. Therefore, X-ring seal 760" provides more redundant sealing than an O-ring by providing additional, separate points of contact. Points W, X, Y, and Z may be separated from one another by a gap or space. Even were one or more points of contact to be breached, other points of contact may provide sealing. X-ring seal 760" could maintain sealing even with two (or three) points of contact broken, while an O-ring with two points of contact broken would fail to provide a seal. Furthermore, having separated points of contact W, X, Y, Z may provide for suction effects, increasing sealing.

A surface area of each of contacts W, X, Y, Z between X-ring seal 760" and inner wall 662a may be smaller than a surface area of each contact between an O-ring and inner wall 662a would be. As compared to O-ring 760, the protrusions 762, 764, 766, 768 of X-ring seal 760" may provide narrower, more focused points of contact between X-ring seal 760" and inner wall 662a. A radius of curvature of each of protrusions 762, 764, 766, and 768 may be less than a radius of curvature of an O-ring, producing more defined points of contact.

When ball bearing 750" (or another type of body) presses against and contacts X-ring seal 760" (at at least one point), these more focused contacts may provide for increased sealing, as compared to an O-ring. Because, as compared to an O-ring, the same (or similar) force is exerted by ball bearing 750" over a smaller area, a greater pressure may be exerted on protrusions 762, 764, 766, 768 of X-ring seal 760", which may provide for increased sealing. Due to the shape of protrusions 762, 764, 766, 768, pressure exerted at each point of contact between X-ring seal 760" and ball bearing 750" or inner wall 662a may be greater than corresponding pressures of an O-ring. As discussed in further detail below, even when ball bearing 750" exerts a relatively smaller force (e.g., when pressure has dropped in containment device 20, 20'), X-ring seal 760" may provide a more reliable seal against ball bearing 750", as compared to an O-ring.

X-ring seal 760" may have a durometer measurement that is chosen to result in the desired sealing properties, described below. For example, the durometer measurement may be 70 or approximately 70. Durometer measurements of seal 760" may range from approximately 55 to approximately 90, and, more particularly, from approximately 70 to approximately 80. X-ring seal 760" may be formed of a material that enables X-ring seal 760" to retain elastomeric properties in conditions such as those which may be present in regulator 40" during operation of delivery system 10 (e.g., in cold temperatures such as those of approximately −50 degrees C. (e.g., between approximately −40 degrees C. and approximately −60 degrees C.)). For example, X-ring seal 760" may be entirely formed from or may include silicone, rubbers (such as nitrile rubbers), and/or polyurethane. An X-ring seal having the qualities of X-ring seal 760" may be used as an alternative to O-ring 760 or 760' in regulators 40, 40', above. O-ring 760 or 760' may have durometer and/or material features of X-ring seal 760", described above.

Regulator 40" may also include ball bearing 750". A material forming ball bearing 750" (or portions thereof) may have a durometer measurement chosen to achieve the desired sealing between ball bearing 750" and X-ring seal 760", described below. For example, a durometer measurement of ball bearing 750" may be 90 or approximately 90. A durometer measurement of ball bearing 750" may range from approximately 80 to approximately 90. A composition of ball bearing 750" may be such that ball bearing 750" does not freeze to other components of regulator 40" when exposed to solid, liquid, and/or freezing gaseous carbon dioxide. For example, ball bearing 750" may be formed entirely of or may include rubber, silicone, nitrile, polyurethane, steels, and/or ceramics. A ball bearing having the characteristics of ball bearing 750" may be used as an alternative to ball bearing 750 in regulator 40, above, either in conjunction or separately from X-ring seal 760" (i.e., regulator 40 may use structures having qualities of either or both of X-ring seal 760" and ball bearing 750").

X-ring seal 760" may have a $1/16$-inch cross section (measured along a line B, shown in the insert of FIG. 11A), a $5/64$-$7/64$-inch internal diameter (measured along a line C, shown in FIG. 11A), and a $13/64$-$15/64$-inch outer diameter (measured along a line D, shown in FIG. 11A). X-ring seal 760" may have a cross section between approximately $1/32$ inch and approximately $3/32$ inch, an internal diameter between approximately $1/16$ inch and approximately $1/8$ inch, and an outer diameter between approximately $5/32$ inch and approximately $1/8$ inch. Ball bearing 750" may have a diameter of approximately 0.188 inches. Similar or alternative sizes may be used, either in regulators 40" for use with system 10 or regulators 40" for use in alternative systems. A size of ball bearing 750" may not exceed a diameter of third chamber 666 and may be greater than an internal diameter of X-ring seal 760'. For example, ball bearing 750" may have a diameter between 0.125 inches and 0.25 inches. For example, a regulator 40" used with an alternative system may have different dimensions than a regulator 40" used with system 10.

An operation of regulator 40" will now be described. Regulator 40" of FIGS. 11A-11B operates in a similar manner as described with reference to FIGS. 6A-6C. Operation of regulator 40" will therefore not be separately described in detail. Differences between an operation of regulator 40 and regulator 40" are described below.

Like ball bearing 750 and O-ring 760, ball bearing 750" and X-ring seal 760" may be capable of sealing hole 664 from communication with third chamber 666. FIG. 11A shows regulator 40" with third chamber 666 sealed so that fluid cannot pass through hole 664. In certain configurations of regulator 40", (as shown in FIG. 11A), ball bearing 750" may exert a force against protrusion 762 of X-ring seal 760". Such configurations are described above, with respect to regulator 40.

As discussed above, a seal between ball bearing 750" and X-ring seal 760" may be stronger than a seal between a ball bearing (such as ball bearing 750) and an O-ring seal (such as O-ring 760). As discussed above, protrusion 762 has a smaller radius of curvature than O-ring 760. Therefore, for a given force, ball bearing 750" exerts a larger pressure on protrusion 762, which provides for tighter sealing between X-ring seal 760" and ball bearing 750".

As ball bearing 750" presses against protrusion 762, second, third, and fourth protrusions 764, 766, 768, respectively, may press against surfaces 662aa and 662ab at points W, X, Y, and Z. As discussed above, protrusions 664, 666, and 668 may provide redundant sealing due to the increased number of contact portions.

The increased sealing provided by ball bearing 650" and X-ring seal 660" may increase performance of regulator 40". For example, increased sealing may prevent fluid from leaking through hole 664 when a pressure should be regulated and third chamber 666 should be sealed. Furthermore, as described above with respect to regulator 40, pressure of fluid released from containment device 20, 20' may change over time. In particular, pressure from containment device 20, 20' may decrease over time. As pressure from containment device 20, 20' decreases, a force exerted by the pressurized fluid, in the second direction, on ball bearing 750" may decrease. However, to achieve the desired, regulated pressure, sealing of chamber 666 may be required. When an O-ring is used, the decreasing force exerted by ball bearing 750" may result in insufficient pressure to seal chamber 666. Because of the smaller area/volume of protrusion 762, a smaller force may be required in order to exert a sealing pressure on X-ring seal 760". Therefore, as pressure from containment device 20, 20' decreases, X-ring seal 760" may maintain sealing of chamber 666 when desired, while an O-ring may less consistently maintain sealing under similar circumstances. The increased sealing accomplished by X-ring seal 760" may result in increased performance of regulator 40".

Although many of the features of regulator 40, 40', 40" are described as cylindrical, the shape of the elements are not limited thereto. Rather, the features may be any shape suitable for regulator 40, 40', 40" to properly regulate a fluid dispersion from containment device 20, 20'. Moreover, unless described otherwise, the structural elements of application device 30 and/or regulator 40, 40', 40" may be any material known in the art, including but not limited to a metal alloy, a ceramic, and/or a resin.

With reference to FIG. 12, a relief valve 62 according to an embodiment is shown. Relief valve 62 is positioned along second fluid path 48 between membrane regulator 44 and container 100 (housing 107 of container 100 is not shown in FIG. 12 for ease of understanding) to vent propellant fluid from containment device 20, 20' if, e.g., one or more of membrane regulator 44 or regulator 40 fails. For example, relief valve 62 includes a burst disc 62a that may rupture when a pressure at relief valve 62 is greater than a final, predetermined regulated pressure, e.g., a pressure of the propellant fluid after passing through properly functioning and properly adjusted regulator 40 and membrane regulator 44. A pressure at which burst disc 62a will burst may be approximately 20 PSI to 150 PSI, more preferably approximately 50 PSI to 70 PSI, and more preferably approximately 60 PSI. It will be understood that the burst pressure of burst disc 62a may be modified, or a burst disc 62a having a different burst pressure may be used, based on the desired output pressure from membrane regulator 44. It will also be understood that relief valve 62 is not limited to burst disc 62a, and may be any relief valve suitable for venting propellant fluid at a pressure greater than a desired output pressure such as, e.g., a pilot valve or the like. It will further be understood that relief valve 62 is not limited to being positioned as shown in FIG. 12, and may be positioned at any location between containment device 20, 20' and outlet 34 to prevent propellant fluid and/or a mixture of propellant fluid and material from being released from application device 30 above a desired pressure. Additionally, or alternatively, relief valve 62 may be placed at any position along a fluid path to release fluid pressure.

Figure 13:
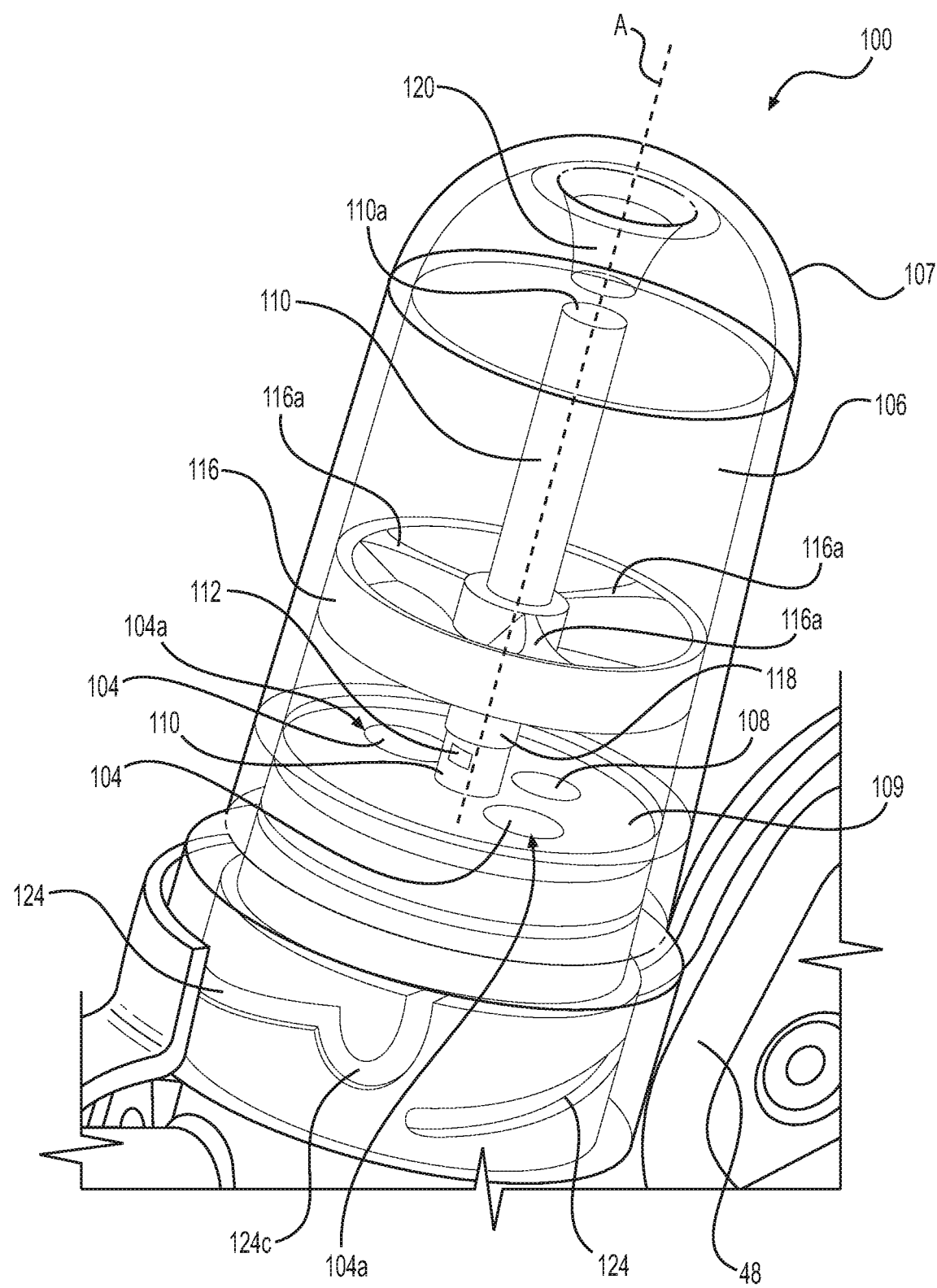
FIG. 13 is a perspective view of a chamber of the medical system of FIG. 1.

Container 100 according to an embodiment is shown in FIG. 13. As discussed above, container 100 may contain a powder, a fluid, or other substance to be mixed with the propellant fluid from containment device 20, 20' and dispensed through outlet 34 to catheter 190. Container 100 includes an inner chamber 106 defined by housing 107 of container 100 and a surface 109 of application device 30, which defines a bottommost surface of inner chamber 106. Inner chamber 106 contains the powder, fluid, or other substance. According to an example, housing 107 is a clear material to visualize inner chamber 106, but the invention is not limited thereto. Propellant fluid enters container 100 from second fluid path 48 via a chamber inlet 102 (see FIGS. 14A and 14B). Propellant fluid passes through filters 104 provided in filter holes 104a in bottommost surface 109 of inner chamber 106, which contains the powder or fluid, of container 100 (as described above, propellant fluid enters container 100 via the plurality of sixth pathway O via the filter holes 104a). While two filter holes 104a are shown in FIG. 13, container 100 may include any number of filter holes 104a, such as one to four filter holes 104a. Filters 104 may be sized to have holes approximately 25 to 50 microns in diameter to prevent powder or fluid from inner chamber 106 from passing from inner chamber 106 back through second fluid path 48, which may clog and/or contaminate application device 30.

With continued reference to FIG. 13, inner chamber 106 includes a chamber relief valve 108. Chamber relief valve 108 may be similar to relief valve 62 and may be, e.g., a burst disc or any other pressure relief valve known in the art. As with relief valve 62, chamber relief valve 108 relieves pressure when a pressure within application device 30, and specifically chamber 106, is greater than the final regulated pressure e.g., relief valve 108 burst pressure may be approximately 20 PSI to 150 PSI, more preferably approximately 50 PSI to 70 PSI, and more preferably approximately 60 PSI. While chamber relief valve 108 is provided in the bottommost surface of inner chamber 106, the location of relief valve 108 is not limited thereto. While not shown, relief valve 108 may vent propellant gas through a lumen provided in bottommost surface 109 of inner chamber 106.

A tube 110, such as a hypotube, extends from and generally perpendicular to bottommost surface 109 of inner chamber 106 toward a topmost surface of inner chamber 106, but it not limited to this configuration. As shown in FIGS. 12 and 13, a slot 112 is provided in, and through a wall of, tube 110 near the bottommost surface of inner chamber 106. Slot 112 is fluidly connected to a chamber outlet 114 (see FIGS. 14A and 14B), which connects to outlet 34, and allows a mixture of propellant fluid and the fluid or powder from inner chamber 106 to be dispensed from inner chamber 106 to outlet 34. Alternatively, or additionally, there may exist a plurality of slots 112 circumferentially arranged about a longitudinal axis A of tube 110, which may provide additional dispensing outlets from inner chamber 106. According to another example, slot 112 may be one or more circular (or other-shaped) holes provided in tube 110. The shape, number, and arrangement of slot 112 may aid in dispensing an appropriate amount of the propellant fluid and powder mixture from inner chamber 106 to chamber outlet 114, and the number of slots 112 may change according to a desired output. According to an example, the area of slot(s) 112 (either the area of a single slot 112 or the sum of the area of all slots 112) may be approximately 0.0025 square inches to 0.030 square inches, and more preferably 0.0046 square inches to 0.025 square inches, depending on the desired delivery rate of the propellant fluid and material mixture. Further, slot(s) 112 may be approximately 0.05 to 0.2 inches from filter holes 104a.

Container 100 may contain one or more spacers 216 (see FIG. 12) extending from the bottommost surface of inner chamber 106. Spacers 216 may alter the movement of material and/or propellant fluid through container 100, as will be described in greater detail below. It will be understood that container 100 may be formed without spacers 216.

As shown in FIGS. 13, 14A, and 14B, a ring or wheel-shaped attachment member 116 includes spokes 116a, is attached to and extends from a sheath 118 (described in detail below) and is attached to an inner surface of housing 107. Attachment member 116 connects sheath 118 to housing 107, such that a movement of housing 107 causes concurrent movement of sheath 118. Attachment member 116 (and spacers 216 in those embodiments that include spacers 216) may fill one or more voids within inner chamber 106 to alter the movement of materials therein. For example, attachment member 116 and spacers 216 may fill voids that would prevent material from properly mixing with the material located within inner chamber 106 and/or prevent the mixture from being appropriately dispensed through slot 112. Attachment member 116 and spacers 216 may further create new and/or additional pathways for the combination of propellant fluid and materials to take through inner chamber 106. For example, as shown in FIGS. 14A and 14B, spaces exist between the spokes 116a of attachment member 116, allowing propellant fluid and material to flow therebetween, while also changing the flow pattern of fluids and materials within container 100. These additional pathways may improve mixing of the propellant fluid with the materials and may ensure a more consistent amount of material is output from inner chamber 106.

With continued reference to FIG. 13, sheath 118 is provided on an outer surface of and coaxial with tube 110. Further, a conical member 120 is adjacent the topmost surface of inner chamber 106, and may be integrally formed with or otherwise fixed to housing 107. In a closed configuration, e.g., when inner chamber 106 is fluidly uncoupled from application device 30 as shown in FIG. 14A, sheath 118 covers and seals slot 112 and conical member 120 extends into and seals a distalmost end 110a of tube 110. This closed configuration prevents the material provided in inner chamber 106 from being contaminated and prevents the material from being dispensed before the physician is prepared to dispense the material. In contrast, when inner chamber 106 is in an open configuration and inner chamber 106 is fluidly coupled with application device 30, as shown in FIG. 14B, slot 112 is exposed and distalmost end 110a of tube 110 is open to inner chamber 106. The open configuration allows a mixture of propellant fluid and material in inner chamber 106 to be dispensed through slot 112 to outlet 34.

As further shown in FIG. 14A, one or more cams 122 are attached to an inner surface or an outer surface of housing 107 and are disposed in and movable along a cam shaft 124. Cam shaft 124 is ramp shaped and sloped downward from inner chamber 106 toward chamber inlet 102. In the closed configuration, achieved by twisting container 100 in the direction of arrow Y in FIG. 14A, cam 122 is disposed at a first end 124b of cam shaft 124, which is positioned near inner chamber 106. In the open configuration, achieved by twisting container 100 in the direction of arrow X in FIG. 14B, cam 122 is disposed at a second end 124a of cam shaft 124, which is opposite first end 124b, as shown in FIG. 14B. When container 100 is twisted in the direction of arrow X, housing 107 moves upward, as shown in FIG. 14B. Since attachment member 116 is attached to the inner side of housing 107, and since attachment member 116 is also attached to sheath 118, twisting container 100 in the direction of arrow X causes sheath 118 to also move upward and expose slot 112. Further, since conical member 120 is also attached to the inner side of housing 107, moving container 100 upward exposes distalmost end 110a of tube 110.

To attach housing 107 to application device 30, cam 122 is placed into the U-shaped groove 124c of cam shaft 124. Housing 107 may then be twisted as described above in the direction of arrow Y to close container 100, or in the direction of arrow X (from the closed position) to open container 100. According to an example, one or more O-rings and/or sealing members may be provided between housing 107 and application device 30 to assist in fluidly sealing housing 107 to application device 30.

A method of operating medical device 10 will now be explained. Application device 30 and/or containment device 20' may be packaged with container 100 attached thereto or, alternatively, may allow for container 100 to be attached to application device separately. After container 100 is attached to application device 30, containment device 20' may be attached to inlet 42. For example, containment device 20' may be attached to application device 30 using locking mechanism 50. According to an example, containment device 20' may be placed on a surface of piston 58 when lever 52 is in a first position, as shown in FIG. 4. Lever 52 is subsequently pushed toward handle 31 about pivot axis R, urging containment device 20' towards inlet 42 via attachment device 38. A pierce pin (not shown) on application device 30 breaks a seal (not shown) on containment device 20', causing containment device 20' and application device 30 to be in fluid communication. Lever 52 is held in a locked position when cam 57 rests in locking notch 56, which maintains a position of lever 52 adjacent handle 31 and maintains containment device 20' toward inlet 42.

With reference to FIG. 2, actuation of first actuator 36a and second actuator 36b may independently control release of propellant fluid through application device 30. For example, actuation of second actuator 36b causes propellant fluid to travel along first fluid path 46, i.e., through first pathway J, second pathway K, and fourth pathway L to outlet 34, as shown in FIG. 3. Use of this first fluid path 46 allows a user to purge material from outlet 34 and/or catheter 190, if catheter 190 is attached to application device 30 (see FIG. 2). The pressure of propellant fluid released in application device 30 may be controlled as described herein with reference to regulator 40.

With reference to FIGS. 14A and 14B, a user moves container 100 from a first position (FIG. 14A) to a second position (FIG. 14B) by turning container 100 in the direction X. As shown in FIG. 14B, slot 112 is exposed to inner chamber 106. Further, in the second position, the intermediate portion, including sixth pathways O and seventh pathway O', is fluidly coupled with the distal portion, including eighth pathway P, and the proximal portion, including first, third, and fifth pathways J, M, and N, of the second fluid path 48. Subsequently, a user actuates second actuation device 36a, causing propellant fluid to travel through the proximal portion of second fluid path 48 and into inner chamber 106. The propellant fluid mixes with a material, such as powder, in container 100, and the material and propellant mixture is expelled through slot 112 into the distal portion of second fluid path 48. The propellant fluid and material mixture exits application device at outlet 34, traveling down catheter 190 to distal end 193 (see FIG. 35). The user is able to direct the mixture to a target location by moving distal end 193 to different locations.

Figure 16:
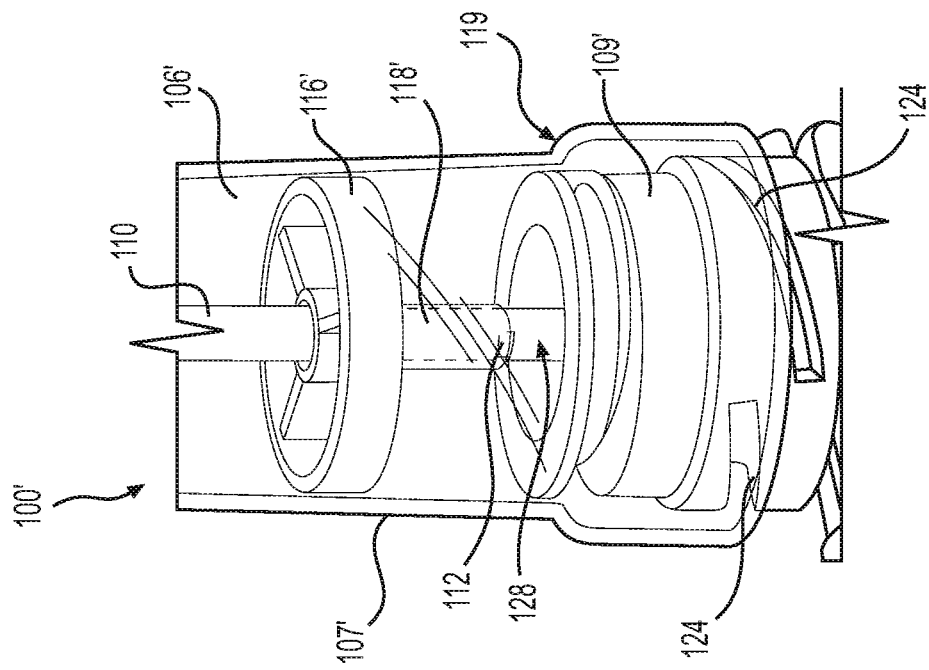
FIG. 16 shows a perspective view of the device of FIG. 15, in a second configuration.
Figure 15:
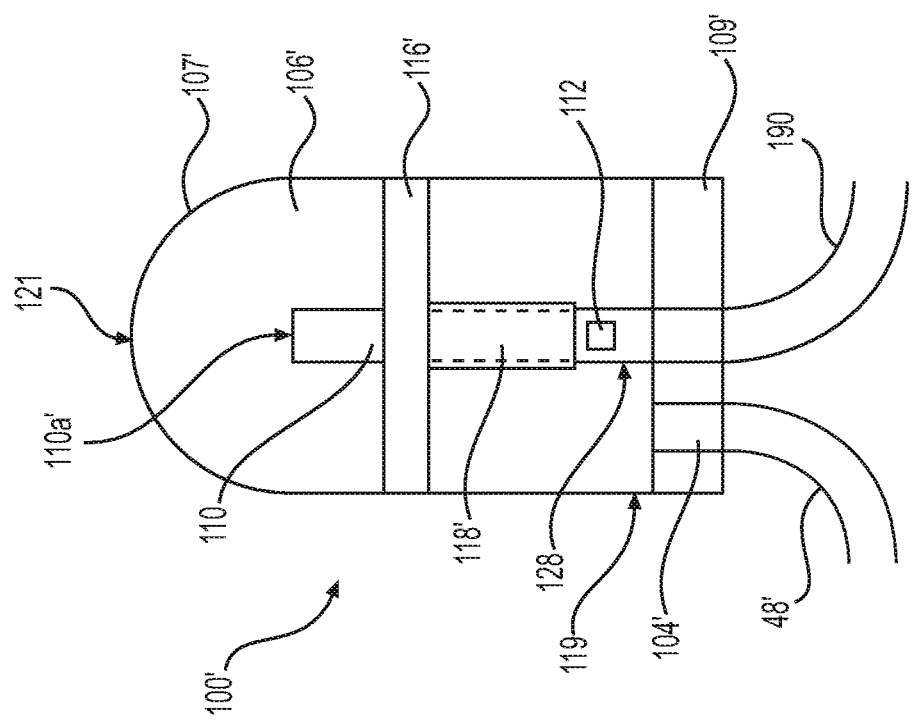
FIG. 15 shows a schematic view of a chamber according to another embodiment, in a first configuration.

Referring to FIGS. 15 and 16, device 100' for fluidizing and delivering a powdered agent (e.g., a powdered therapeutic agent) to a site within a living body (e.g., a target site) according to another embodiment. The device (e.g., container) 100' according to an example further comprises an overtube (e.g., a sheath) 118' movably mounted over a portion of the tube 110 so that the overtube 118' may be moved along a length of the tube 110 to extend over the slot 112, controlling a size of an opening of the slot 112. Testing has shown that increasing the slot size increases the powder delivery rate while decreasing the slot size decreases the powder delivery rate. The overtube 118' is movable relative to the tube 110 from an initial configuration, in which the overtube 118' at least partially covers the slot 112 toward an open configuration, in which the overtube 118' is moved along a length of the tube 110 to gradually increase the size of the slot 112 during the course of the treatment procedure so that the rate of delivery of the fluidized powder delivery may be maintained above a threshold level (e.g., be held substantially consistent over time) even as a volume of the powdered agent within the canister 107' decreases as the powder is dispensed. It will be understood that a fluidized powder/material includes, but is not limited to, a powder/material that acquires the characteristics of a fluid by passing a propellant fluid (such as a gas) with in or through it, and also an agitated powder/material which is a material that follows a propellant fluid or is pushed by a propellant fluid.

According to an embodiment, a target delivery rate may be, for example, greater than 1 gram for every 5 seconds of delivery. The device 100' may provide the best delivery results when the canister 107' is approximately 45% to 80% filled with the powdered agent. For example, at 80% fill the target rate may be sustained for 30 delivery seconds. This delivery rate is also dictated by the amount of gas that the device 100' may use for delivery. By gradually increasing the size of the slot 112 through which the fluidized powder mixture may exit the canister 107', the delivery rate may be maintained (e.g., past 30 delivery seconds) even as the volume of the powdered agent within the canister 107' decreases.

The canister 107' in this embodiment extends longitudinally from an open first end 119 to a closed second end 121 to define the inner chamber 106', which is configured to receive the powdered agent therein. A lid (e.g., a surface) 109' is coupled to the first end 119 to enclose the inner chamber 106' and prevent the powdered agent and/or gas from leaking from the inner chamber 106'. In one embodiment, the lid 109' is received within the first end 119 and coupled thereto. The inlet (e.g., filter hole) 104' and/or an outlet (via slot 112) in this embodiment are configured as openings extending through the lid 109'. It will be understood by those of skill in the art, however, that the inlet 104' and the outlet may have any of a variety of configurations so long as the inlet 104' and the outlet are connectable to a gas source and a delivery member, respectively, for supplying a high flow gas to the powdered agent to fluidize the powdered agent and deliver the fluidized powder mixture to the target site. For example, the inlet 104' may be coupled to a connecting member (e.g. second fluid path) 48' which connects the gas source to the inlet 104'. In an embodiment, gas may be supplied to the canister 107' at a pressure ranging from between 5 and 20 psi and/or a flow rate of 8-15 standard liters per minute. The outlet in this embodiment is coupled to catheter 190' sized, shaped and configured to be inserted through a working channel of a flexible endoscope to the target site within a living body. In one example, catheter 190' may have an inner diameter between 0.065 inches and 0.11 inches. In another embodiment, the inlet 104' and the outlet may extend through a portion of the canister 107'.

The tube 110 extends from a first end 128 connected to the outlet to a second end (e.g., distalmost end) 110a' extending into the interior space 106'. As described above, the tube 110 in FIGS. 15 and 16 also includes a slot 112, which extends through the wall of the tube 110. The slot 112 in this embodiment is positioned proximate the first end 128 so that the fluidized powder mixture may exit the interior space 106' of the canister 107' via one of second end 110a' of the tube 110 and the slot 112 proximate the first end 128.

The overtube 118' is movably mounted over a portion of a length of the tube 110. The overtube 118' is movable relative to the tube 110 so that, as the overtube 118' moves over the tube 110, an area of the slot 112 covered by the overtube 118' is varied to control a size of a portion of the slot 112 exposed to the interior space 106' and through which the fluidized powder mixture may exit the interior space 106' of the canister 107'. For example, in an initial configuration, the overtube 118' extends over the entire slot 112 so that the slot 112 is completely covered, preventing any fluidized powder mixture from exiting therethrough. During the course of treatment of the target site, however, the overtube 118' may be moved relative to the tube 110 to increase the size of the portion of the slot 112 exposed and through which the fluidized powder may exit to maintain the delivery rate of the fluidized powder mixture at a desired level (e.g., above a threshold delivery rate). For example, FIG. 16 shows the slot 112 partially covered via a portion of the overtube 118' and FIG. 15 shows the slot 112 entirely exposed. Although the embodiment describes an initial configuration in which the entire slot 112 is covered, it will be understood by those of skill in the art that, in an initial configuration, the overtube 118' may have any of a variety of positions relative to the slot 112, so long as the size of the slot 112, through which the fluidized powder may exit, is increased during the course of treatment as the powder in the canister 107' is dispensed.

It will also be understood by those of skill in the art that the overtube 118' may be moved relative to the tube 110 via any of a variety of mechanisms. In one embodiment, the overtube 118' may be connected to a stabilizing ring 116' which extends, for example, radially outward from the overtube to an interior surface of the canister 107' to fix a position of the overtube 118' relative to the canister 107'. The canister 107' and the tube 110 in this example are rotatably coupled to one another so that, when the canister 107' is rotated relative to the tube 110, the overtube 118' correspondingly rotates about the tube 110 while also moving longitudinally relative to the tube 110 to increase (or decrease, depending on the direction of rotation) a size of the slot 112 through which the fluidized powder mixture may exit. In one example, the lid 109', from which the tube 110 extends, includes cam paths 124 extending along a partially helical path, within which an engaging feature (e.g., protrusion 122 in FIGS. 14A and 14B) of the canister 107' rides so that, as the canister 102 and, consequently, the overtube 118' are rotated relative to the lid 109' and the tube 110, the overtube 118' moves longitudinally relative to the tube 110. As would be understood by those skilled in the art, the cam paths 124 and the corresponding engaging features of the canister 107' function similarly to a threaded engagement between the canister 107' and the lid 109' to achieve the desired relative movement between the overtube 118' and the tube 110.

Although the embodiment describes the size of the portion of the slot 112 available for fluidized powder mixture to exit as controlled via the overtube 118', the size of the slot 112 may be controlled via any "door" having any of a variety of structures and geometries so long as the "door" may be gradually opened during the course of a treatment procedure to maintain a desired flow rate of therapeutic agent out of the canister 107'. Movement of the overtube 118' or any other "door" may be actuated mechanically, e.g., by physically twisting the overtube 118', or may be actuated pneumatically by the flow of gas. In addition, although the embodiment shows and describes a single slot 112, the tube 110 may include more than one slot 112, which may be covered and/or exposed, as desired, via any of a number of door mechanisms, as described above.

According to an example method using the device 100', the canister 107' is filled with a powdered agent such as, for example, a hemostatic agent, prior to assembly of the device 100'. Upon filling the canister 107' with a desired amount of powdered therapeutic agent, the canister 107' is assembled with the lid 109' to seal the powdered agent therein. The inlet 104' is then coupled to the gas source via, for example, the connecting member 48' and the outlet is coupled to the catheter 190'. The catheter 190' is then inserted to the target site within the living body (e.g., through a working channel of a delivery device such as, for example, an endoscope). High flow gas is introduced into the interior space 106' of the canister 107' to form the fluidized powder mixture. The user may depress a trigger or other controller to spray the fluidized mixture and to deliver the fluidized mixture to the target are (e.g., a bleeding site) to provide treatment thereto. As the fluidized powder mixture is being delivered to the target site, the user may physically rotate the canister 107' relative to the tube 110 to increase the size of the slot 112 through which the fluidized mixture is exiting the interior space 106' to maintain a desired flow level. Alternatively, if a trigger is being used to control delivery of the fluidized powder mixture, when the trigger is depressed, a pneumatic cylinder or motor may be operated to rotate and move the lid 109' relative to the canister 107' so that a larger cross-sectional area of the slot 112 is exposed, increasing the size of the slot 112 through which the fluidized mixture may exit the interior space. Thus, as a volume of the powdered agent within the canister 107' is decreased, the cross-sectional area of the slot 112 that is exposed is increased to maintain a substantially constant delivery rate of the fluidized powder mixture. Alternatively, sensors may detect a flow rate and automatically control the opening of the slot 112 to ensure that a desired flow rate is maintained.

Figure 17:
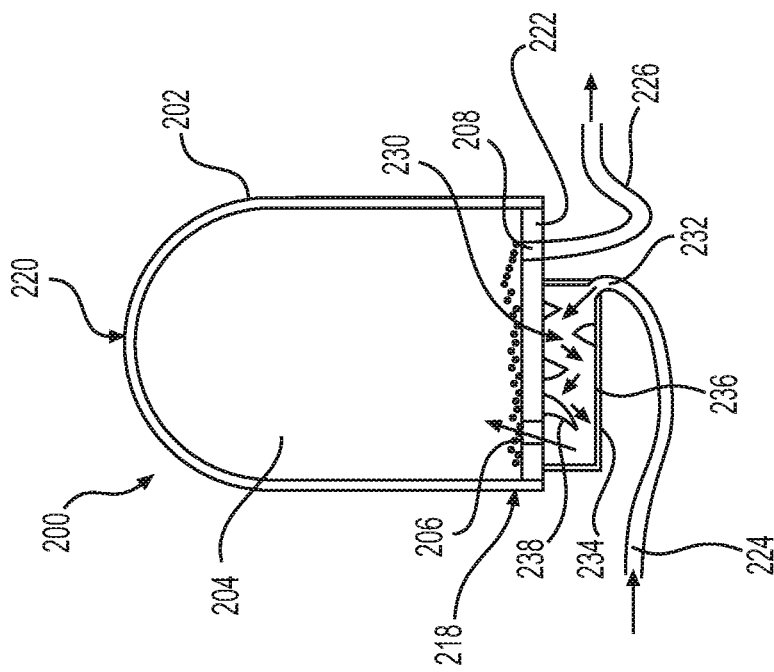
FIG. 17 shows a schematic view of a device according to another embodiment of the present disclosure.

A device 200 according to another embodiment of the present disclosure, shown in FIG. 17, is substantially similar to the device 100' as described above unless otherwise indicated. The device 200 comprises a canister 202 defining an interior space 204 within which a powdered agent is received. Similarly to the device 100, 100', the interior space 204 is enclosed via a lid 222 coupled thereto so that the powdered agent contained within the interior space 204 forms a fluidized powder mixture when the interior space 204 is supplied with a high flow gas via an inlet 206. The fluidized powder mixture exits the interior space 204 via an outlet 208 to be delivered to a target site within a patient during treatment. To maintain a desired delivery rate as the volume of the powdered agent in the interior space 204 decreases during the course of treatment, the lid 222 includes a turbulator plate 230. As gas passes through the turbulator plate 230, the turbulator plate 230 vibrates and/or rattles to prevent, or at least reduce, settling of the powdered agent contained within the canister 202. Without the turbulator plate 230, during the course of treatment, some powdered agent would otherwise settle into an equilibrium state, resisting fluidization and making it difficult to maintain a desired delivery rate of the therapeutic agent.

Similarly to the canister 107', the canister 202 extends longitudinally from an open first end 218 to a closed second end 220 to define the interior space 204. The lid 222 is coupled to the first end 218 to enclose the interior space 204 and contain the powdered agent therein. The inlet 206 and the outlet 208 are configured as openings extending through the lid 222 in communication with the interior space 204. Although not shown, similarly to the device 100', the outlet 208 includes a tube extending therefrom and into the interior space 204 to allow the fluidized powder mixture to exit via the tube and the outlet 208.

The turbulator plate 230 in this embodiment extends along a portion of the lid 222 which faces away from the interior space 204. In this embodiment, the turbulator plate 230 includes an opening 232 extending through a wall 234 thereof, the opening 232 being configured to be connected to a gas source via, for example, a connecting element 224. The turbulator plate 230 extends along the lid 222 so that the opening 232 is in communication with the inlet 206. Thus, gas passes through the turbulator plate 230 and into the interior space 204 via the inlet 206. An interior 236 of the turbulator plate 230 includes a plurality of structures 238 such as, for example, ribs, bumps or bosses, which cause the flow of gas therethrough to be turbulent, imparting a vibratory response in the turbulator plate 230. The vibration in turn prevents the powdered agent from settling on the lid 222. Thus, the flow of gas through the turbulator plate 230 and into the interior space 204 causes both the vibration of the turbulator plate 230 and the fluidization of the powered agent within the canister 202. A magnitude of the vibration may be controlled via control of the rate at which gas is passed through the turbulator plate 230 as would be understood by those skilled in the art. In this embodiment, the magnitude of vibration of the turbulator plate 230 is held constant over time, for as long as the user is depressing a trigger to feed gas to the canister 202. The fluidized powder agent exits the canister 202 via the outlet 208, which is not in communication with the interior 236 of the turbulator plate 230. The outlet 208 in this embodiment is coupled to a delivery catheter 226 for delivering the fluidized powder mixture to the target site.

Figure 18:
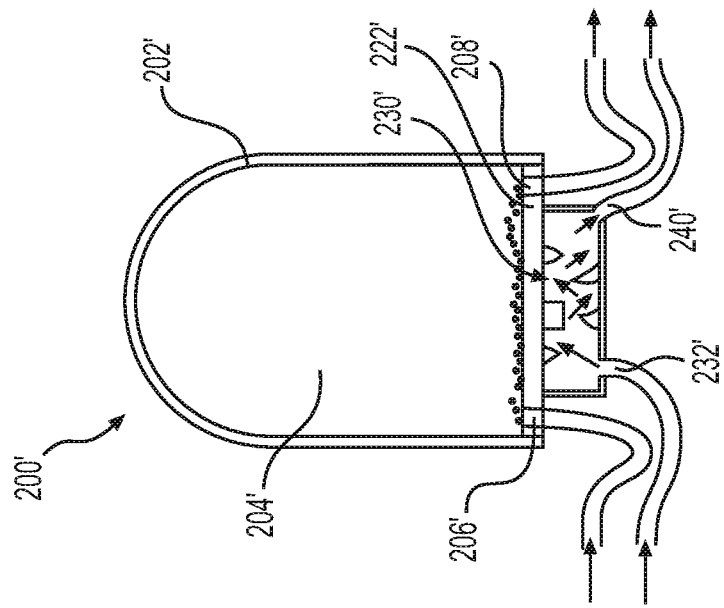
FIG. 18 shows a schematic view of a device according to an alternate embodiment of the present disclosure.

In an alternate embodiment, as shown in FIG. 18, a device 200' is substantially similar to the device 200 described above, unless otherwise indicated. In this embodiment, a turbulator plate 230' extends along a portion of a lid 222', which encloses an interior space 204' defined via a canister 202', and includes a first opening 232' and a second opening 240' extending through a wall 234' thereof. Neither the first opening 232' nor the second opening 240' are in communication with an inlet 206' and an outlet 208' of the device 200'. Each of the inlet 206' and the first opening 232' are configured to be connected to a gas source for supplying gas to the interior space 204' and the turbulator plate 230', respectively. Each of the inlet 206' and the first opening 232' is connected to the same or different gas sources.

Gas supplied to the turbulator plate 230' via the first opening 232' passes through the turbulator plate 230' and exits the turbulator plate 230' via the second opening 240'. Gas may, for example, be supplied to the turbulator plate 230' at a constant rate while the powdered agent is being fluidized and delivered to the target site to maintain a constant magnitude of vibration. Alternatively, the flow of gas supplied to the turbulator plate 230' may be changed over time, or intermittently, to change a magnitude of vibration, as desired, to optimize the rate of delivery of the fluidized powder mixture. It will be understood by those of skill in the art, however, that the function of the turbulator plate 230' remains otherwise the same as the device 200, keeping the powdered agent from settling on the lid 222'.

Figure 20:
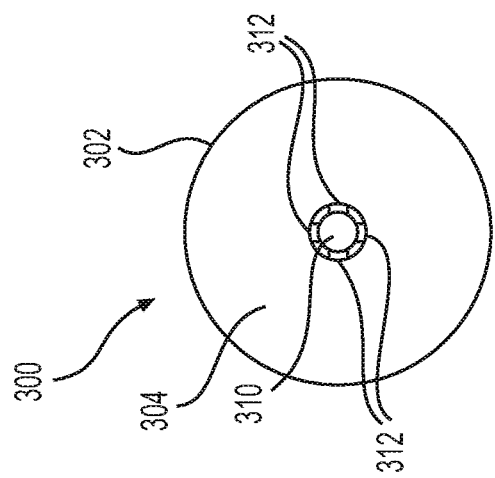
FIG. 20 shows a lateral cross-sectional view of the device of FIG. 19 along the line 19-19.
Figure 19:
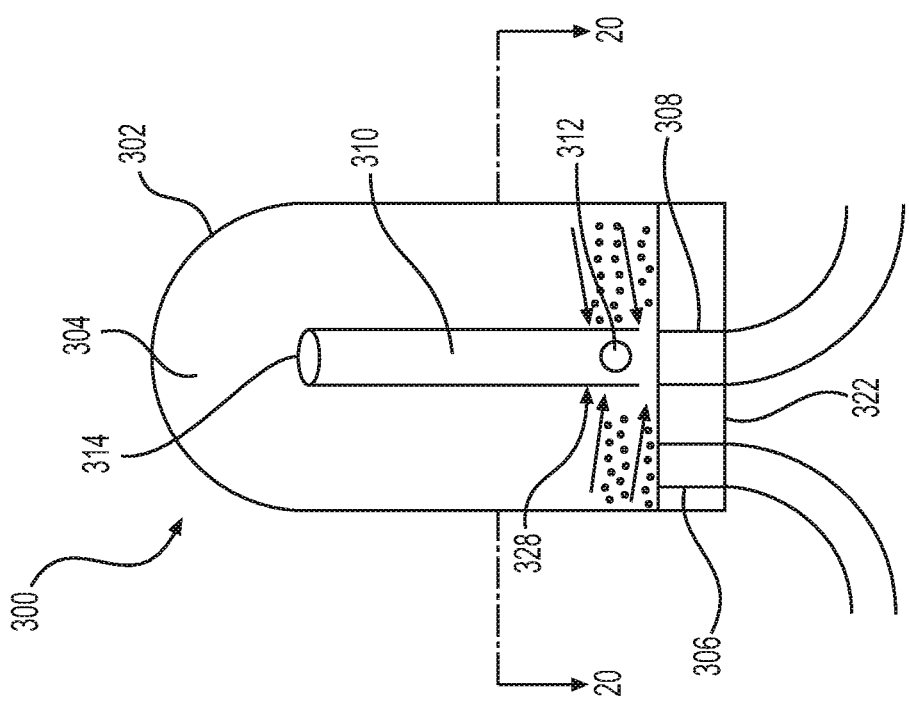
FIG. 19 shows a schematic view of a device according to yet another embodiment of the present disclosure.

As shown in FIGS. 19 and 20, a device 300 according to another embodiment of the present disclosure is substantially similar to the devices 100', 200, unless otherwise indicated. The device 300 comprises a canister 302 defining an interior space 304 within which a powdered agent (e.g., hemostatic agent) is received and fluidized via a high flow gas for delivery to a target site (e.g., bleeding site) for treatment. The interior space 304 is enclosed via a lid 322 attached to an open end of the canister 302 and gas is supplied to the interior space 304 via an inlet 306 extending through the lid 322. The resulting fluidized powder mixture exits the interior space 304 via an outlet 308 extending through the lid 322 to be delivered to the target site. The device 300 also includes a tube 310 extending from a first end 328 connected to the outlet 308 to a second end 314 extending into the interior space 304. Rather than a single slot extending through a wall of the tube 310, however, the tube 310 includes a plurality of slots 312 distributed about the tube 310 to prevent uneven distribution of powder within the canister 302 and prevent powder build up on any side of the tube 310, which may decrease fluidized powder mixture delivery rates.

In one embodiment, as shown in FIG. 20, the tube 310 includes four slots 312, distributed about the tube 310 and spaced equidistantly from one another. The slots 312 in this embodiment are positioned proximate the first end 328. It will be understood by those of skill in the art, however, that the number, position and configuration of the slots 312 may be varied.

Figure 21:
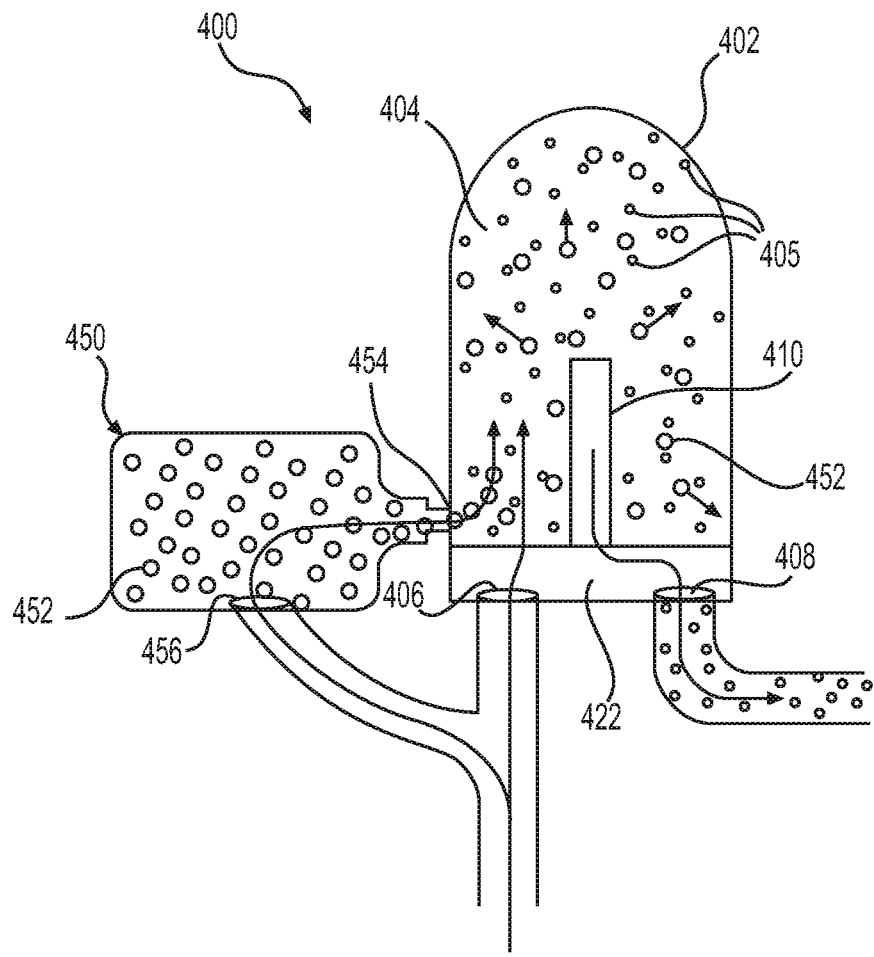
FIG. 21 shows a schematic view of a device according to another embodiment of the present disclosure.

As shown in FIG. 21, a device 400 according to another embodiment of the present disclosure is substantially similar to the devices 100', 200, and 300 described above, unless otherwise indicated. The device 400 comprises a canister 402 defining an interior space 404 within which a powdered agent 405 is received and fluidized to form a fluidized powder mixture for delivery to a target site of within a living body. Similarly, the device 400 may include a lid 422 enclosing the interior space 404 along with an inlet 406 via which gas is supplied to the interior space 404 to fluidize the powdered agent 405 and an outlet 408 via which the fluidized powder agent exits the canister 402 to be delivered to the target site. The device 400 may also include a tube 410 extending into the interior space 404 in communication with the outlet 408. The device 400 further comprises a filler chamber 450 coupled to the canister 402, in communication with the interior space 404 of the canister 402. The filler chamber 450 houses filler material 452 such as, for example, mock particles, beads, tiny "bounce balls" or a foam material, which is injected into the canister 402 as fluidized powder mixture exits the canister 402 to make up for a loss in volume of the powdered agent as the fluidized powder mixture is delivered to the target site. The filler material 452 is injected into the canister 402 to maintain a constant ratio of volume of material (e.g., powdered agent and filler) to volume of gas within the canister 402 to maintain a desired rate of delivery of the fluidized powder mixture to the target site.

The filler chamber 450 may be connected to the canister 402 so that the filler material 452 passes from the filler chamber 450 to the canister 402 via a filler inlet 454. In one embodiment, the filler chamber 450 may also include a gas inlet 456 so that, when a user actuates the delivery of the fluidized powder mixture to the target site via, for example, pressing a trigger, gas is supplied to both the canister 402 and the filler chamber 450. The gas supplied to the filler chamber 450 drives the filler material 452 out of the filler chamber 450 into the canister 402. The filler chamber 450 may include a pressure regulator to regulate the gas inlet pressure, as necessary, to regulate the volume of filler material 452 being supplied to the canister 402 to correspond to the volume of powdered agent 405 exiting the canister 402. In one embodiment, the filler inlet 454 may be sized, shaped and/or otherwise configured to facilitate passage of a single stream of filler material 452 (e.g., beads) therethrough into the canister 402.

Filler material 452 is configured to be able to enter the interior space 404 of the canister 402, but is prevented from exiting the canister 402 during delivery of the fluidized powder mixture. In one embodiment, this is achieved via a sizing of the individual particles of the filler material 452. For example, the filler material 452 may be sized and/or shaped to prevent it from entering the tube 410 and/or the outlet 408. In other words, each bead or particle of the filler material 452 is selected to be larger than an opening of the tube 410 and/or an opening of the outlet 408. The filler material 452 is sized and shaped to be large enough to prevent the filler material from exiting the canister 402, while also being configured to bounce off walls 403 of the canister 402 as the powdered agent is moved within the interior space 404 and is fluidized to prevent clogging of the device 400.

Thus, in use, the canister 402 of the device 400 loses powder during delivery of the fluidized powder agent, but will compensate for the loss by simultaneously supplying the canister 402 with a corresponding volume of filler material 452. The rate of delivery of filler material 452 into the canister 402 may be determined by calculating a powder volume that has been lost given a fluidized powder mixture delivery rate, and adjusting it based on volume and flow rate differences of the filler material 452 versus the powdered agent 405. The rate of delivery of filler material 452 into the canister 402 is selected to compensate for the loss in volume of the powder 405 to maintain a substantially constant fluidized powder mixture delivery rate. Although the inlet 406 of the canister 402 and the gas inlet 456 of the filler chamber 450 are shown and described as coupled to a single gas source, it will be understood by those of skill in the art that each of the inlet 406 and the gas inlet 456 may be coupled to separate gas sources, each of which supply gas to the inlet 406 and the gas inlet 456 when delivery of fluidized powder mixture to the target site is actuated and/or triggered.

As shown in FIGS. 22 and 23, a device 500 may be substantially similar to the device 400, unless otherwise indicated. The device 500 comprises a canister 502 defining a first interior space 504 within which powdered agent is received and fluidized to deliver a fluidized powder mixture to a target site of a patient for treatment. Rather than a separate filler chamber, however, the canister 502 defines both the first interior space 504 and a second interior space 550 which, when the device 500 is in an operative position, extends above the first interior space 504. In addition, rather than filling the first interior space 504 with a filler material to maintain a constant volume of material (powder and/or filler) therein, the second interior space 550 houses additional powdered agent, which may be supplied to the first interior space 504 via gravity as the fluidized powder mixture exits the first interior space 504 to be delivered to the target site. An inlet and outlet (not shown) are in communication with the first interior space 504 so that only the powdered agent contained within the first interior space 504 is fluidized to form the fluidized powder mixture and only the powdered agent within the first interior space 504 is permitted to exit the device 500 to the target site.

The second interior space 550 may be in communication with the first interior space 504 via an opening 554 extending therebetween. The device 500 further comprises a door 558 movable between a first configuration prior to commencement of a treatment procedure, as shown in FIG. 22, and a second configuration during a course of treatment, as shown in FIG. 23. In the first configuration, the door 558 may extend over the entire opening 554 when fluidized powder mixture is not being delivered, to prevent the passage of any powdered agent from the second interior space 550 to the first interior space 504. As shown via the dotted line in FIG. 22, the first interior space 504 contains a given volume of powdered agent therein.

When the user actuates and/or triggers delivery of the fluidized powder mixture, as shown in FIG. 23, movement of the door 558 may also be triggered so that the door 558 opens to expose the opening 554, permitting the passage of powdered agent from the second interior space 550 to the first interior space 504. Actuation of the door 558 may be triggered in any of a number of different ways. For example, the door 558 may include a motor that is activation, upon actuation of the device 500, a magnetic mechanism that uses magnetism to open the door 558 upon activation and/or pressure differentials created by the pressure increase upon device actuation. The second interior space 550 may include an angled surface 560 which directs the powdered agent toward the opening 554 so that, when the door 558 is open, the powdered agent within the second interior space 550 is permitted to fall into the first interior space 504. Thus, the first interior space 504 is passively fed with the additional powdered agent via gravity. As shown via the dotted line in FIG. 23, the volume of powder within the first interior space 504 should remain constant during the course of treatment since the first interior space 504 is being fed via the second interior space 550 as the fluidized powder mixture is being delivered. The opening 554 may be sized and/or otherwise configured to allow powdered agent to fall therethrough at a controlled rate selected to keep the volume of powdered agent within the first interior space 504 substantially constant.

Figure 25:
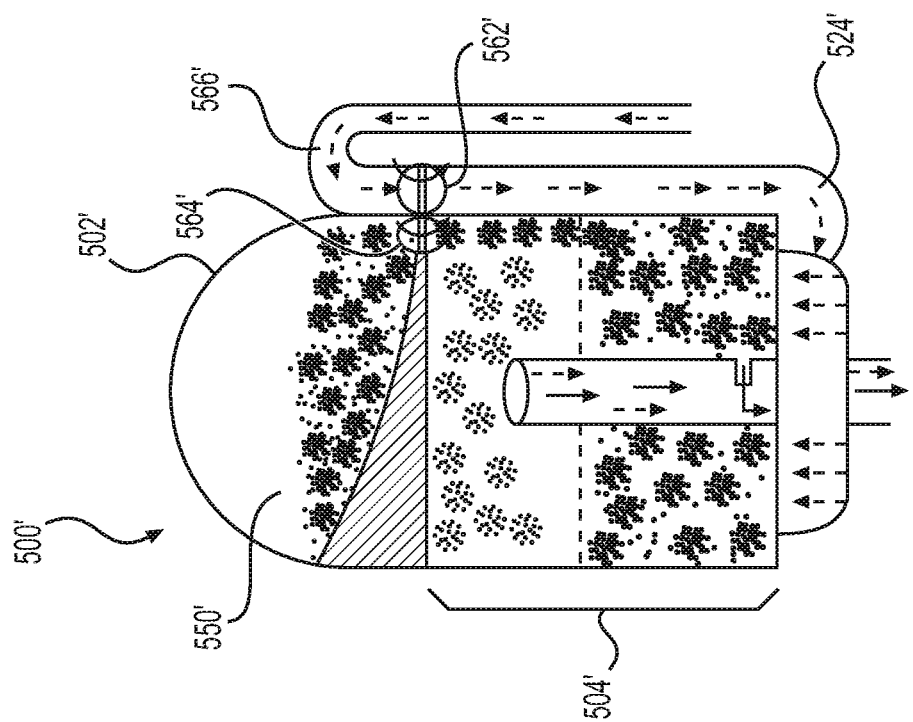
FIG. 25 shows a schematic view of the device of FIG. 24, in a second configuration.
Figure 24:
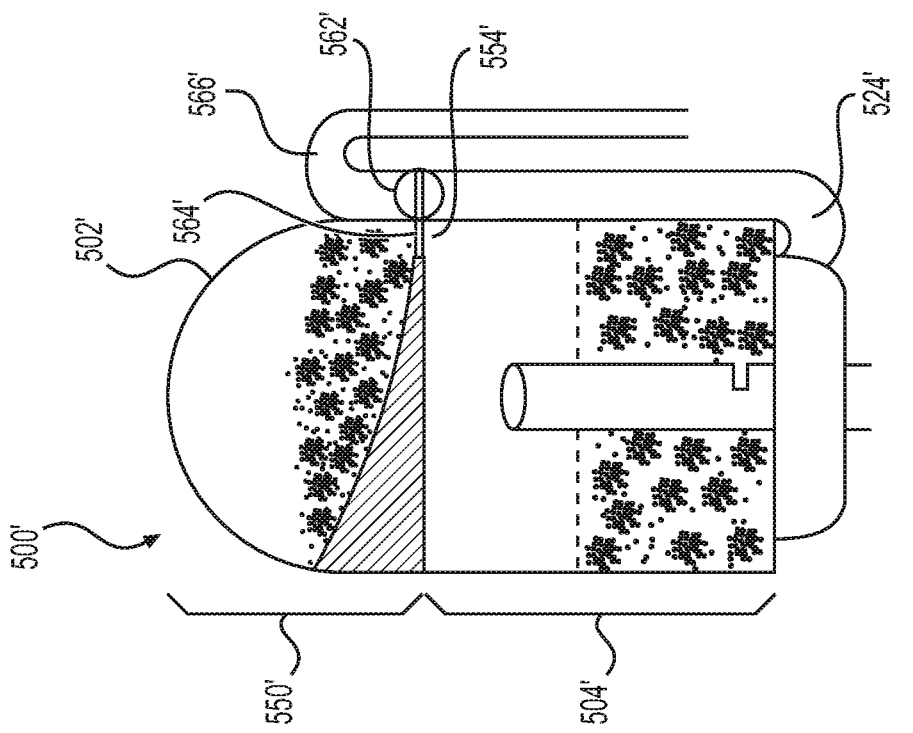
FIG. 24 shows a schematic view of a device according to an alternate embodiment of the present disclosure, in a first configuration.

Although the additional powdered agent within the second interior space 550 is described as being passively fed into the first interior space 504 via gravity, in an alternate embodiment, as shown in FIGS. 24 and 25, powdered agent within a second interior space 550' of a canister 502' of a device 500' may be actively fed into a first interior space 504' of the canister 502' via, for example, a turbine 562' which may be powered via a gas flow. In this embodiment, a rotatable paddle 564' is mounted within an opening 554' extending between the first and second interior spaces 504', 550'. The rotatable paddle 564' is connected to the turbine 562', which is positioned along an exterior of the canister 502' and housed within a gas flow path 566'. The gas flow path 566' may be configured as a connecting element 524' connecting a gas source to an inlet (not shown), which permits passage of gas therethrough into the first interior space 504. Thus, the connecting element 524', in this embodiment, extends along an exterior side of the canister 502' to accommodate the turbine 562'.

In a first configuration of device 500', as shown in FIG. 24, in which delivery of fluidized powder mixture is not actuated and thus no gas flows through the flow path 566', the turbine 562' does not rotate and thus no powdered agent is permitted to pass from the second interior space 550' to the first interior space 504'. As shown in FIG. 25, when delivery of the fluidized powder mixture is actuated, in a second configuration, the turbine 562' is rotated via a flow of gas passing through the gas flow path 566'. Rotation of the turbine 562' correspondingly rotates the paddle 564' to actively drive the powdered agent within the second interior space 550' through the opening 554' and into the first interior space 504'. Since the flow of gas is initiated when a user actuates and/or otherwise triggers delivery of a fluidized powder mixture to a target site, a supply of powdered agent from the second interior space 550' to the first interior space 504' will occur simultaneously with the exiting of powdered agent (e.g., the fluidized powder mixture) from the first interior space 504' to maintain a substantially constant volume of powdered agent within the first interior space 504'. Maintaining the volume of powdered agent within the first interior space 504' will correspondingly maintain a substantially constant delivery rate of the fluidized powder mixture.

Although the above embodiment describes a single gas source/supply, it will be understood by those of skill in the art that the turbine 562' may be driven via a gas source separate from a gas source connected to an inlet of the device 500' so long as a volume of powdered agent supplied from the second interior space 550' to the first interior space 504' corresponds to a volume of powdered agent exiting the first interior space 504'. In addition, although the embodiment describes active transfer of the powdered agent via a gas powered turbine, active transfer from the second interior space 550' to the first interior space 504' may also occur via other mechanisms.

As shown in FIG. 26, a device 1200 for fluidizing and delivering a powdered agent (e.g., hemostatic agent) according to an embodiment of the present disclosure comprises a canister 1202 and a piston 1204 movably coupled to the canister 1202. The canister 1202 is configured to receive the powdered agent within an interior space 106 thereof. The canister 1202 is subsequently filled with a gas via an inlet 1208 that may be connected to a gas source via, for example, a tubular member 1212. The powder is fluidized via the gas to form a two-phase mixture that may be sprayed onto the target site (e.g., bleeding site) via a catheter 1214 connected to an outlet 1210. The catheter 1214 is sized and shaped and sufficiently flexible to be endoscopically inserted into a patient body to the target site (e.g., along a tortuous path traversed by a flexible endoscope through a body lumen accessed via a natural body orifice). In order to maintain a substantially constant delivery rate of the mixture to the target site, the piston 1204 is movable relative to the canister 1202 to decrease a volume of the interior space 1206, during the course of treatment of the target site. Thus, as a volume of powder within the canister 1202 is decreased, the volume of the interior space 1206 is also decreased to maintain a substantially constant powder volume to canister volume ratio. The piston 1204 may be moved relative to the canister 1202 in any of a number of different ways. In this embodiment, the piston 1204 is moved via a pneumatic cylinder or motor 1216.

The canister 1202 of this embodiment is formed of a rigid material to define the interior space 1206, which is configured to receive the powdered agent along with the gas to form the gaseous fluid mixture that is sprayed on the target site to provide treatment thereto. The canister 1202 extends longitudinally from an open first end 1216 to a closed second end 1218. The piston 1204 is movably coupled to the canister 1202 at the first end 1216 and is movable toward the second end 1218 to reduce the volume of the interior space 1206. The piston 1204 encloses the interior space 1206 so that the powder, gas and/or the gas mixture do not leak from the canister 1202, and exit the canister 1202 via the outlet 1210 and from there into the catheter 1214 to exit toward the target site. Thus, the piston 1204 of this embodiment is received within the open first end 1216 and is substantially sized and shaped to correspond to a size and shape of an opening at the first end 1216. In one example, the canister 1202 is substantially cylindrical while the piston 1204 is substantially disc-shaped to be received within the open first end 1216 of the canister 1202. The canister 1202 is sized and shaped so that the piston 1204 is movable along at least a portion of a length thereof toward the second end 1218 to reduce a volume of the interior space 1206 while also preventing leakage of any fluids/substances received within the interior space 1206. In one example, the piston 1204 includes a sealing ring extending about a circumference thereof to prevent leakage of any powder, gas and/or fluid therepast.

As described above, the device 1200 also includes the inlet 1208 via which gas is introduced into the interior space 1206 and the outlet 1210 via which the fluidized powder is delivered to the catheter 1214 to reach the target site. In one embodiment, each of the inlet 1208 and the outlet 1210 are configured as an opening extending through a portion of the piston 1204 to be connected to the tubular member 1212 and the catheter 1214, respectively. It will be understood by those of skill in the art, however, that the inlet 1208 and the outlet 1210 may be positioned on or along any portion of the canister 1202 and/or the piston 1204 so long as the inlet 1208 is configured to receive a high pressure gas therethrough and into the interior space 1206, and the outlet 1210 is connectable to a delivery element such as, for example, the catheter 1214, which delivers the fluidized mixture from the interior space 1206 to the target site. It will also be understood by those of skill in the art, that although the inlet 1208 is described as connected to the gas source via the tubular member 1212, the inlet 1208 may be connected to the gas source via any of a number of couplings so long as sufficient gas flow is deliverable therethrough. In addition, although the outlet 1210 is shown and described as an opening extending through the piston 1204, it will be understood by those of skill in the art that the outlet 1210 may also be configured to include a hypotube extending into the interior space 1206 so that fluidized mixture formed within the interior space 1206 may be received within the hypotube to be delivered to the target site via the catheter 1214.

In this embodiment, the piston 1204 is movable relative to the canister 1202 via a pneumatic cylinder or motor 1220. The device 1200 may be programmed to include one or more inputs such as, for example, time. When it is desired to deliver the fluidized mixture to the target site, the user may initiate delivery using a controller such as a trigger. For example, when the user depresses the trigger to deliver the fluidized mixture, the piston 1204 moves toward the second end 1218 at a preset rate. When the user releases the trigger, the piston 1204 may stop, maintaining its position relative to the canister 1202 until the user depresses the trigger again. Alternatively or in addition, the device 1200 may use other inputs such as, for example, inputs based on flow and/or pressure sensors within the interior space 1206 of the canister 1202, the inlet 1208 and/or the outlet 1210.

Although the piston 1204 of the device 1200 is described and shown as driven via the pneumatic cylinder or motor 1220, it will be understood by those of skill in the art that the piston 1204 may be moved from its initial position proximate the first end 1216 toward the second end 1218 via any of a variety of different drive mechanisms, examples of which will be described in further detail below. In addition, although the piston 1204 is shown as forming a base (e.g., bottom portion) of the canister 1202, it will be understood by those of skill in the art that the piston 1204 may be coupled to the canister 1202 in any of a number of configurations. In particular, the piston 1204 may also be configured as a lid (e.g., top portion) of the canister 1202. In a further embodiment, the device 1200 may include more than one piston 1204, each of which are movable relative to the canister 1202 to reduce the volume of the interior space 1206 thereof.

According to example method using the device 1200, the canister 1202 may be filled with the powdered agent such as, for example, a hemostatic agent, prior to assembly of the device 1200. Upon filling the canister 1202 with a desired amount of powder, the canister 1202 and the piston 1204 are assembled, the inlet 1208 is coupled to the gas source via, for example, the tubular member 1212, and the outlet 1210 is coupled to the catheter 1214. The catheter 1214 may then be inserted to the target site within the body through a working channel of a delivery device such as an endoscope. The user may depress a trigger or other controller to introduce a high flow gas into the interior space 1206 of the canister 1202 to form the fluidized mixture and deliver the fluidized mixture to the target site (e.g., a bleeding site) to provide treatment thereto. When the trigger is depressed, the pneumatic cylinder or motor 1220 is operated to move the piston 1204 toward the second end 1218 reducing the volume of the interior space 1206 by an amount corresponding to the reduction in the volume of powder remaining within the interior space 1206 as reduced the powder exits the canister 1202 via the outlet 1210. When the user releases the trigger, both the delivery of the fluidized mixture and the movement of the piston 1204 are halted. Thus, the piston 1204 moves only while the fluidized mixture is being delivered so the reduction in the volume of the interior space 1206 corresponds to the reduction in the volume of powder remaining housed within the interior space 1206. As described above, a rate of movement of the piston 1204 may be based on inputs such as, for example, time, flow and/or pressure within the canister 1202, inlet 1208 and outlet 1210. In one embodiment, the piston 1204 is configured to move at a rate which maintains a substantially constant ratio of the volume of the interior space 1206 available in the canister 1202 to the volume of remaining powder to maintain a substantially constant fluidized mixture delivery rate.

As shown in FIG. 27, a device 1300 according to another embodiment is substantially similar to the device 1200, comprising a canister 1302 and a piston 1304 movably coupled thereto to move from an initial position proximate a first end 1316 of the canister 1302 toward a second end 1318 to reduce a volume of an interior space 1306 of the canister 1302 as a fluidized powder mixture is delivered to a target site. Similarly to the device 1200, high flow gas is delivered to the interior space 1306 to fluidize a powdered agent received within the canister 1302 to form a fluidized mixture for delivery to a target site in the body. Gas is received within the canister 1302 via an inlet 1308 connected to a gas source via, for example, a tubular member 1312. The fluidized mixture is delivered to the target site via a delivery catheter 1314 connected to an outlet 1310 of the device 1300. In this embodiment, however, the piston 1304 is moved via a chamber 1320 including an expandable member 1322, which expands as gas is received therein. In particular, when a user triggers a controller (e.g., depresses a trigger) to deliver the fluidized mixture to the target site, a portion of the gas is diverted into the expandable member 1322 so that the gas expands the expandable member 1322, as shown in broken lines in FIG. 27, thereby moving the piston 1304 toward the second end 1318.

The chamber 1320, which houses the expandable member 1322, in this embodiment is connected to the first end 1316 of the canister 1302 on a side of the piston 1304 opposite the interior space 1306 so that, as the expandable member 1322 expands, the piston 1304 is moved toward the second end 1318 of the canister 1302. The expandable member 1322 is also connected to the gas source via a connecting member 1324, which includes a one way valve so that gas may pass therethrough in a first direction into the expandable chamber 1322, but is prevented from flowing in a second direction out of the expandable chamber 1322. As described above, gas is directed into the chamber 1320 only while the fluidized mixture is being delivered to the target site so that a reduction of the volume of the interior space 1306 corresponds to a reduction in volume of the powdered agent within the canister 1302. Similarly to the device 1200, the device 1300 may receive inputs corresponding to flow, pressure and/or time, that may control a rate at which the piston 1304 is moved toward the second end 1318. It will be understood by those of skill in the art that the device 1300 may be used in a manner substantially similar to the device 1200.

Figure 29:
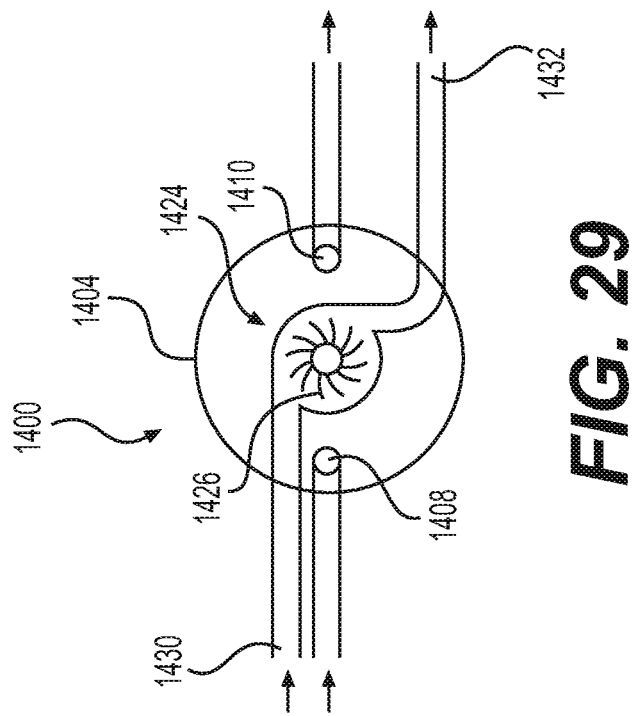
FIG. 29 shows a bottom view of the device according to FIG. 28.
Figure 28:
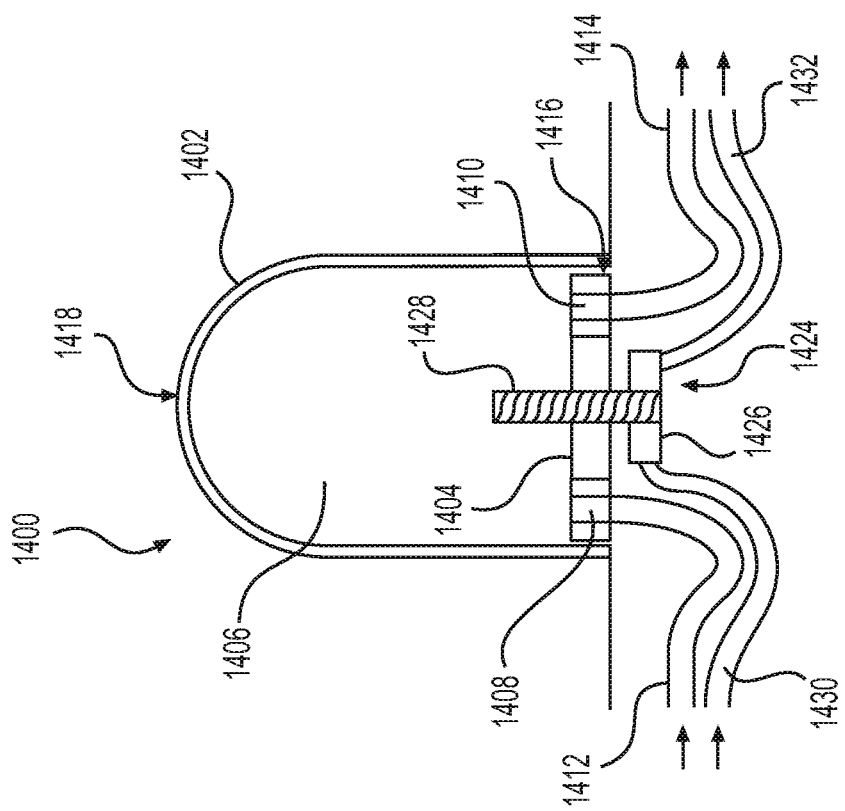
FIG. 28 shows a schematic view of a device according to another alternate embodiment of the present disclosure.

As shown in FIGS. 28 and 29, a device 1400 according to another embodiment may be substantially similar to the devices 1200, 1300 described above, comprising a canister 1402 for receiving a powdered agent within an interior space 1406 thereof and a piston 1404 movably coupled to the canister 1402. High flow gas is delivered to the interior space 1406 via an inlet 1408 that is connected to a gas source to form a fluidized powder mixture for delivery to a target treatment area via a delivery catheter 1414 connected to an outlet 1410 of the device 1400. The piston 1404 is movable from an initial position proximate a first end 1416 of the canister 1402 toward a second end 1418 to reduce a volume of the interior space 1406 as a volume of the powdered agent within the interior space 1406 is reduced. The device 1400, however, further includes a turbine 1426 connected to a threaded rod 1428 to which the piston 1404 is threadedly coupled. The turbine 1426 is housed within a bypass 1424 connected to the first end 1416 if the canister 1402. A portion of the gas is diverted through the bypass 1424 when the user triggers a controller to deliver the fluidized mixture. The flow of gas through the bypass 1424 spins the turbine 1426, thereby causing the threaded rod 1428 to rotate about a longitudinal axis thereof. As the threaded rod 1428 is rotated, the piston 1424 is moved longitudinally therealong toward the second end 1418.

Figure 31:
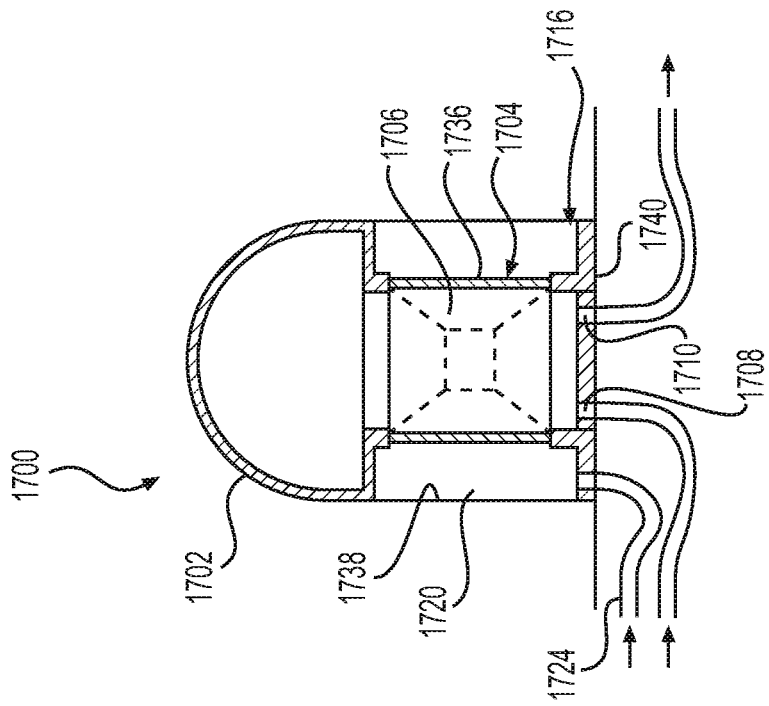
FIG. 31 shows a schematic view of a device according to yet another embodiment of the present disclosure.
Figure 30:
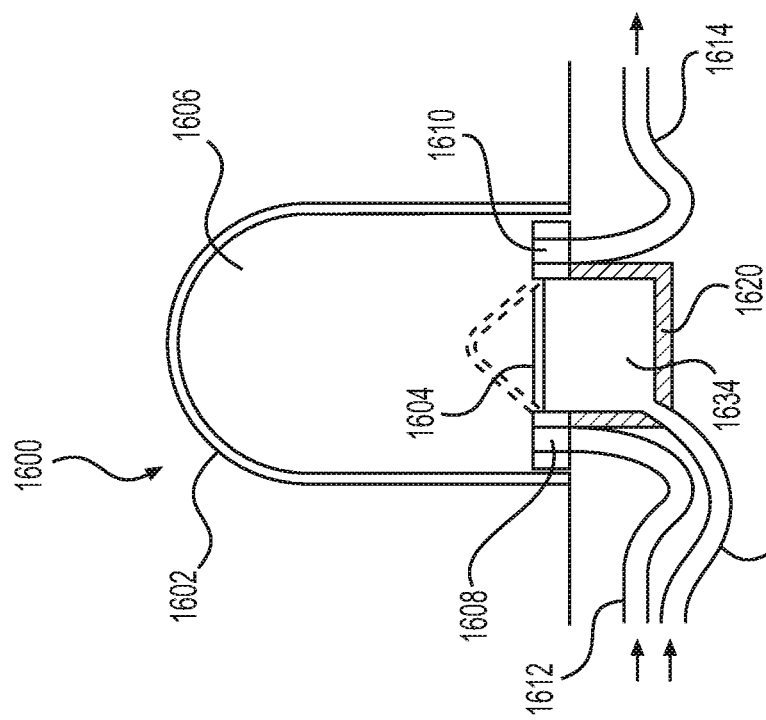
FIG. 30 shows a schematic view of a device according to another embodiment of the present disclosure.

As shown in FIG. 29, the bypass 1424 including a first opening 1430 through which gas is received and second opening 1432 through which gas exits so that gas flows through the bypass 1424 from the first opening 1430 to the second opening 1432 to rotate the turbine 1426 housed therein. The threaded rod 1428 is connected to the turbine 1426 so that rotation of the turbine 1426 results in rotation of the threaded rod 1428. Since the piston 1404 is threaded over the rod 1428, rotation of the threaded rod 1428 causes the piston 1404 to be moved longitudinally therealong. The piston 1404 is threaded over rod 1428 so that rotation of the threaded rod 1428 via the flow of gas through the bypass 1424 results in the longitudinal movement of the piston 1404 toward the second end 1418. Similarly to the device 1300, a portion of the gas is only diverted through the bypass 1424 during delivery of the fluidized mixture so that a reduction in volume of the interior space corresponds to a volume of powder remaining in the interior space 1406. It will be understood by those of skill in the art that the device 1400 may be used in a manner substantially similar to the devices 1200, 1300, as described above.

As shown in FIG. 30, a device 1600 according to another embodiment of the present disclosure may be substantially similar to the devices 1200, 1300, and 1400, described above, comprising a canister 1602 configured to receive a powdered agent therein for fluidization via a gas. Similar to the devices 1200, 1300, and 1400, a volume of an interior space 1606 of the canister 1602 is reduced as a fluidized mixture is delivered to a target site for treatment. Rather than reducing the volume of the interior space 1606 via a movable piston, however, the device 1600 includes an expandable member 1604 which expands into the interior space 1606, as shown in broken lines in FIG. 30, of the canister 1602 to reduce the volume thereof.

Similarly to the devices 1200, 1300, and 1400, gas is supplied into the canister 1602 via an inlet 1608, which may be connected to a gas source via a connecting member 1612. The fluidized mixture is delivered to the target site via a delivery catheter 1614 connected to an outlet 1610. The device 1600 further comprises a secondary chamber 1620 connected to the canister 1602. Similarly to the device 1300 described above, a portion of the gas from the gas source may be diverted into the secondary chamber during delivery of the fluidized mixture. An interior space 1634 of the secondary chamber 1620 is separated from the interior space 1606 of the canister 1602 via the expandable member 1604. In this embodiment, the expandable member 1604 is configured as an expandable diaphragm extending between the canister 1602 and the secondary chamber 1620 so that, when gas is received within the interior space 1634 of the secondary chamber 1620, a pressure differential between the interior space 1634 of the secondary chamber 1620 and the interior space 1606 of the canister 1602 causes the expandable member to deflect into the canister 1602, as shown in broken lines in FIG. 30 reducing the volume of the interior space 1606.

As described above with respect to the devices 1300, 1400, gas is only diverted into the secondary chamber 1620 during the delivery of the fluidized mixture. When delivery is triggered gas is diverted to the secondary chamber 1620. When the user releases the trigger for delivery, delivery of gas to the secondary chamber 1620 is halted. As also discussed above, the amount of flow diverted to the secondary chamber 1620 may be dictated by time, pressure and/or flow detected within the device 1600. As more gas flows into the secondary chamber 1620, its pressure increases to force the diaphragm to deflect further into the interior space 1606 of the canister 1602. Thus, the device 1600 may be utilized in a manner substantially similar to the devices described above.

Although the device 1600 shows and is described with respect to a single expandable diaphragm, it will be understood by those of skill in the art that the device 1600 may include more than one expandable diaphragm and the expandable member may have any of a variety of shapes and configurations.

As shown in FIG. 31, a device 1700 according to another embodiment may be substantially similar to the device 1600, described above, comprising a canister 1702 including an expandable member 1704 which expands to reduce a volume of a first interior space 1706 of the canister 1702 as a powdered agent received therewithin is fluidized and delivered to a target site for treatment. In this embodiment, however, the expandable member 1704 may be housed within the canister 1702 to define both the first interior space 1706 in which the powdered agent is fluidized and a second interior space 1708 into which a portion of a gas may be diverted to cause the expandable member 1704 to deflect into the first interior space 1706 to reduce a volume thereof. A first end 1716 of the canister 1702 may be substantially closed via a base portion 1740. An inlet 1708 for supplying gas into the first interior space 1706 and an outlet 1710 via which the fluidized mixture is delivered to the target site may extend through the base portion 1740 in communication with the first interior space 1706.

The expandable member 1704 may, in one example, have a substantially cylindrical configuration. The cylindrically shaped expandable member 1704 is housed within the canister 1702 so that an interior of the expandable member 1704 defines the first interior space 1706 within which the powdered agent is housed and subsequently fluidized via a high flow gas supplied from a gas source thereto via the inlet 1708. The second interior space 1720 is defined via an exterior surface 1736 of the expandable member 1704 and an interior surface 1738 of the canister 1702 so as the fluidized mixture is delivered to the target site from the first interior space 1706 via a delivery catheter 1714 connected to the outlet 1710, a portion of gas from the gas source gas is diverted into the second interior space 1738 via a connecting element 1724. A pressure differential between the first and second interior spaces 1706, 1720 causes the expandable member 1704 to deflect into the first interior space 1706, as shown in broken lines in FIG. 31, toward an expanded configuration, as shown via the broken lines in FIG. 31, reducing the volume of the first interior space 1706 as a volume of the powder in the first interior space 1706 is reduced. In one embodiment, in the expanded configuration, the expandable member 1704 may form a substantially hourglass shape. It will be understood by those of skill in the art, however, that the expandable member 1704 may have any of a variety of shapes and configurations so long as the expandable member 1704, when expanded, reduces a volume of the first interior space 1706. Similarly to the devices described above, gas is only diverted into the second interior space 1720 during delivery of the fluidized mixture and may be controlled via inputs including time, and/or flow and/or pressure within the device 1700.

Although the device 1700 is shown and described as including a substantially cylindrically shaped expandable member 1704, it will be understood by those of skill in the art that the expandable member 1704 may have any of a variety of shapes so long as the expandable member defines first and second interior spaces 1706, 1720, as described above.

Figure 32:
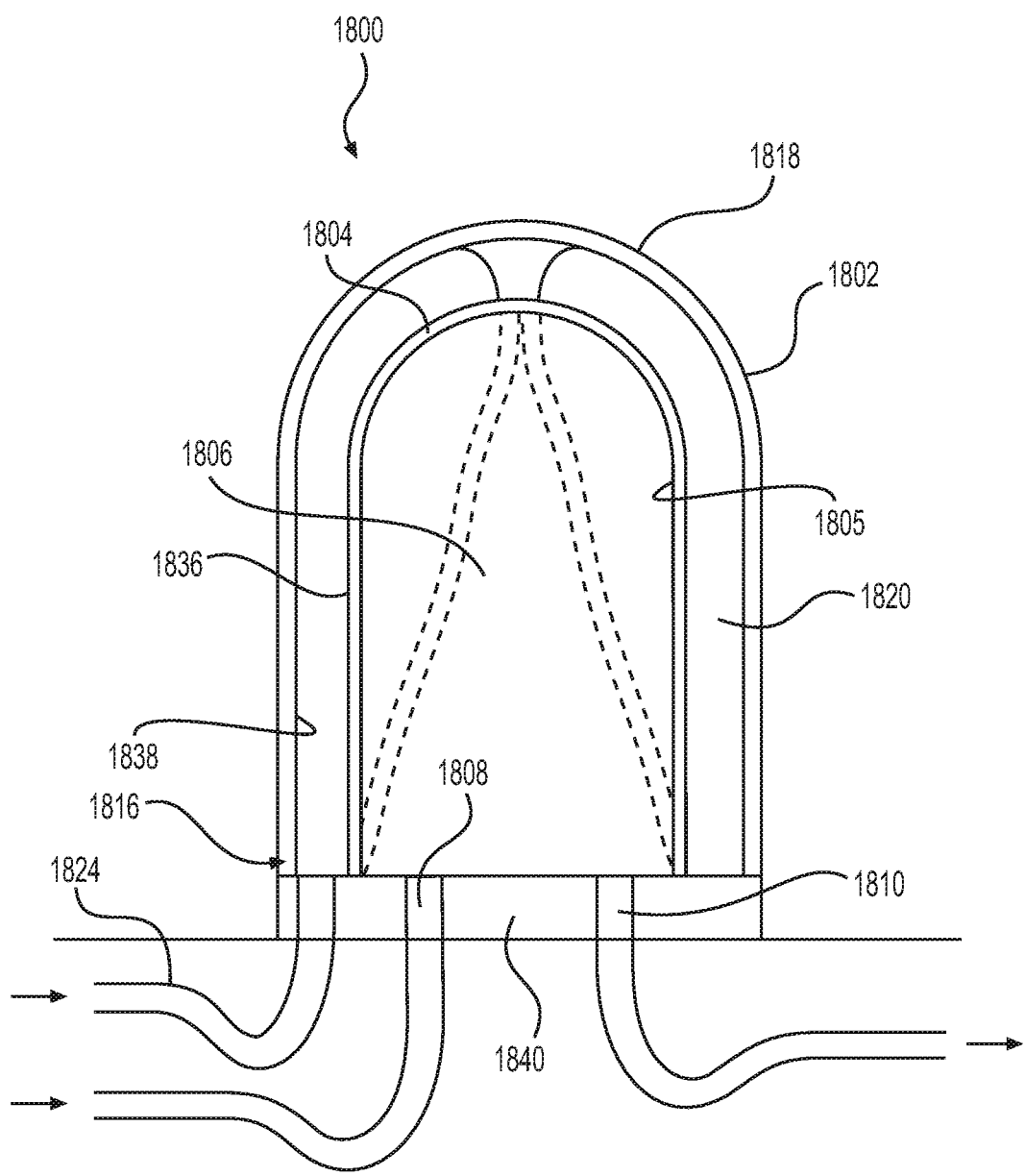
FIG. 32 shows a schematic view of a device according to another embodiment.
Figure 34:
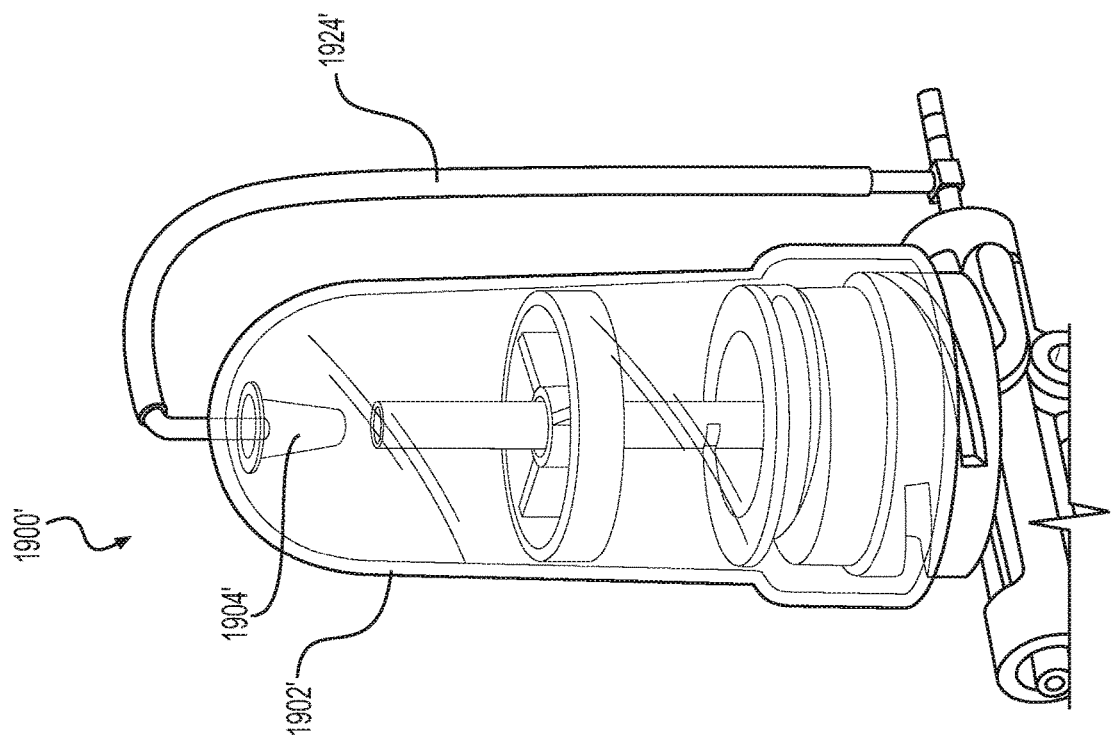
FIG. 34 shows a schematic view of a device according to an alternate of the present disclosure.
Figure 33:
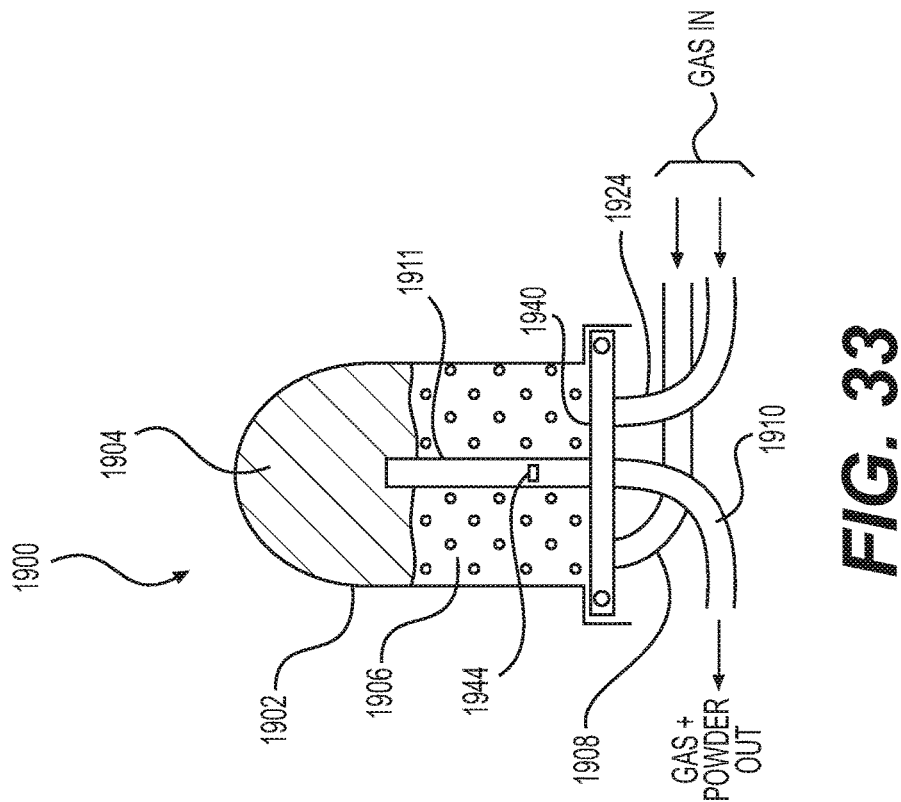
FIG. 33 shows a schematic view of device according to yet another embodiment of the present disclosure.

As shown in FIG. 32, a device 1800 according to another embodiment may be substantially similar to the device 1700 described above, comprising a canister 1802 and an expandable member 1804 defining a first interior space 1806, in which a powdered agent is fluidized via gas from a gas source to form a fluidized mixture, and a second interior space 1820, which receives a portion of gas diverted from the gas source during delivery of the fluidized mixture to a target treatment area. The first interior space 606 is defined via an interior wall 1805 of the expandable member 1804. The second exterior space 1820 is defined via an exterior wall 1836 of the expandable member 1806 and the interior surface 1838 of the canister 1802. In this embodiment, however, the expandable member 1804 extends from a first end 1816 of the canister 1802 to a second end 1818 of the canister 1802 so that, in an initial biased configuration, the expandable member 1804 may substantially correspond in shape to the canister 1802. As the second interior space 1820 is filled with diverted gas, however, the expandable member 1804 deflects into the first interior space 1806, as shown in broken lines in FIG. 32, increasing a volume of the second interior space 1820 and thereby reducing a volume of the second interior space 1820.

Similarly to the device 1700, the device 1800 also includes a base portion 1840 at a first end 1816 of the canister 1802 for enclosing the first and second interior spaces 1806, 1820. An inlet 1808 and an outlet 1810 extend through the base portion 1840 in communication with the first interior space 1806 so that gas may be supplied thereto via the inlet 1808 to fluidize the powdered agent therein and so that the fluidized mixture may be delivered to the target site via the outlet 1810. A portion of the gas from the gas source may be diverted into the second interior space 1820 via a connecting element 1824, which may be positioned along the base portion 1840 in communication with the second interior space 1820.

As described above, during delivery of the fluidized mixture to the target site, a portion of the gas is diverted into the second interior space 1820 so that a pressure differential between the first and second interior spaces 1806, 1820 causes the expandable member to be diverted radially inward, as shown in broken-lines in FIG. 32, to reduce the volume of the first interior space 1806. Thus, as the volume of the powdered agent within the first interior space 1806 is reduced, the volume of the first interior space 1806 is correspondingly reduced to maintain a substantially constant delivery rate of the fluidized mixture. In a diverted configuration, the expandable member 1804 may take on a substantially conical shape. It will be understood by those of skill in the art, however, that the expandable member 1804 may have any of a configurations, shapes and sizes so long as the expandable member 1804 is formed of a flexible, deflectable material which defines both a first interior space 1806 within walls thereof, and a second interior space 1820 between the expandable member 1804 and walls of the canister 1802.

As shown in FIG. 33, a device 1900 according to another embodiment may be substantially similar to the devices 1600, 1700, and 1800 described above, comprising a canister 1902 and an expandable member 1904, which expands to reduce a volume of an interior space 1906 of the canister 1902 as a powdered agent is fluidized and delivered to a target site of treatment. The volume of the interior space 1906 is reduced to correspond to a reduction in a volume of the powdered agent within the interior space 1906. The expandable member 1904 in this embodiment, however, is configured as an expandable balloon housed within the interior space 1906. Thus, as a volume of the balloon 1904 is increased as it is inflated, the volume of the interior space 1906 is decreased.

Similarly to the devices 1600, 1700, and 1800, the device 1900 includes an inlet 1908 for supplying a gas to the interior space 1906 to fluidize the powdered agent and an outlet 1910 via the fluidized mixture is delivered to the target site. The inlet and outlet 1908, 1910 may be extend through a base portion 1940 of the device 1900 which is coupled to an end of the canister 1902 to define the interior space 1906. A portion of the gas supplied to the device 1900 may be diverted to the expandable member 1904 via a connecting element 1924 to cause the balloon to become inflated, filling the interior space 1906. As described above, the inlet 1908 may have any of a variety of configurations and, in one embodiment, may include a hypotube 1911 extending into the interior space 1906. The hypotube 1911 may include a slot 1944 extending through a wall thereof along a portion thereof. The inflated expandable member 1904 may fill the space, surrounding the hypotube 1911 without restricting gas and powder flow through the slot 1944. Although the hypotube 1911 is described as including the slot 1944, it will be understood by those of skill in the art that the term "slot" may refer to any opening or hole extending through a wall thereof.

The connecting element 1924 may be coupled to the base portion 1940, as shown, to deliver gas to the expandable member 1904. It will be understood by those of skill in the embodiment, that the connecting element 1920 may extend through the interior space 1906 to connect to the expandable member 1904. Alternatively, as shown in FIG. 34, a device 1900' may have a separate feed line 1924' which extends through a portion of a canister 1902' to supply gas to an expandable member 1904' housed therein. It will be understood by those of skill in the art that an expandable member 1904, 1904' having a balloon configuration may be supplied with gas for inflating the expandable member via any of a variety of mechanisms.

Catheter 190 is shown in FIG. 35 in a coiled, rolled-up configuration. Catheter 190 includes a proximal end 191, a distal end 193, and an intermediate portion 192 connecting proximal end 191 and distal end 193. Proximal end 191 may be connected to outlet 34 by any mechanism, such as a screw or snap fit mechanism. Alternatively, proximal end 191 may be a complementary luer, e.g. a male or a female luer, to a luer provided at outlet 34. As shown in FIG. 35, proximal end 191 may include a butterfly-shaped device to assist in screwing or otherwise attaching catheter 190 to application device 30. When a propellant fluid and material mixture is dispensed from application device 30, the mixture may travel through catheter 190 (preferably in an unrolled configuration) and may be dispensed from distal end 193 at the target site. Catheter 190 may be any size appropriate for introducing the device into a patient while maintaining column strength such that catheter 190 does not buckle when passed though an endoscope. For example, catheter 190 may be approximately 200-275 cm, and preferably approximately 210-250 cm. Further, a diameter of catheter 190 may be approximately seven (7) to eight (8) French, and a wall thickness of catheter 190 may be approximately 0.05-0.15 inches, or preferably approximately 0.1 inches. In addition, catheter 190 may be nylon or any other suitable material. However, the size and the material of the catheter is not limited thereto.

Although many features are described as cylindrical, the shape of the elements are not limited thereto. Rather, the features may be any shape suitable for regulator 40 to properly regulate a fluid dispersion from containment device 20, 20'. Moreover, unless described otherwise, the structural elements of application device 30 and/or regulator 40, 40' may be any material known in the art, including but not limited to a metal alloy, a ceramic, and/or a resin. Further, although the above embodiments are described as diverting a portion of gas from a gas source/supply to drive movement of a piston or expansion of an expandable member, it will be understood by those of skill in the art that the devices described above may include one or more gas source(s) for providing gas to both the interior space and for driving the piston and/or causing expansion of the expandable member.

It will be apparent to those skilled in the art that various modifications and variations can be made to the disclosed device without departing from the scope of the disclosure. For example, any material or fluid may be contained in the chamber and may mix with the propellant fluid to be expelled from the application device to a target location. Additionally, or alternatively, unless otherwise specified, the medical device described herein may be formed of any metal, plastic, or ceramic, or any combination thereof, suitable for use in medical applications. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    an application device having a first fluid path therethrough; and
    a first container movably attached to the application device, wherein the first container and the application device have a second fluid path therethrough, wherein the first container includes an inner chamber that is intermediate proximal and distal portions of the second fluid path, and wherein the tube extends through the inner chamber, and the tube includes a port for receiving an agent stored in the inner chamber;
    wherein the inner chamber is fluidly isolated from the distal portion of the second fluid path at a first position of the tube relative to the first container such that the distal portion of the second fluid path is not in communication with the agent from the inner chamber through the port, and wherein the inner chamber is fluidly coupled to the proximal and distal portions of the second fluid path at a second position of the tube relative to the first container such that the distal portion of the second fluid path is in communication with the agent from the inner chamber through the port, wherein the first container is attached to the application device when in the first position and the second position;
    wherein;
    the first fluid path bypasses the first container, and
    the passage of fluid of fluid through the first fluid path is separately controllable from the passage of fluid through the second fluid path.

2. The medical device according to claim 1, further comprising:
    a second container including a propellant fluid and configured to be attached to an inlet of the application device.

3. The medical device according to claim 2, wherein the application device further includes a locking mechanism for securing the second container to the application device.

4. The medical device according to claim 3, wherein the locking mechanism includes:
    a lever pivotally connected to the application device;
    a piston connected to the lever and contacting the second container,
    wherein in a first position of the lever, the second container is fluidly decoupled from the application device, and in a second position of the lever, the second container is fluidly coupled to the application device.

5. The medical device according to claim 4, wherein a protrusion extends from a surface of the piston toward the inlet, wherein a void extends into the first container from a surface facing the piston, and wherein the protrusion extends into the void and maintains a fixed position of the first container with respect to the piston.

6. The medical device according to claim 2, wherein the inner chamber includes one or more protrusions extending from a bottom surface of the inner chamber into the inner chamber, and
    wherein the one or more protrusions are configured to change a fluid path of the propellant fluid in the inner chamber.

7. The medical device according to claim 2, wherein the application device further includes first and second actuation devices, wherein the first actuation device is configured to control the propellant fluid in the first fluid path, and
    wherein the second actuation device is configured to control the propellant fluid in the second fluid path.

8. The medical device according to claim 1, wherein the first container includes (a) a chamber inlet between the inner chamber and the proximal portion of the second fluid path, and (b) a chamber filter,
    wherein the chamber filter is configured to allow a fluid to enter the inner chamber from the proximal portion of the second fluid path, and wherein the chamber filter is configured to prevent a material disposed in the first container from entering the proximal portion of the second fluid path.

9. The medical device according to claim 1, wherein a sheath is disposed about the tube,
wherein the port is covered by the sheath when the tube is positioned relative to the first container at the first position, and
wherein the port is exposed from the sheath when the tube is positioned relative to the first container at the second position.

10. The medical device according to claim 9, wherein the inner chamber further includes an attachment member fixedly attached to the sheath and an outer surface of the first container, and wherein rotation of the outer surface causes the sheath to move longitudinally on the tube.

11. The medical device according to claim 10, wherein the application device includes a groove having a first end and a second end,
wherein the first container includes a cam extending from the outer surface of the first container,
wherein the cam is within the groove,
wherein the cam is disposed at the first end of the groove when the tube is positioned relative to the first container at the first position, and
wherein the cam is disposed at the second end of the groove when the tube is positioned relative to the first container at the second position.

12. The medical device according to claim 1, wherein the second fluid path includes a pressure release mechanism configured to release fluid when a pressure of a fluid in the second fluid path is greater than a threshold, and wherein the threshold is greater than a desired pressure of a fluid at an outlet of the second fluid path.

13. The medical device according to claim 12, wherein the pressure release mechanism includes a burst disc and is disposed in the inner chamber of the first container.

14. The medical device according to claim 2, wherein the inlet of the application device includes a second pressure release mechanism, and wherein actuation of the second pressure release mechanism releases the propellant fluid from the second container.

15. The medical device according to claim 1, further comprising:
a catheter attached to an outlet of the distal portion of the second fluid path, via a luer connection.

16. A medical device, comprising:
an application device having a first fluid path therethrough; and
a container movably attached to the application device, wherein the container and the application device have a second fluid path therethrough, wherein the first container has an inner chamber having an inlet configured to be fluidly coupled to a proximal portion of the second fluid path and an outlet configured to be fluidly coupled to a distal portion of the second fluid path;
wherein a tube extends through the inner chamber of the container, and the tube includes a port for receiving an agent stored in the inner chamber, and
wherein the inner chamber is fluidly decoupled from the distal portion of the second fluid path when the container is attached to the application device with the tube at a first position such that agent from the inner chamber is not in fluid communication with the distal portion of the second fluid path via the port, and the inner chamber is fluidly coupled to the proximal and distal portions of the second fluid path when the container is attached to the application device with the tube at a second position such that the agent from the inner chamber is in fluid communication with the distal portion of the second fluid path via the port.

17. The medical device according to claim 16, wherein a sheath is disposed about the tube,
wherein the port is covered by the sheath when the tube within the inner chamber of the container is at the first position, and
wherein the port is exposed from the sheath when the tube within the inner chamber of the container is at the second position.

18. The medical device according to claim 16, wherein the application device includes a groove having a first end and a second end,
wherein the container includes a cam extending from an outer surface of the container,
wherein the cam is within the groove,
wherein the cam is disposed at the first end of the groove when the tube within the inner chamber of the container is at the first position, and
wherein the cam is disposed at the second end of the groove when the tube within the inner chamber of the container is at the second position.

19. A medical device, comprising:
an application device having a first fluid path, an inlet, and an outlet; and
a first container attached to the application device, wherein the first container and the application device have a second fluid path therethrough, wherein the first container includes an inner chamber between distal and proximal portions of the second fluid path, wherein the inner chamber includes an inflow configured to be fluidly coupled to the proximal portion of the second fluid path and an outflow configured to be fluidly coupled to the distal portion of the second fluid path, and wherein a tube extends through the inner chamber, and the tube includes at least one port fluidly isolated from the inner chamber when the tube within the inner chamber of the first container is in a first position, such that the agent from the inner chamber is not in communication with the distal portion of the second fluid path via the at least one port, and fluidly coupled to the inner chamber when the tube within the inner chamber of the first container is in a second position, such that the agent from the inner chamber is in fluid communication with the distal portion of the second fluid path via the at least one port;
wherein fluid from the first fluid path travels from the inlet to the outlet, bypassing the first container, and the first containers attached to the application device when the tube is in the first position and the second position.

20. The medical device according to claim 19, further comprising:
a second container including a propellant fluid; and
a locking mechanism, wherein the locking mechanism includes:
a lever pivotally connected to the application device;
a piston connected to the lever and contacting the second container,
wherein in a first position of the lever, the second container is fluidly decoupled from the application device, and in a second position of the lever, the second container is fluidly coupled to the application device.

* * * * *